US009620722B2

(12) United States Patent
Martynova et al.

(10) Patent No.: US 9,620,722 B2
(45) Date of Patent: Apr. 11, 2017

(54) MATERIALS FOR ORGANIC ELECTROLUMINESCENT DEVICES

(75) Inventors: Irina Martynova, Griesheim (DE); Christof Pflumm, Darmstadt-Arheilgen (DE); Amir Hossain Parham, Frankfurt am Main (DE); Rémi Manouk Anémian, Seoul (KR); Teresa Mujica-Fernaud, Darmstadt (DE); Claire De Nonancourt, Darmstadt (DE)

(73) Assignee: Merck Patent GmbH, Darmstadt (DE)

(*) Notice: Subject to any disclaimer, the term of this patent is extended or adjusted under 35 U.S.C. 154(b) by 662 days.

(21) Appl. No.: 14/112,431

(22) PCT Filed: Mar. 26, 2012

(86) PCT No.: PCT/EP2012/001320
§ 371 (c)(1),
(2), (4) Date: Oct. 17, 2013

(87) PCT Pub. No.: WO2012/143080
PCT Pub. Date: Oct. 26, 2012

(65) Prior Publication Data
US 2014/0042370 A1   Feb. 13, 2014

(30) Foreign Application Priority Data

Apr. 18, 2011   (EP) ..................... 11003232

(51) Int. Cl.
| | | |
|---|---|---|
| *H01L 51/00* | (2006.01) | |
| *C07D 471/04* | (2006.01) | |
| *C07D 471/16* | (2006.01) | |
| *C07D 491/16* | (2006.01) | |
| *C07D 491/22* | (2006.01) | |
| *C07D 495/04* | (2006.01) | |
| *C07D 495/16* | (2006.01) | |
| *C07D 495/22* | (2006.01) | |
| *C07D 498/16* | (2006.01) | |
| *C07D 519/00* | (2006.01) | |
| *C09K 11/06* | (2006.01) | |
| *H05B 33/14* | (2006.01) | |
| *C09B 57/00* | (2006.01) | |
| *H01L 51/50* | (2006.01) | |

(52) U.S. Cl.
CPC .......... *H01L 51/006* (2013.01); *C07D 471/04* (2013.01); *C07D 471/16* (2013.01); *C07D 491/16* (2013.01); *C07D 491/22* (2013.01); *C07D 495/04* (2013.01); *C07D 495/16* (2013.01); *C07D 495/22* (2013.01); *C07D 498/16* (2013.01); *C07D 519/00* (2013.01); *C09B 57/00* (2013.01); *C09B 57/008* (2013.01); *C09K 11/06* (2013.01); *H01L 51/0065* (2013.01); *H01L 51/0067* (2013.01); *H01L 51/0068* (2013.01); *H01L 51/0071* (2013.01); *H01L 51/0072* (2013.01); *H01L 51/0074* (2013.01); *H05B 33/14* (2013.01); *C09K 2211/1033* (2013.01); *C09K 2211/1037* (2013.01); *C09K 2211/1044* (2013.01); *C09K 2211/1051* (2013.01); *C09K 2211/1059* (2013.01); *C09K 2211/1074* (2013.01); *C09K 2211/185* (2013.01); *H01L 51/0085* (2013.01); *H01L 51/0087* (2013.01); *H01L 51/5016* (2013.01); *H01L 51/5072* (2013.01); *H01L 51/5096* (2013.01); *H01L 2251/5384* (2013.01)

(58) Field of Classification Search
CPC .................... H01L 51/0061; C09K 2211/1074
See application file for complete search history.

(56) References Cited

U.S. PATENT DOCUMENTS

| | | | |
|---|---|---|---|
| 9,034,485 B2 | 5/2015 | Buesing et al. | |
| 2009/0295275 A1 | 12/2009 | Parham et al. | |
| 2010/0051928 A1* | 3/2010 | Fukuzaki | C07D 471/16 257/40 |
| 2011/0266533 A1 | 11/2011 | Buesing et al. | |
| 2012/0202997 A1 | 8/2012 | Parham et al. | |

FOREIGN PATENT DOCUMENTS

| | | |
|---|---|---|
| JP | 2001-160488 A | 6/2001 |
| JP | 2001160488 | 6/2001 |
| JP | 2003022893 A | 1/2003 |
| WO | WO-2006033563 A1 | 3/2006 |
| WO | WO-2007031165 A2 | 3/2007 |
| WO | WO-2010083871 A1 | 7/2010 |
| WO | WO-2011042107 A2 | 4/2011 |

OTHER PUBLICATIONS

Buehrdel, G., Beckert, R., Herzigova, P., Petrlikova, E., Schuch, D., Birckner, E. and Goerls, H. (2009), A New Synthesis of Push-Pull Pyrroles, Their Oxidation to Stable 3H-Pyrroles and an Unexpected Anellation Reaction. Eur. J. Org. Chem., 2009: 3404-3412. doi: 10.1002/ejoc.200900295.*
Rahimizadeh et al., "Synthesis of Novel Heterocyclic System, 4h-Imidazo [2,1-b] Pyrimido [4,5-e] [1,3,4] Thiadiazine", Indian Journal of Heterocyclic Chemistry, vol. 6, No. 3, pp. 223-224 (1997).
Rahimizadeh et al., "Synthesis of Novel Heterocyclic System, 4h-Imidazo [2,1-b] Pyrido [2,3-e] [1,3,4] Thiadiazine", Journal of Sciences Islamic Republic of Iran, vol. 9, No. 2, pp. 163-165 (1998).
Caplus Database, Accession No. XP002680917, retrieved Jul. 20, 2012.
Caplus Database, Accession No. XP002680918, retrieved Jul. 19, 2012.
Caplus Database, Accession No. XP002680919, retrieved Jul. 19, 2012.

(Continued)

*Primary Examiner* — Alex A Rolland
(74) *Attorney, Agent, or Firm* — Drinker Biddle & Reath LLP

(57) ABSTRACT

The present invention relates to compounds of the formula (1) and formula (2), which are suitable for use in electronic devices, in particular in organic electroluminescent devices.

20 Claims, No Drawings

(56) References Cited

OTHER PUBLICATIONS

Xie, Rui-Hua, et al., "Tuning Spectral Properties of Fullerenes by Substitutional Doping", Physical Review B, vol. 69, (2004), pp. 201403-1 to 201403-4.
Caplus Database, Accession No. XP002680920, retrieved Jul. 19, 2012.
International Search Report for PCT/EP2012/001320 mailed Oct. 16, 2012.

* cited by examiner

MATERIALS FOR ORGANIC ELECTROLUMINESCENT DEVICES

RELATED APPLICATIONS

This application is a national stage application (under 35 U.S.C. §371) of PCT/EP2012/001320, filed Mar. 26, 2012, which claims benefit of European Application No. 11003232.3, filed Apr. 18, 2011. Both are incorporated herein by reference in their entirety.

The present invention relates to materials for use in electronic devices, in particular in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters. In general, there is still a need for improvement in OLEDs, in particular also in OLEDs which exhibit triplet emission (phosphorescence), for example with respect to efficiency, operating voltage and lifetime. This applies, in particular, to OLEDs which emit in the relatively short-wave region.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials may thus also result in significant improvements in the OLED properties. There is also a need for improvement in these materials for fluorescent OLEDs too.

In accordance with the prior art, ketones (for example in accordance with WO 2004/093207 or WO 2010/006680) or phosphine oxides (for example in accordance with WO 2005/003253), inter alia, are used as matrix materials for phosphorescent emitters. However, there is still a need for improvement on use of these matrix materials as in the case of other matrix materials, in particular with respect to the efficiency, the lifetime and the operating voltage of the device.

The object of the present invention is the provision of compounds which are suitable for use in a fluorescent or phosphorescent OLED, in particular a phosphorescent OLED, for example as matrix material or as hole-transport/electron-blocking material or exciton-blocking material or as electron-transport or hole-blocking material. In particular, the object of the present invention is to provide matrix materials which are also suitable for green- and optionally also for blue-phosphorescent OLEDs, and to provide novel hole-transport materials and electron-transport materials.

Surprisingly, it has been found that certain compounds described in greater detail below achieve this object and result in improvements in the organic electroluminescent device, in particular with respect to the lifetime, the efficiency and the operating voltage. This applies, in particular, to green- and blue-phosphorescent electroluminescent devices, especially on use of the compounds according to the invention as matrix material, but also for the use of the compounds as hole-transport material, hole-injection material, electron-transport material or hole-blocking material, depending on the precise substitution of the compound. The present invention therefore relates to these materials and to organic electroluminescent devices which comprise compounds of this type.

WO 2007/031165 discloses bridged triphenylamine structures having a similar basic structure to the compounds according to the invention. However, compounds which contain five-membered heteroaryl ring groups instead of the phenyl groups are not disclosed therein. Furthermore, these compounds are only described as emitters or as hole-transport material, but not as matrix material for phosphorescent emitters or as electron-transport material.

WO 2010/050778 discloses bridged triphenylamine and phenylcarbazole structures having a similar basic structure to the compounds according to the invention. However, compounds which contain bridged five-membered heteroaryl ring groups instead of the phenyl groups are not disclosed therein.

DE 102009053836.4, which has not been published, discloses bridged triarylamine structures having a similar basic structure to the compounds according to the invention, where at least one of the aromatic groups which are bonded to the nitrogen represents a six-membered heteroaryl ring group. However, compounds which contain bridged five-membered heteroaryl ring groups instead of the six-membered heteroaryl ring groups are not disclosed therein.

Surprisingly, it has been found that specifically the use of the compounds according to the invention in organic electroluminescent devices results in good electronic properties.

The present invention therefore relates to a compound of the following formula (1) or formula (2),

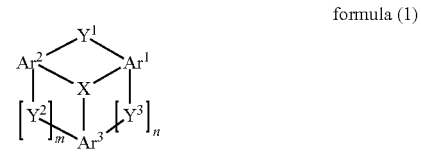

formula (1)

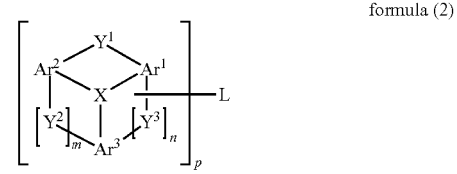

formula (2)

where the following applies to the symbols and indices used:
X is on each occurrence, identically or differently, N, P or P=O;
$Y^1$, $Y^2$, $Y^3$ is on each occurrence, identically or differently, a single bond or $C(R^1)_2$, $NR^1$, O, S, C=O, C=$NR^1$, C=$C(R^1)_2$, $Si(R^1)_2$, $BR^1$, $PR^1$, P(=O)$R^1$, SO, $SO_2$; with the proviso that not all $Y^1$, $Y^2$ and $Y^3$ simultaneously stand for a single bond;
and furthermore with the proviso that $Y^1$ in formula (1) does not stand for a single bond or C=O if n+m=0;
$Ar^1$ is on each occurrence, identically or differently, a group of the following formula (3), formula (4) or formula (5),

formula (3)

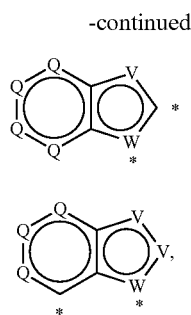

formula (4)

formula (5)

where the group is bonded to X and to $Y^1$ via the two positions denoted by * and where the group may be bonded to $Y^3$ via a further adjacent position and in which:

W is on each occurrence, identically or differently, C or N;

V for W=C is on each occurrence, identically or differently, CR, N, NR, S or O, with the proviso that precisely one symbol V stands for NR, S or O;

or for W=N is on each occurrence, identically or differently, CR or N;

Q is on each occurrence, identically or differently, CR or N;

V or Q here stands for C if a group $Y^3$ is bonded to this group V or Q;

$Ar^2$, $Ar^3$ is on each occurrence, identically or differently, an aryl or heteroaryl group having 5 to 18 aromatic ring atoms, which may be substituted by one or more radicals R;

L is a di-, tri-, tetra-, penta- or hexavalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms or an alkenylene or alkynylene group having 2 to 40 C atoms, which may be substituted by in each case one or more radicals $R^2$, where one or more non-adjacent $CH_2$ groups may be replaced by $-R^2C=CR^2-$, $-C\equiv C-$, $Si(R^2)_2$, C=O, C=NR$^2$, P(=O)R$^2$, S=O, SO$_2$, $-O-$, $-S-$ or $-CONR^2-$ and where one or more H atoms may be replaced by D, F, Cl, Br, I, CN or NO$_2$, or a di-, tri-, tetra-, penta- or hexavalent aromatic or heteroaromatic ring system having 5 to 40, aromatic ring atoms, which may be substituted by one or more radicals $R^2$, or $P(R^2)_{3-p}$, $P(=O)(R^2)_{3-p}$, $C(R^2)_{4-p}$, $Si(R^2)_{4-p}$, $N(Ar)_{3-p}$ or a combination of two, three, four or five of these systems; or L is a chemical bond; in this case, L is bonded to any desired position of $Ar^1$, $Ar^2$, $Ar^3$, $Y^1$, $Y^2$ or $Y^3$ instead of a radical R or $R^1$;

R, $R^1$ is selected on each occurrence, identically or differently, from the group consisting of H, D, F, Cl, Br, I, CN, NO$_2$, N(Ar)$_2$, N(R$^2$)$_2$, C(=O)Ar, C(=O)R$^2$, P(=O)(Ar)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, an aromatic or heteroaromatic ring system having 5 to 80, preferably 5 to 60, aromatic ring atoms, which may in each case be substituted by one or more radicals $R^2$, an aryloxy or heteroaryloxy group having 5 to 60 aromatic ring atoms, which may be substituted by one or more radicals $R^2$, or an aralkyl or heteroaralkyl group having 5 to 60 aromatic ring atoms, which may be substituted by one or more radicals $R^2$, where two or more adjacent substituents R or two substituents $R^1$ which are bonded in the same group Y may optionally form with one another a mono- or polycyclic, aliphatic, aromatic or heteroaromatic ring system, which may be substituted by one or more radicals $R^2$;

$R^2$ is selected on each occurrence, identically or differently, from the group consisting of H, D, F, Cl, Br, I, CN, NO$_2$, N(Ar)$_2$, N(R$^3$)$_2$, C(=O)Ar, C(=O)R$^3$, P(=O)(Ar)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $R^3C=CR^3$, C≡C, Si(R$^3$)$_2$, Ge(R$^3$)$_2$, Sn(R$^3$)$_2$, C=O, C=S, C=Se, C=NR$^3$, P(=O)(R$^3$), SO, SO$_2$, NR$^3$, O, S or CONR$^3$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals $R^3$, an aryloxy or heteroaryloxy group having 5 to 60 aromatic ring atoms, which may be substituted by one or more radicals $R^3$, or an aralkyl or heteroaralkyl group having 5 to 60 aromatic ring atoms, where two or more adjacent substituents $R^2$ may optionally form a monocyclic or polycyclic, aliphatic, aromatic or heteroaromatic ring system, which may be substituted by one or more radicals $R^3$;

Ar is on each occurrence, identically or differently, an aromatic or heteroaromatic ring system having 5-30 aromatic ring atoms, which may be substituted by one or more non-aromatic radicals $R^3$; two radicals Ar which are bonded to the same N atom or P atom may also be bridged to one another here by a single bond or a bridge selected from N(R$^3$), C(R$^3$)$_2$, O or S;

$R^3$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^3$ may form a mono- or polycyclic, aliphatic, aromatic or heteroaromatic ring system with one another;

m, n is on each occurrence, identically or differently, 0 or 1, where m=0 or n=0 means that no group Y is present;

p is 2, 3, 4, 5 or 6, with the proviso that p is not greater than the maximum valence of L;

the following compounds are excluded from the invention:

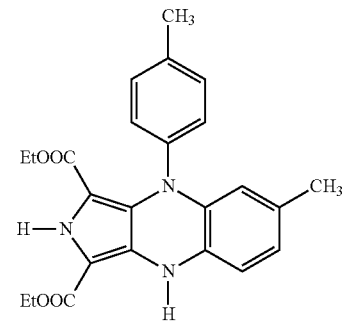

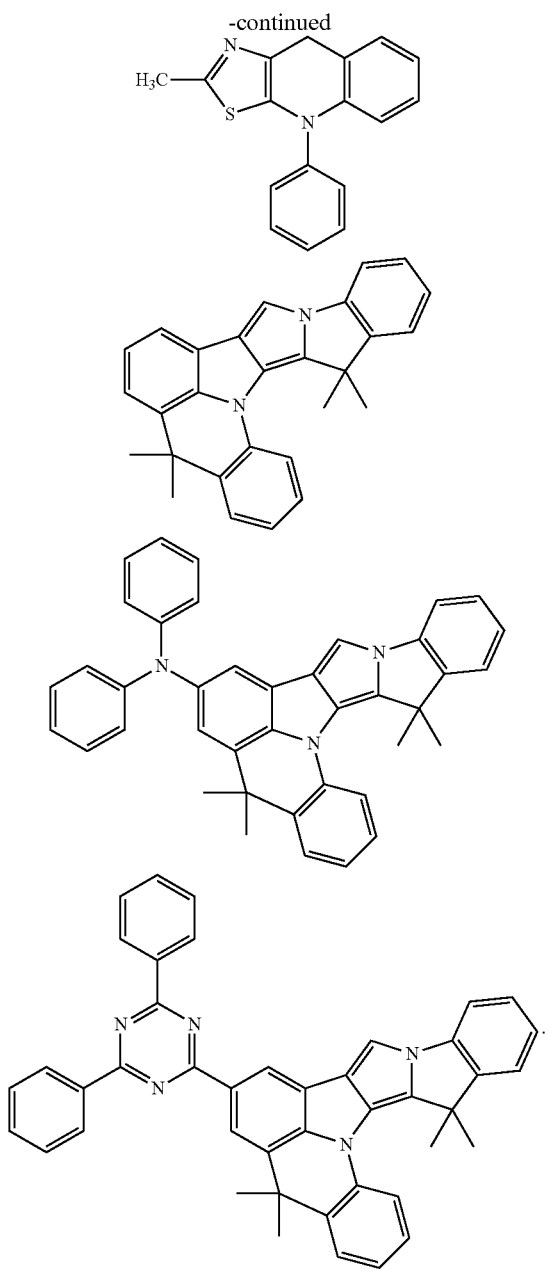

The circle in the formulae (3), (4) and (5) and in formulae which follow below indicates that it is an aromatic or heteroaromatic structure, as generally usual in organic chemistry.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic rings linked to one another by a single bond, such as, for example, biphenyl, are, by contrast, not referred to as an aryl or heteroaryl group, but instead as an aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are connected, for example, by a short alkyl group. Furthermore, aromatic rings linked to one another by a single bond, such as, for example, biphenyl, are referred to as an aromatic ring system in the sense of this application.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkenyl, alkynyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-80 aromatic ring atoms, which may also in each case be substituted by the above-mentioned radicals $R^2$ or a hydrocarbon radical and which may be linked via any desired positions on the aromatic or heteroaromatic group, is taken to mean, in particular, groups derived from benzene, naphthalene, anthracene, benzanthracene, phenanthrene, benzo-phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems.

In a preferred embodiment of the invention, $Ar^2$ and $Ar^3$ stand, identically or differently on each occurrence, for an aryl or heteroaryl group having 5 to 10 aromatic ring atoms, which may be substituted by one or more radicals R, in particular for benzene, thiophene, pyrrole, furan, pyridine, pyrimidine, triazine, benzothiophene, indole, benzofuran or naphthalene. $Ar^e$ and $Ar^3$ particularly preferably stand, identically or differently on each occurrence, for benzene or pyridine, in particular for benzene.

In a further preferred embodiment of the invention, the group $Ar^1$ is bonded to X and to $Y^1$ via two directly adjacent atoms, i.e. via two atoms which are bonded directly to one another.

$Ar^1$ therefore preferably stands for a group of the above-mentioned formula (3) or (4).

If $Ar^1$ stands for a group of the formula (5), $Y^1$ is preferably a single bond.

In a further preferred embodiment of the invention, if $Ar^1$ stands for a structure of the formula (3) and a group V stands for NR, this radical R which is bonded to the nitrogen is not involved in the formation of further ring systems. Particularly preferably, no further rings are condensed onto the group $Ar^1$.

Preferred embodiments of the formula (1) are therefore compounds of the following formulae (5) to (11),

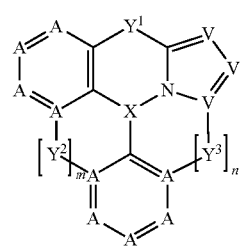

formula (5)

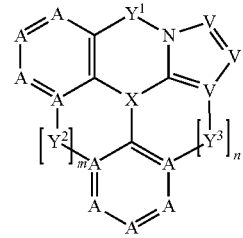

formula (6)

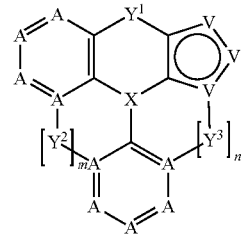

formula (7)

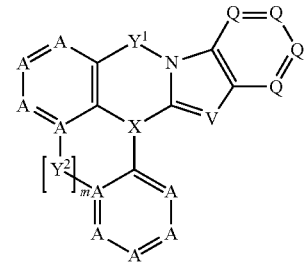

formula (8)

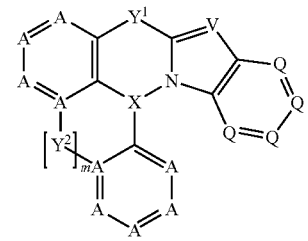

formula (9)

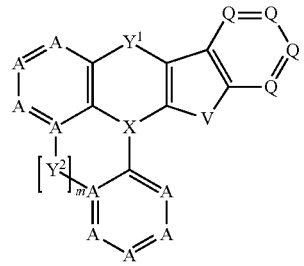

formula (10)

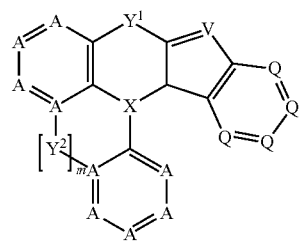

formula (11)

where the symbols and indices used have the above-mentioned meanings and furthermore:

A is on each occurrence, identically or differently, CR or N; or two adjacent groups A together stand for NR, O or S, so that a five-membered ring arises; A here stands for C if a group $Y^2$ or $Y^3$ is bonded to this A.

Furthermore, precisely one of the groups V in formula (7) stands for NR, O or S. Furthermore, V in the formulae (10) and (11) stands for NR, O or S.

In a preferred embodiment of the compounds of the formula (2), two or more compounds of the formulae (5) to (11), which may be identical or different, are correspondingly connected to one another via a group L.

In an embodiment of the invention, m=1 and $Y^2$ then preferably stands for a single bond.

Particularly preferred embodiments of the compounds of the formula (5) to (11) are therefore the compounds of the following formulae (5a) to (11a), formula (5a)
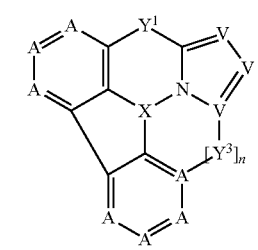

formula (6a)
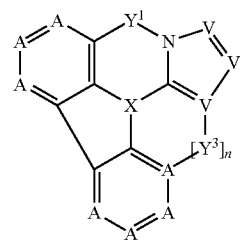

formula (7a)
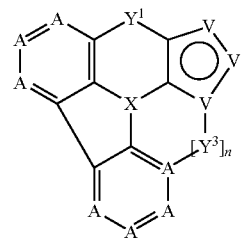

formula (8a)
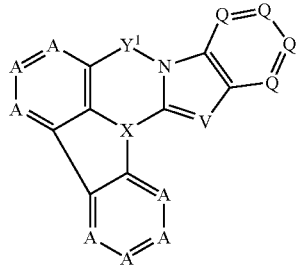

formula (9a)
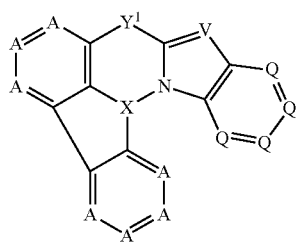

formula (10a)
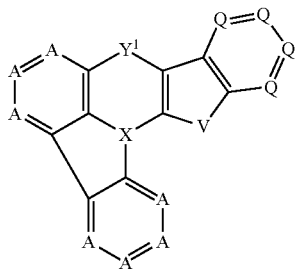

formula (11a)
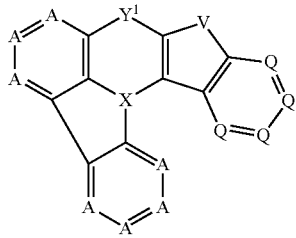

where the symbols and indices used have the above-mentioned meanings.

In a particularly preferred embodiment of the compounds of the formula (2), two or more compounds of the formulae (5a) to (11a), which may be identical or different, are correspondingly connected to one another via a group L.

In a preferred embodiment of the invention, a maximum of two groups Q per ring stand for N, particularly preferably a maximum of one group Q. Very particularly preferably, all groups Q stand for CR.

In a further preferred embodiment of the invention, a maximum of two groups A per ring stand for N, particularly preferably a maximum of one group A. Very particularly preferably, all groups A stand for CR.

Very particularly preferred embodiments of the invention are therefore the following compounds (5b) to (11b), formula (5b)
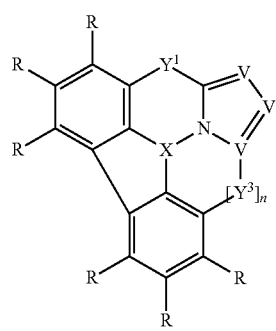

formula (6b)
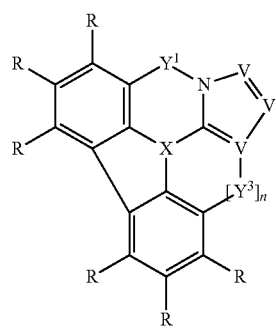

formula (7b)

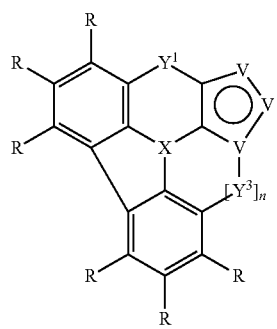

formula (8b)

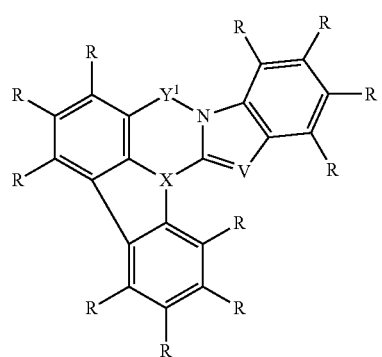

formula (9b)

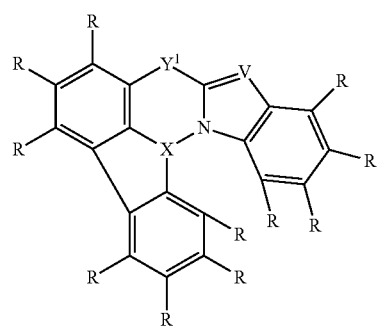

formula (10b)

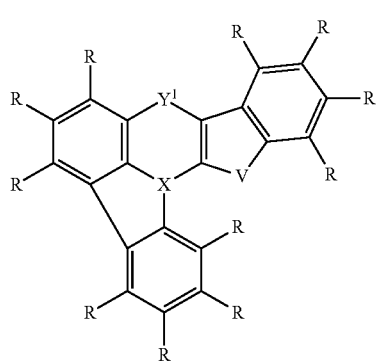

formula (11b)

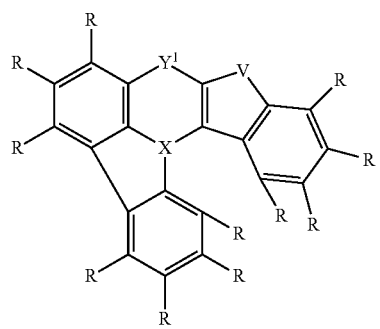

where the symbols and indices used have the above-mentioned meanings.

In a particularly preferred embodiment of the compounds of the formula (2), two or more compounds of the formulae (5b) to (11b), which may be identical or different, are correspondingly connected to one another via a group L.

In a further preferred embodiment of the invention, the indices m and n=0, and the group $Ar^3$ stands for a six-membered aromatic or heteroaromatic ring. Preferred embodiments are therefore the compounds of the following formulae (5c) to (11c), formula (5c)

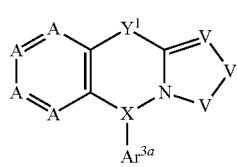

formula (6c)

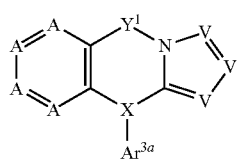

formula (7c)

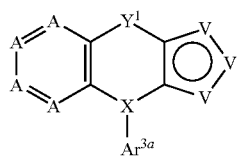

formula (8c)

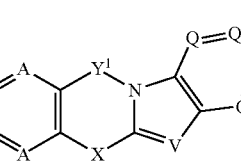

formula (9c)

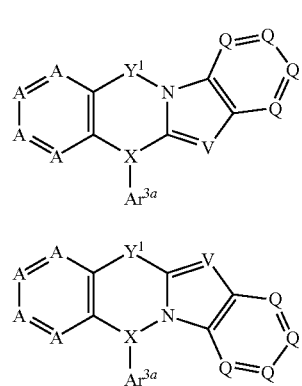

-continued

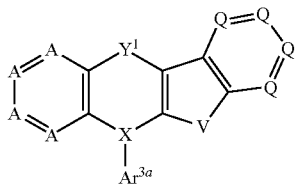
formula (10c)

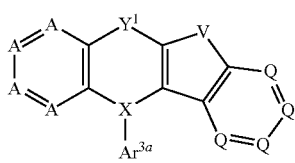
formula (11c)

where the symbols and indices used have the above-mentioned meanings and $Ar^{3a}$ stands for a six-membered aryl ring group or a six-membered heteroaryl ring group, each of which may be substituted by one or more radicals R.

In a further preferred embodiment of the compounds of the formula (2), two or more compounds of the formulae (5c) to (11c), which may be identical or different, are correspondingly connected to one another via a group L.

Preferred groups $Ar^{3a}$ are selected from phenyl, 2-, 3- or 4-pyridyl, 2-, 4- or 5-pyrimidyl, pyrazinyl, 3- or 4-pyridazinyl or 1,3,5-triazin-2-yl, where these groups may each be substituted by one or more radicals R.

Preferred groups $Ar^{3a}$ here are the groups of the following formulae ($Ar^{3a}$-1) to ($Ar^{3a}$-8),

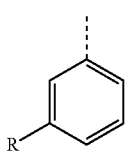
formula ($Ar^{3a}$-1)

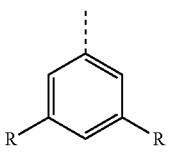
formula ($Ar^{3a}$-2)

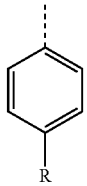
formula ($Ar^{3a}$-3)

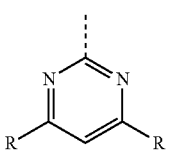
formula ($Ar^{3a}$-4)

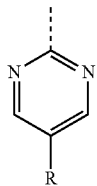
formula ($Ar^{3a}$-5)

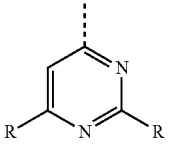
formula ($Ar^{3a}$-6)

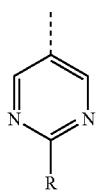
formula ($Ar^{3a}$-7)

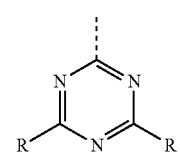
formula ($Ar^{3a}$-8)

where R has the above-mentioned meanings and the dashed bond indicates the bond to X. In a particularly preferred embodiment of the invention, R in formula ($Ar^{3a}$-1) stands for an optionally substituted triazine or pyrimidine group.

In a preferred embodiment of the compounds of the formula (1) to (11) or (5a) to (11c) and in all further embodiments indicated, X stands for nitrogen.

In a further preferred embodiment of the compounds of the formula (1) to (11) or (5a) to (11c) and in all further embodiments indicated, $Y^1$, $Y^2$ and $Y^3$ stands, identically or differently on each occurrence, for a single bond, $C(R^1)_2$ or $N(R^1)$. In particular, $Y^1$ stands on each occurrence, identically or differently, for $C(R^1)_2$ or $N(R^1)$ and $Y^2$ and $Y^3$ stand, identically or differently on each occurrence, for a single bond, $C(R^1)_2$ or $N(R^1)$. Very particularly preferably, $Y^1$ stands for $C(R^1)_2$ and $Y^2$ and $Y^3$ stand, identically or differently on each occurrence, for a single bond or $C(R^1)_2$, where a maximum of one of the two groups $Y^2$ and $Y^3$ stands for a single bond.

If the compounds of the formula (5b) to (11b) are substituted by radicals R other than hydrogen or deuterium, these radicals R are then preferably each bonded to the rings which correspond to $Ar^2$ and $Ar^3$ in the para-position to the group X. Preference is therefore given to the compounds of the following formulae (5d) to (11d), formula (5d)
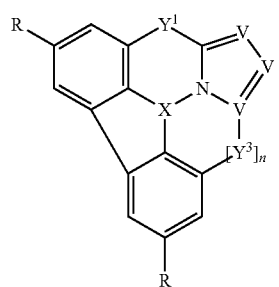
formula (6d)
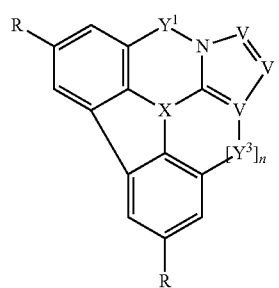
formula (7d)
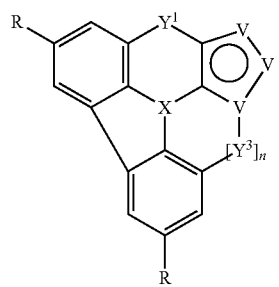
formula (8d)
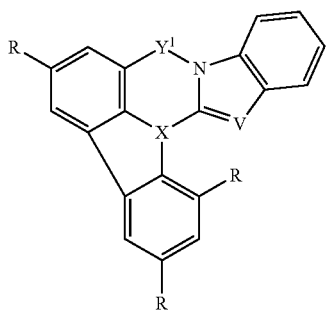
formula (9d)
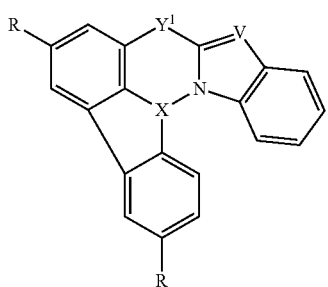
formula (10d)
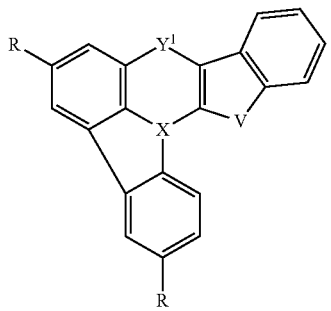
formula (11d)
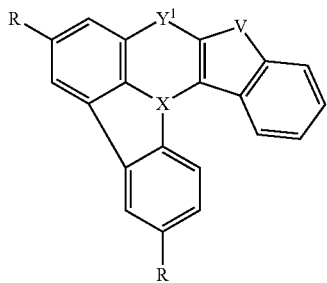
where the symbols and indices used have the above-mentioned meanings.
Preferred structures of the five-membered heterocyclic ring in the formulae (5), (5a), (5b), (5c) and (5d) are the following structures of the formulae $(Ar^1$-1) to $(Ar^1$-6),
formula $(Ar^1$-1)
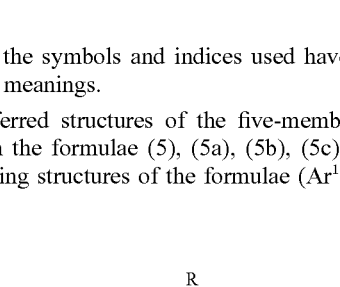
formula $(Ar^1$-2)
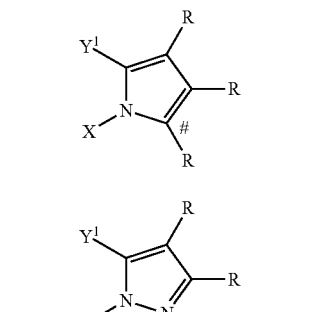
formula $(Ar^1$-3)
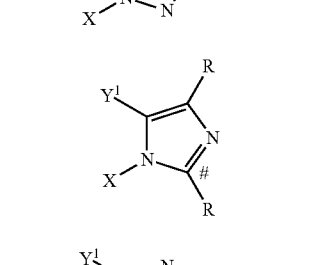
formula $(Ar^1$-4)
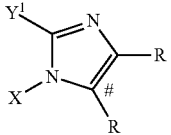
formula $(Ar^1$-5)
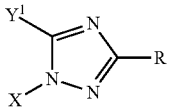

-continued

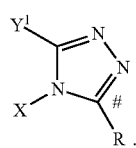
formula (Ar¹-6)

The bond from this ring to X and to $Y^1$ is also drawn in in each case here. The position denoted by # indicates the position of a possible bond to $Y^3$, where in this case no radical R is bonded to the carbon atom.

Preferred structures of the five-membered heterocyclic ring in the formulae (6), (6a), (6b), (6c) and (6d) are the following structures of the formulae (Ar¹-7) to (Ar¹-12),

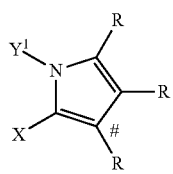
formula (Ar¹-7)

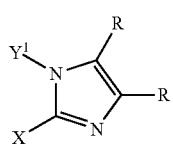
formula (Ar¹-8)

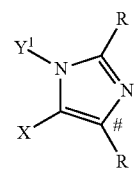
formula (Ar¹-9)

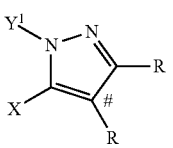
formula (Ar¹-10)

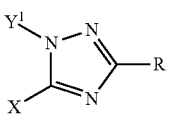
formula (Ar¹-11)

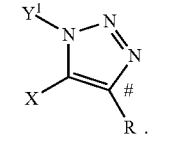
formula (Ar¹-12)

The bond from this ring to X and to $Y^1$ is also drawn in in each case here. The position denoted by # indicates the position of a possible bond to $Y^3$, where in this case no radical R is bonded to the carbon atom.

Preferred structures of the five-membered heterocyclic ring in the formulae (7), (7a), (7b), (7c) and (7d) are the following structures of the formulae (Ar¹-13) to (Ar¹-27),

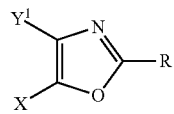
formula (Ar¹-13)

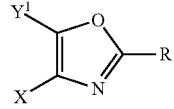
formula (Ar¹-14)

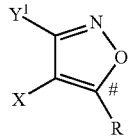
formula (Ar¹-15)

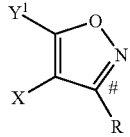
formula (Ar¹-16)

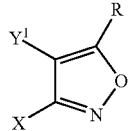
formula (Ar¹-17)

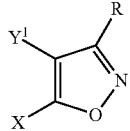
formula (Ar¹-18)

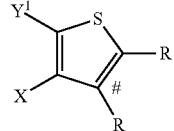
formula (Ar¹-19)

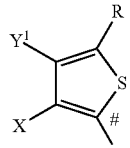
formula (Ar¹-20)

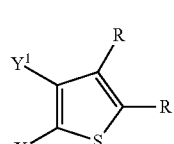
formula (Ar¹-21)

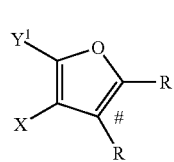
formula (Ar¹-22)

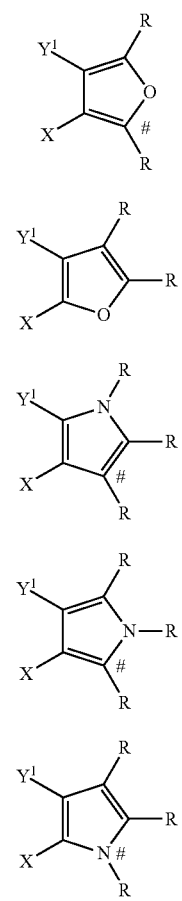

formula (Ar¹-23)

formula (Ar¹-24)

formula (Ar¹-25)

formula (Ar¹-26)

formula (Ar¹-27)

The bond from this ring to X and to Y¹ is also drawn in in each case here. The position denoted by # indicates the position of a possible bond to Y³, where in this case no radical R is bonded to the carbon atom.

In a further preferred embodiment of the invention, L is a divalent or polyvalent straight-chain alkylene or alkylidene group having 1 to 10 C atoms or a branched or cyclic alkylene or alkylidene group having 3 to 10 C atoms, which may be substituted by in each case one or more radicals $R^2$, where one or more H atoms may be replaced by D or F, or an at least divalent aromatic or heteroaromatic ring system having 5 to 24 aromatic ring atoms, which may be substituted by one or more radicals $R^2$, or L is a chemical bond.

Possible substituents R in the compounds according to the invention are various groups, depending on the use of the compounds. In a preferred embodiment of the compound of the formula (1) to (11) or (5a) to (11d), R is selected on each occurrence, identically or differently, from the group consisting of H, D, F, CN, N(Ar)$_2$, C(=O)Ar, P(=O)(Ar)$_2$, a straight-chain alkyl group having 1 to 10 C atoms or a branched or cyclic alkyl group having 3 to 10 C atoms or an alkenyl group having 2 to 10 C atoms, each of which may be substituted by one or more radicals $R^2$, where one or more non-adjacent CH$_2$ groups may be replaced by O or S and where one or more H atoms may be replaced by D or F, an aromatic or heteroaromatic ring system having 6 to 30 aromatic ring atoms, which may in each case be substituted by one or more radicals $R^2$, where two or more adjacent substituents R may optionally form a monocyclic or polycyclic, aliphatic, aromatic or heteroaromatic ring system, which may be substituted by one or more radicals $R^2$. In a particularly preferred embodiment of the compound of the formula (1) to (11) or (5a) to (11d), R is selected on each occurrence, identically or differently, from the group consisting of H, D, N(Ar)$_2$, a straight-chain alkyl group having 1 to 4 C atoms or a branched alkyl group having 3 or 4 C atoms, each of which may be substituted by one or more radicals $R^1$, where one or more H atoms may be replaced by D, or an aromatic or heteroaromatic ring system having 6 to 18 aromatic ring atoms, which may in each case be substituted by one or more radicals $R^2$.

Substituents $R^1$ which are bonded in $Y^1$, $Y^2$ and/or $Y^3$ are preferably selected from the group consisting of H, alkyl groups having 1 to 10 C atoms or aromatic or heteroaromatic ring systems having 5 to 20 aromatic ring atoms, each of which may be substituted by one or more radicals $R^2$. Two radicals $R^1$ here which are bonded in the same group $Y^1$, $Y^2$ or $Y^3$ may also form a ring system with one another and thus form a spiro system. If $Y^1$, $Y^2$ or $Y^3$ stands for a group N(R$^1$), $R^1$ particularly preferably stands for an aromatic or heteroaromatic ring system, which may be substituted by one or more radicals $R^2$. If $Y^1$, $Y^2$ or $Y^3$ stands for a group C(R$^1$)$_2$, $R^1$ particularly preferably stands, identically or differently on each occurrence, for H, an alkyl group having 1 to 10 C atoms or an aromatic or heteroaromatic ring system having 5 to 20 aromatic ring atoms, each of which may be substituted by one or more radicals $R^2$. Two radicals $R^1$ here which are bonded to the same carbon atom may also form a ring system with one another and thus form an aromatic or aliphatic spiro system.

For compounds which are processed by vacuum evaporation, the alkyl groups in the radicals R or $R^1$ preferably have not more than four C atoms, particularly preferably not more than one C atom. For compounds which are processed from solution, particularly suitable compounds are also those which are substituted by alkyl groups having up to 10 C atoms or which are substituted by oligoarylene groups, for example ortho-, meta-, para- or branched terphenyl groups or quaterphenyl groups or ortho-, meta- or para-biphenyl groups.

If the compound according to the invention is employed as matrix material for a phosphorescent emitter or as electron-transport material or as hole-blocking material, Ar$^2$ and/or Ar$^3$ is preferably an electron-deficient heteroaromatic radical and/or at least one substituent R, $R^1$ and/or $R^2$, preferably R, is an electron-deficient group, in particular selected from structures of the following formulae (12) to (15),

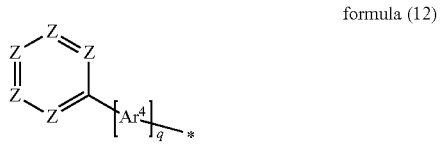

formula (12)

formula (13)

-continued

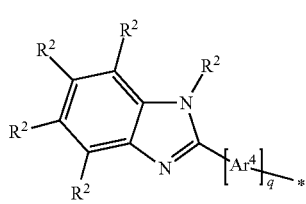
formula (14)

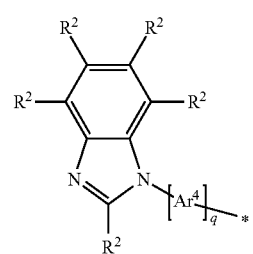
formula (15)

and/or at least one group L preferably stands for a group of the following formulae (16) to (18).

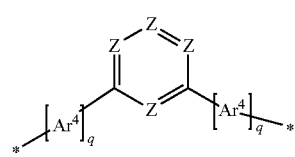
formula (16)

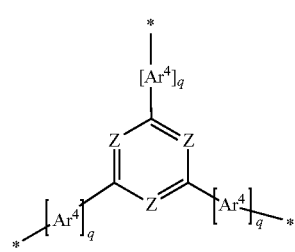
formula (17)

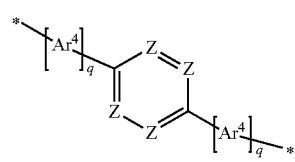
formula (18)

where $R^2$ has the above-mentioned meaning, * indicates the position of the bond of the group of the formula (12) to (18) and furthermore:

Z is on each occurrence, identically or differently, $CR^2$ or N, with the proviso that one group Z, two groups Z or three groups Z stand for N;

$Ar^4$ is, identically or differently on each occurrence, a divalent aryl or heteroaryl group having 5 to 18 C atoms, which may be substituted by one or more radicals $R^2$;

q is on each occurrence, identically or differently, 0, 1, 2 or 3.

An electron-deficient heteroaromatic radical here is taken to mean a five-membered heteroaromatic ring group having at least two heteroatoms or a six-membered heteroaromatic ring group having at least one heteroatom.

In a particularly preferred embodiment of the invention, at least one substituent R stands for a group of the above-mentioned formula (12) and/or at least the group L stands for a group of the above-mentioned formulae (16) to (18), where in each case two or three symbols Z stand for N and the other symbols Z stand for $CR^2$. Particularly preferred groups R are therefore the groups of the following formulae (19) to (25), and particularly preferred groups L are therefore the groups of the following formulae (26) to (33),

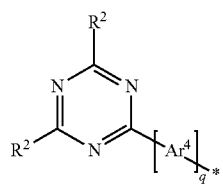
formula (19)

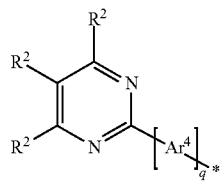
formula (20)

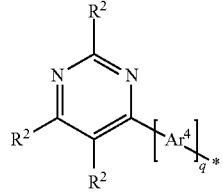
formula (21)

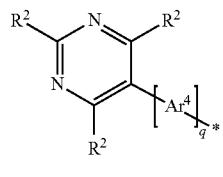
formula (22)

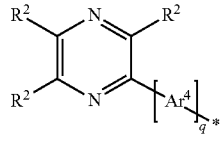
formula (23)

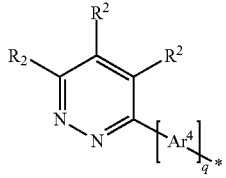
formula (24)

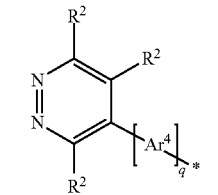
formula (25)

formula (26)
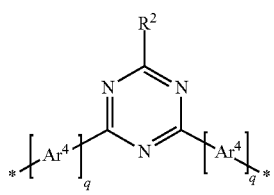

formula (27)
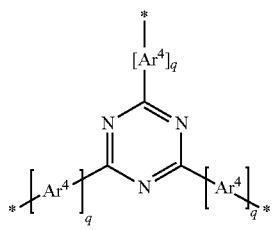

formula (28)
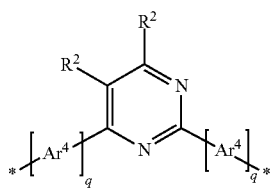

formula (29)
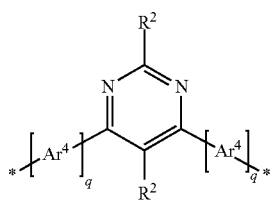

formula (30)
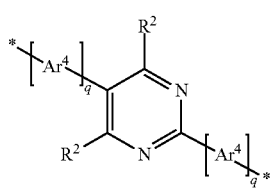

formula (31)
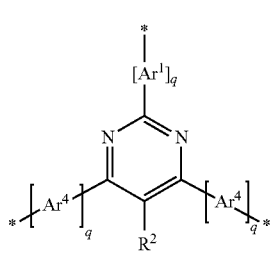

formula (32)
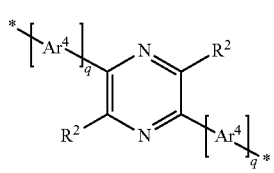

formula (33)
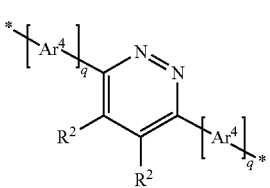

where the symbols and indices used have the above-mentioned meanings.

If R stands for a group of the formula (19), $R^2$ in this group then preferably stands for an aromatic or heteroaromatic ring system having 5 to 24 aromatic ring atoms, which may be substituted by one or more radicals $R^3$, in particular for phenyl, ortho-, meta- or para-biphenyl, ortho-, meta-, para- or branched terphenyl or ortho-, meta-, para- or branched quaterphenyl.

If R stands for a group of the formula (20) to (33), $R^2$ in these groups then preferably stands, identically or differently on each occurrence, for H, D or an aromatic or heteroaromatic ring system having 5 to 24 aromatic ring atoms, which may be substituted by one or more radicals $R^3$, in particular for phenyl, ortho-, meta- or para-biphenyl, ortho-, meta-, para- or branched terphenyl or ortho-, meta-, para- or branched quaterphenyl.

If the compound according to the invention is employed as matrix material for a phosphorescent emitter or as hole-transport material, at least one substituent R or $R^1$, preferably R, is preferably selected from the group consisting of —NAr$_2$, triarylamine derivatives, carbazole derivatives, indenocarbazole derivatives, indolocarbazole derivatives, azacarbazole derivatives, indole derivatives, furan derivatives, benzofuran derivatives, dibenzofuran derivatives, thiophene derivatives, benzothiophene derivatives or dibenzothiophene derivatives, each of which may be substituted by one or more radicals $R^2$. These groups are preferably selected from the groups of the following formulae (34) to (47), formula (34)
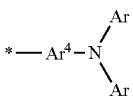

formula (35)
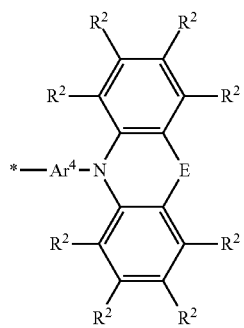

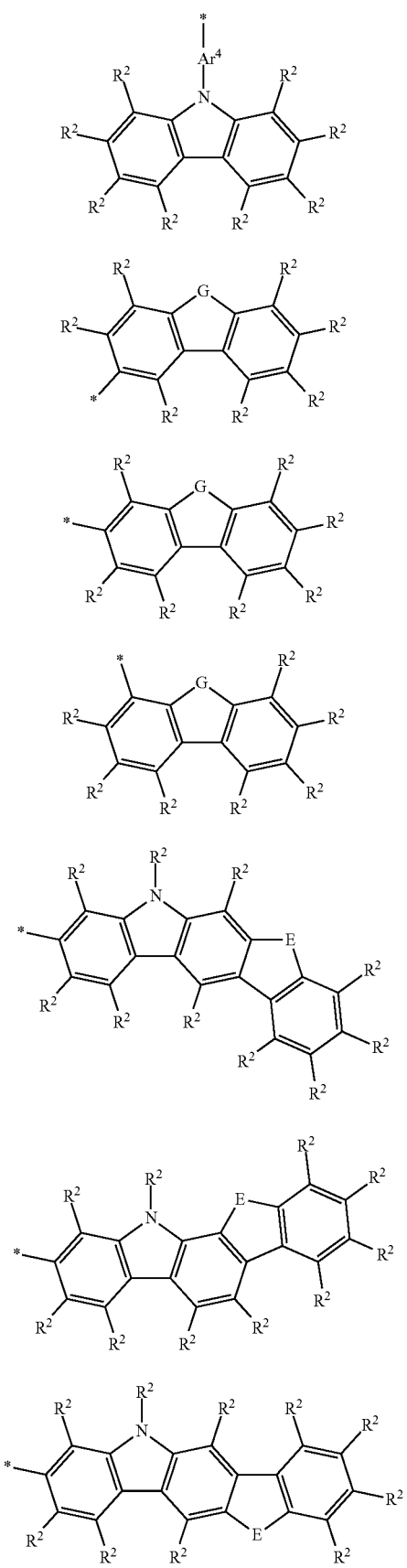

formula (36)

formula (37)

formula (38)

formula (39)

formula (40)

formula (41)

formula (42)

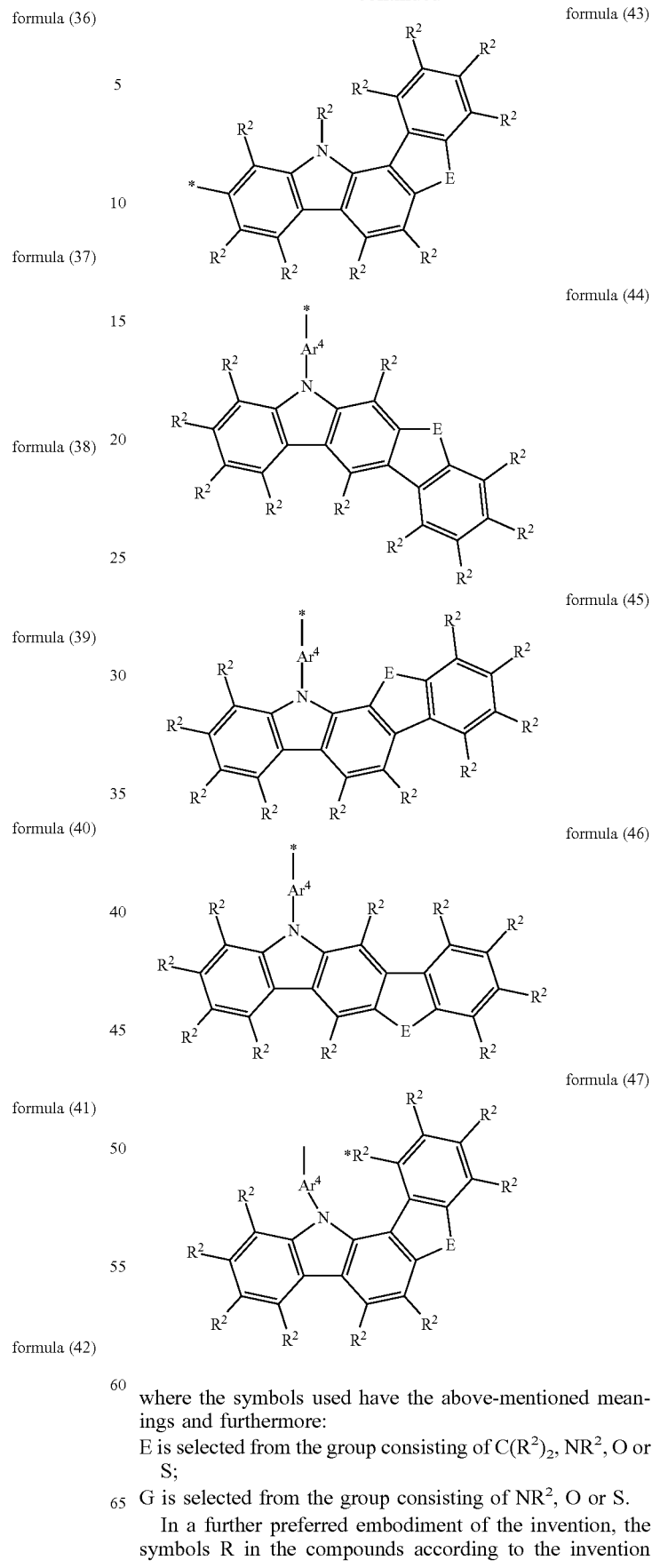

formula (43)

formula (44)

formula (45)

formula (46)

formula (47)

where the symbols used have the above-mentioned meanings and furthermore:

E is selected from the group consisting of $C(R^2)_2$, $NR^2$, O or S;

G is selected from the group consisting of $NR^2$, O or S.

In a further preferred embodiment of the invention, the symbols R in the compounds according to the invention which do not stand for a group of the above-mentioned formulae (12) to (47) stand for H or D.

Preference is furthermore also given to compounds which simultaneously contain both electron-transporting substituents R or $R^1$ selected from the above-mentioned formulae (12) to (33) and also hole-transporting substituents R or $R^1$ selected from the above-mentioned formulae (34) to (47).

In a further preferred embodiment of the invention, the index p=2 or 3, particularly preferably 2.

In a further preferred embodiment of the invention, the index n=0.

In a further preferred embodiment, one or two groups R or $R^1$, preferably R, stand for a group of the above-mentioned formulae (12) to (47), particularly preferably precisely one group R, and the other groups R stand for H or D.

The above-mentioned embodiments of the invention can be combined with one another as desired. In particular, the above-mentioned general formulae (1) to (11) and (5a) to (11d) can be combined as desired with the formulae ($Ar^1$-1) to ($Ar^1$-27) and with the above-mentioned preferred embodiments for X, $Y^1$, $Y^2$, $Y^3$, R, $R^1$, $R^2$, m and n. In a preferred embodiment of the invention, the above-mentioned preferences occur simultaneously.

The corresponding situation applies to the compounds of the formula (2). Particularly preferred embodiments of the compounds of the formula (2) are correspondingly compounds of the above-mentioned formulae (5a) to (11d) in which in each case two or more of these units are bridged to one another by a divalent group L, which is in each case bonded in the para-position to X instead of the substituent R, where furthermore the above-mentioned preferences for X, $Y^1$, $Y^2$, $Y^3$, R, $R^1$, $R^2$, L, m, n and p apply.

Examples of preferred compounds in accordance with the above-mentioned embodiments or compounds as can preferably be employed in organic electronic devices are the following compounds.

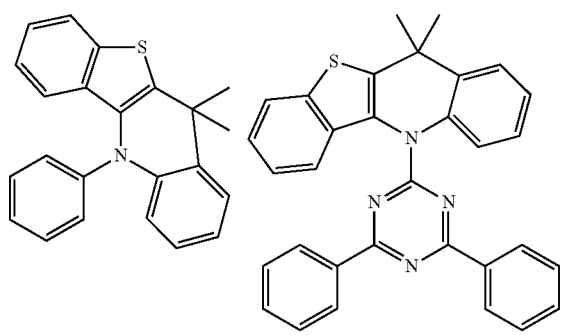

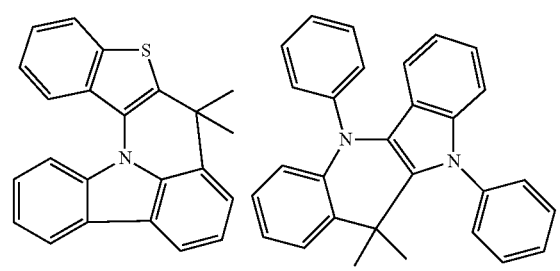

-continued

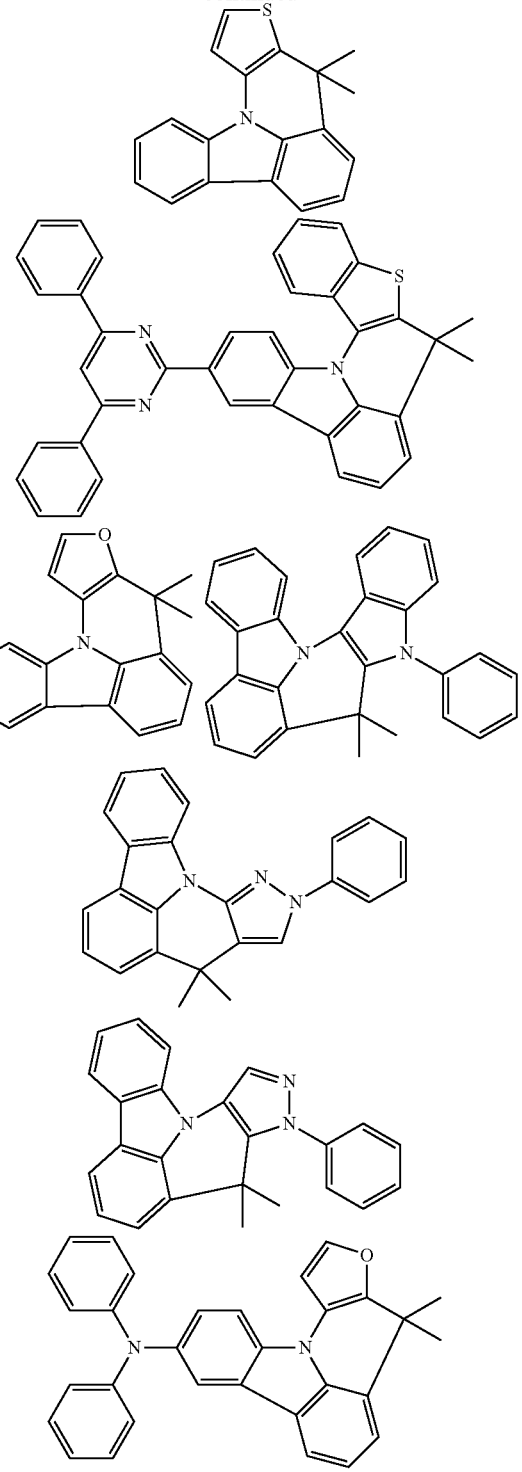

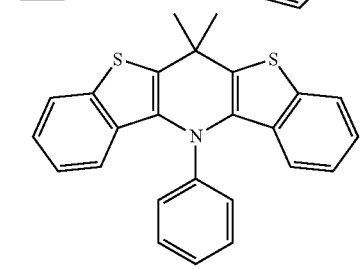

-continued
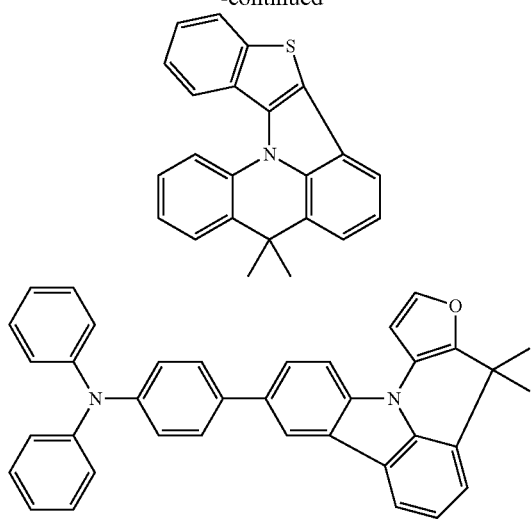
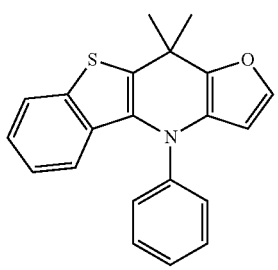
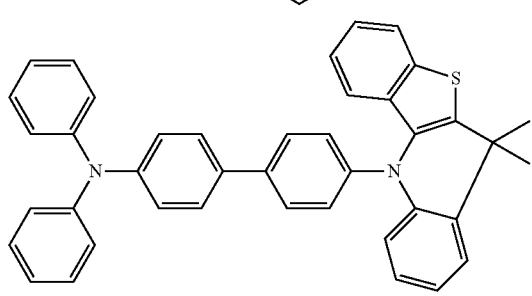
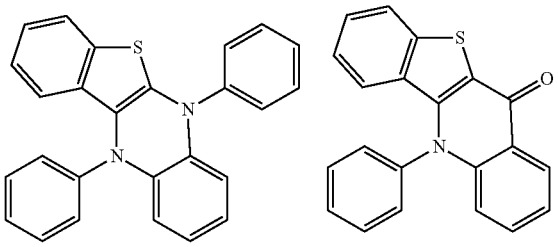
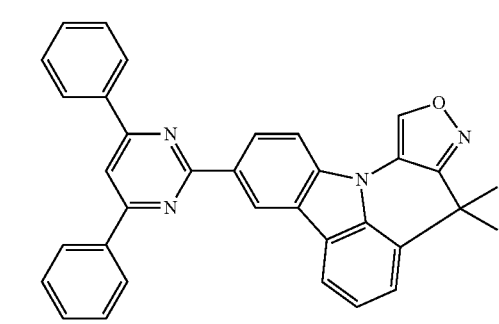
-continued
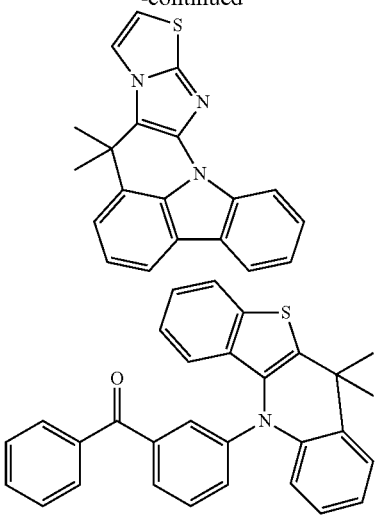
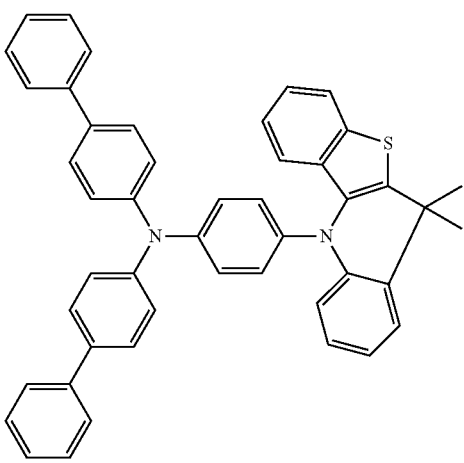
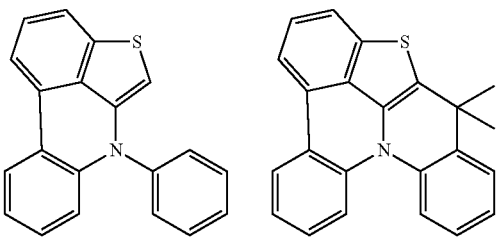
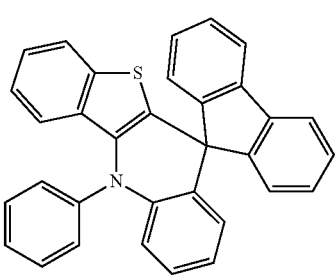

31
-continued
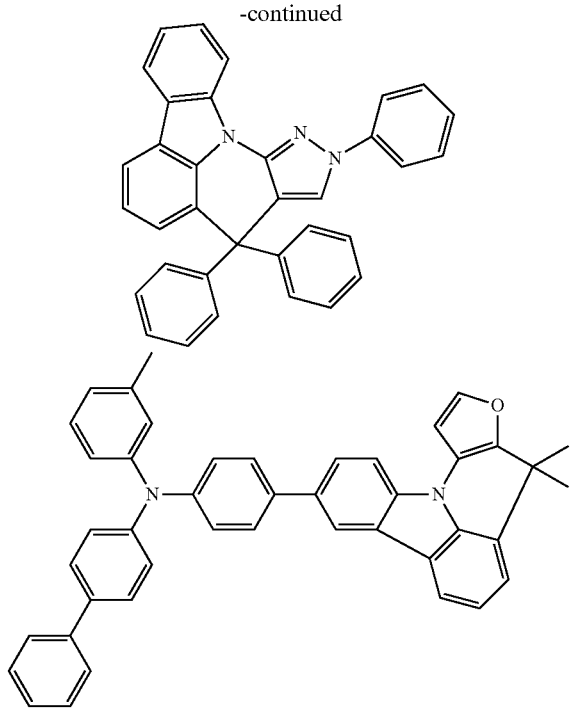
32
-continued
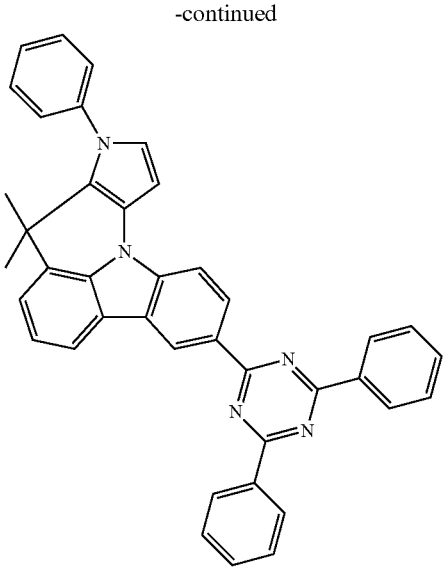
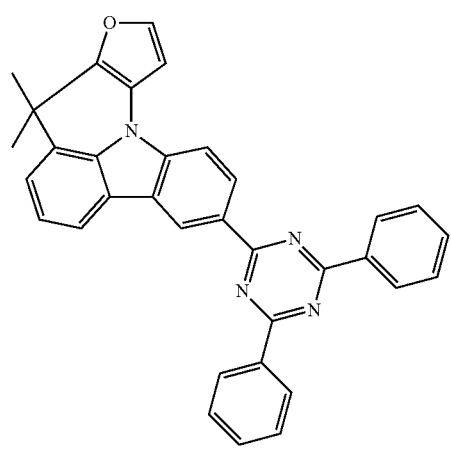
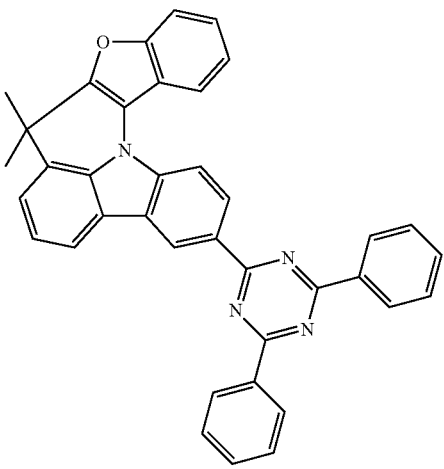
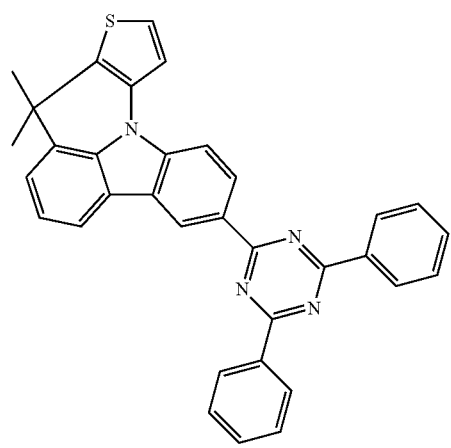
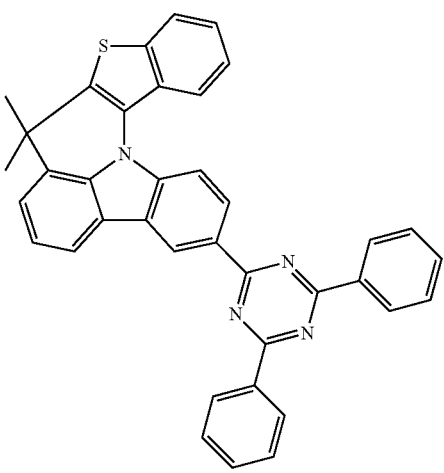

33
-continued
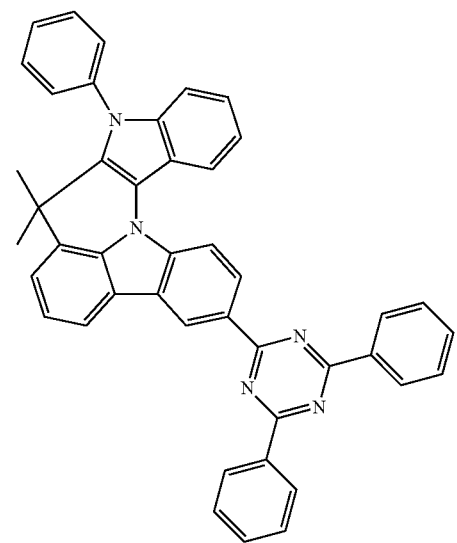
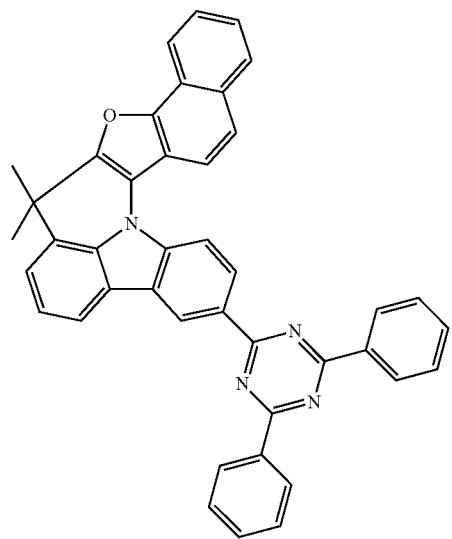
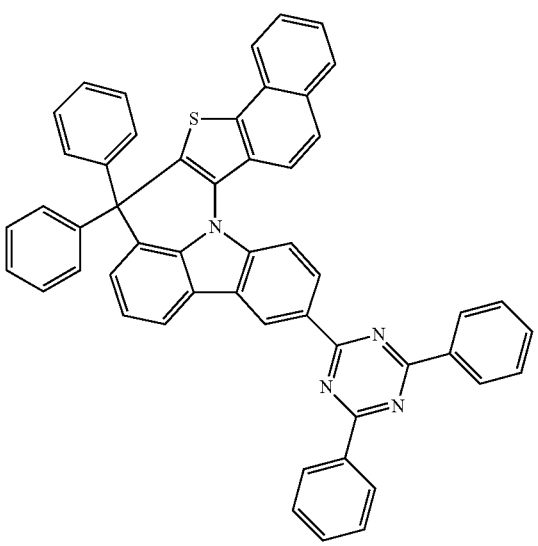
34
-continued
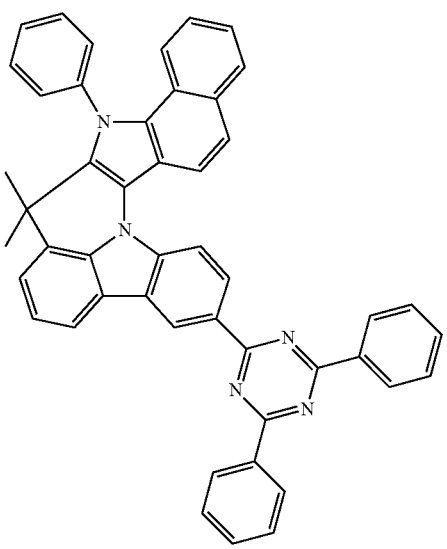
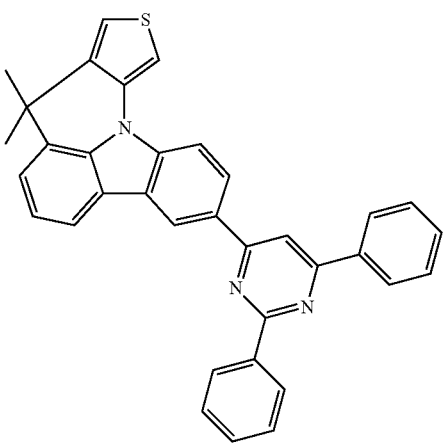
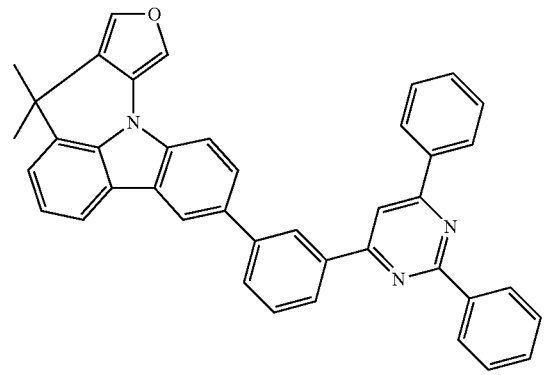

-continued
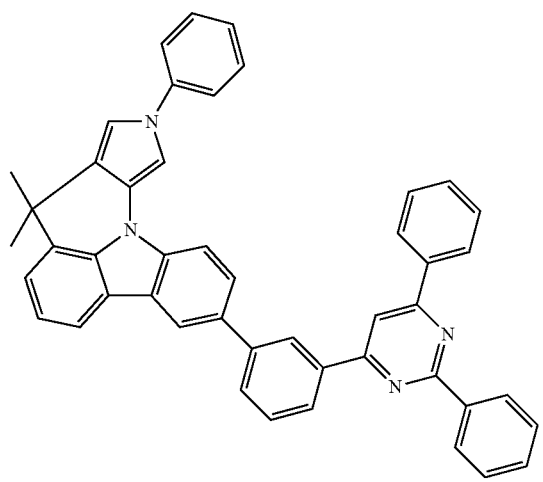
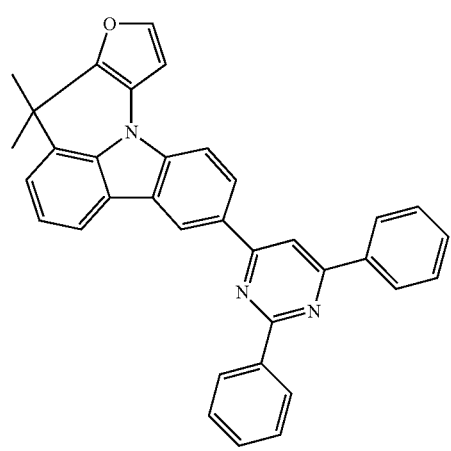
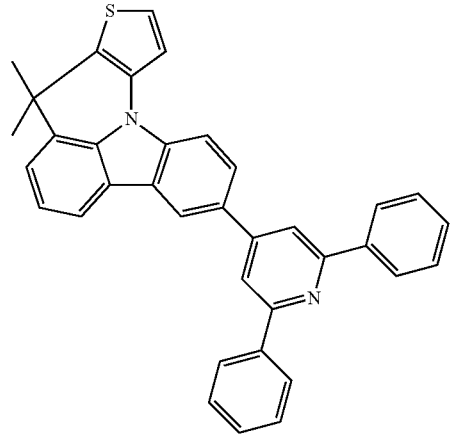
-continued
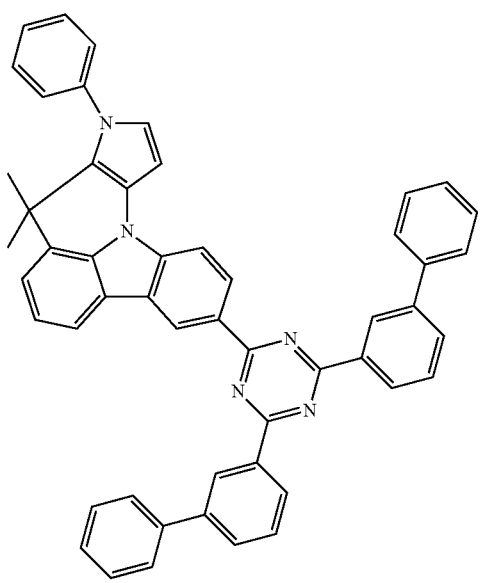
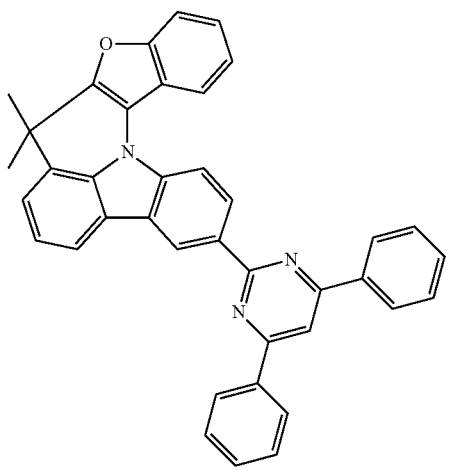
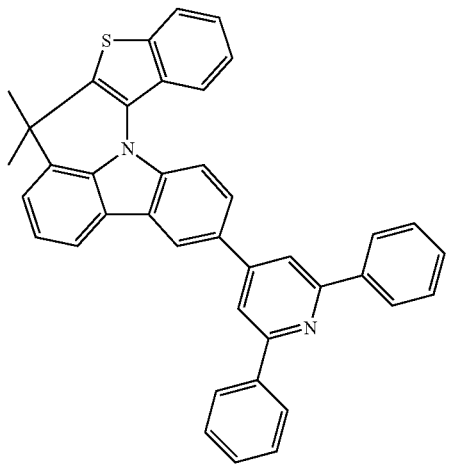

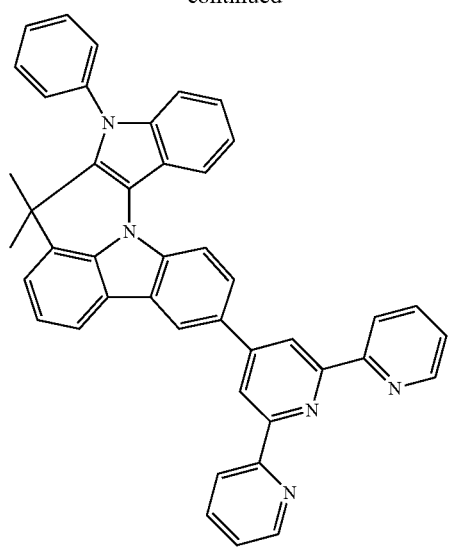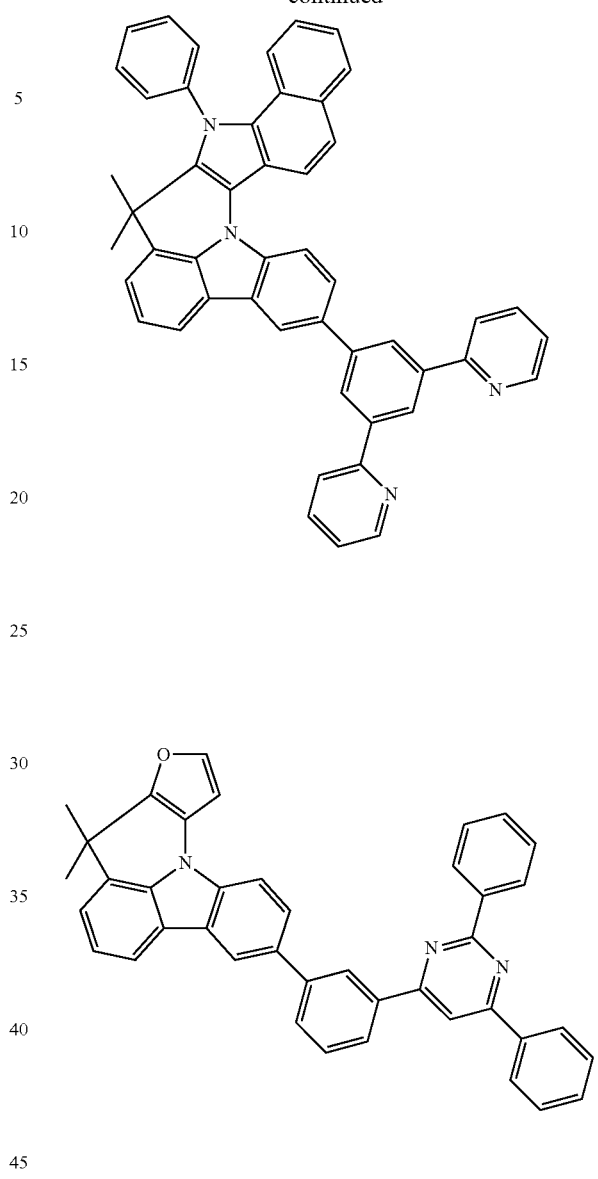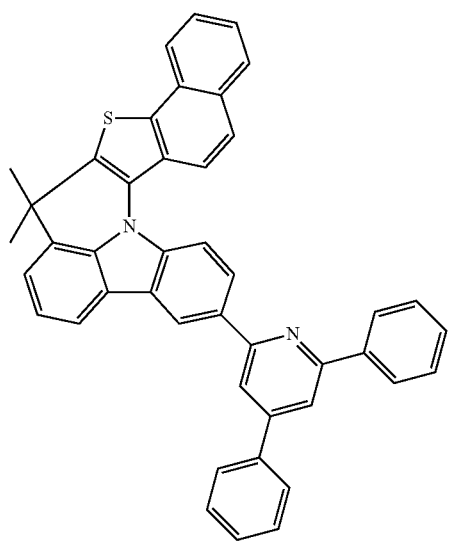

-continued
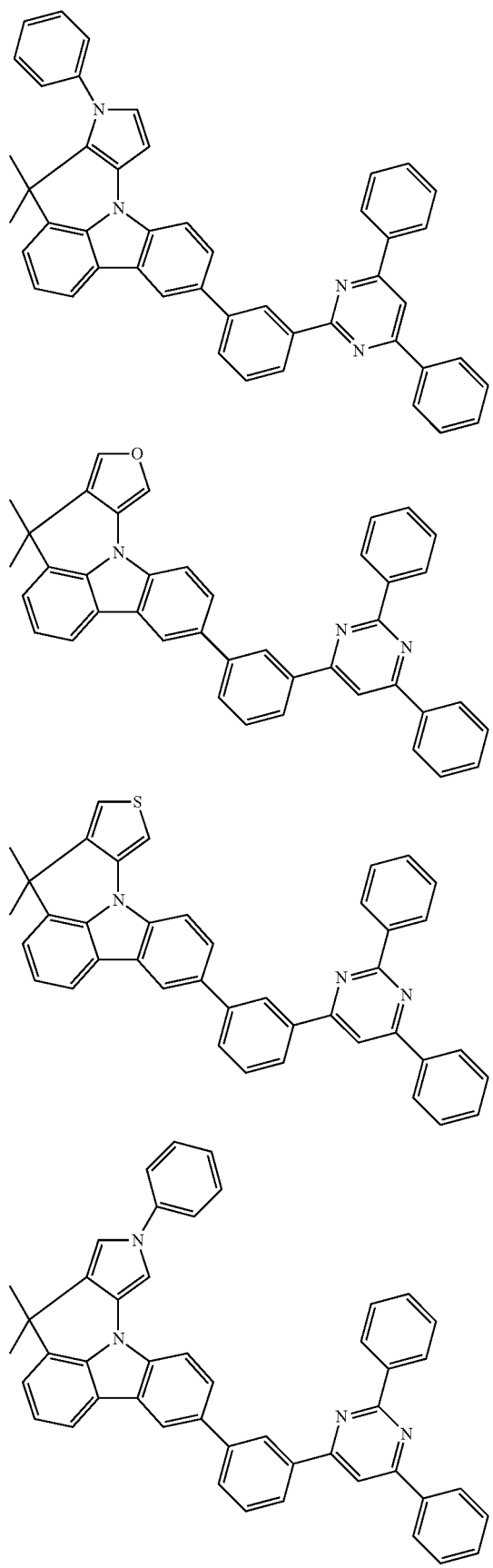
-continued
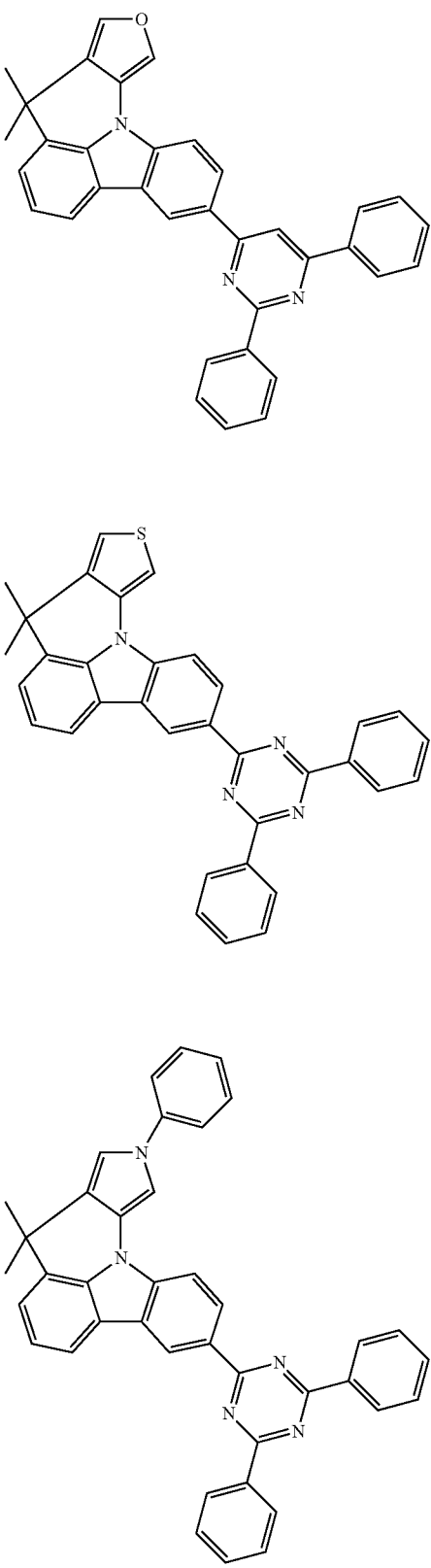

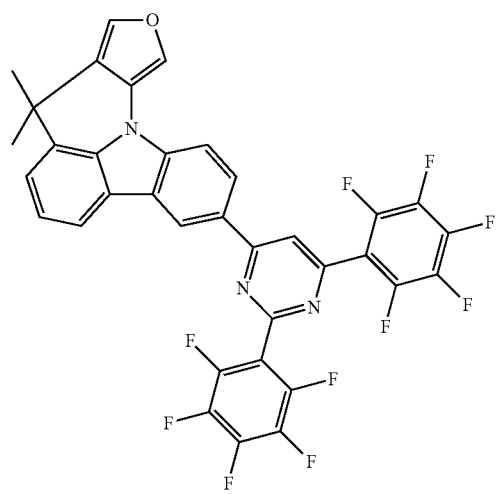
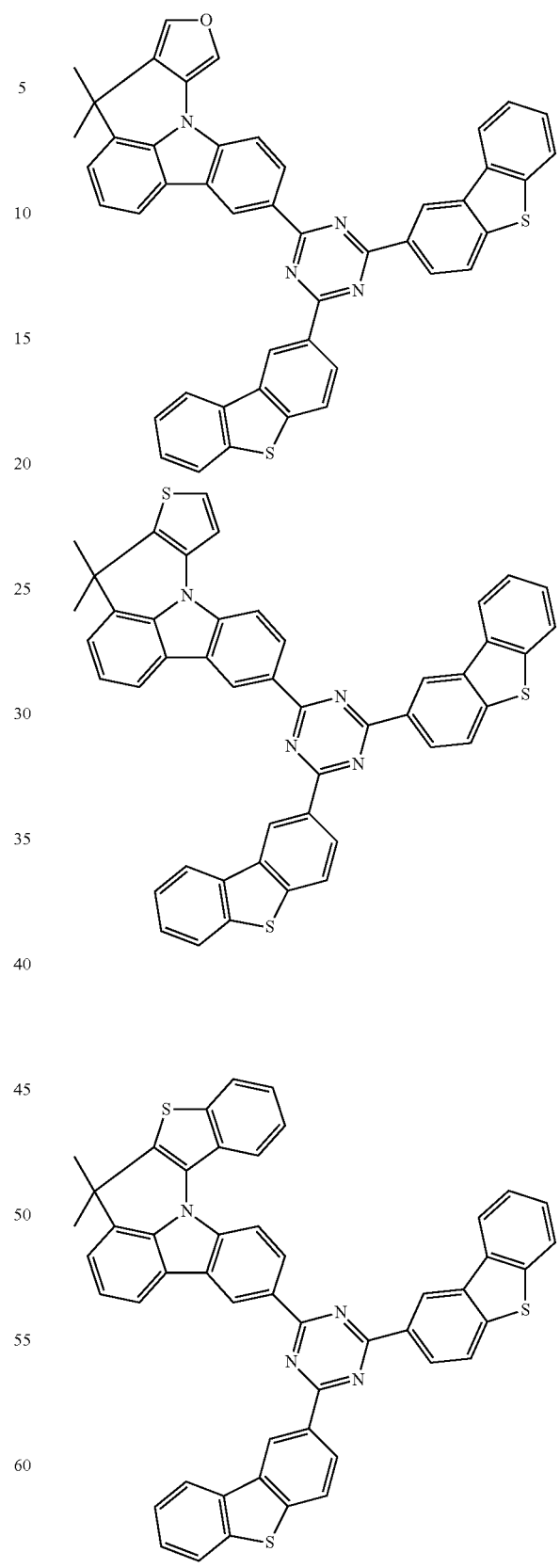

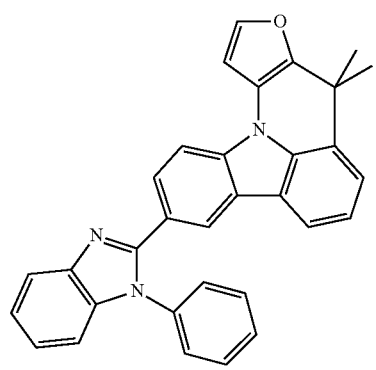
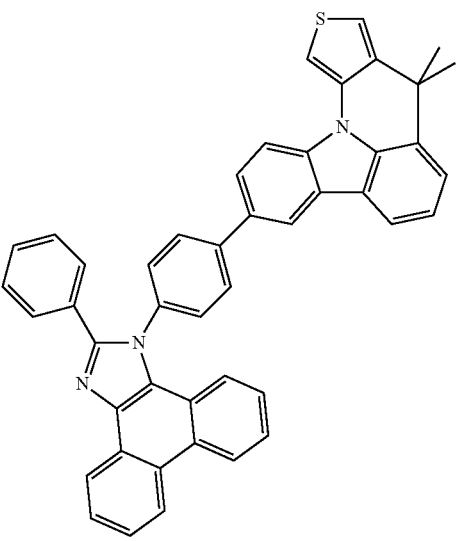
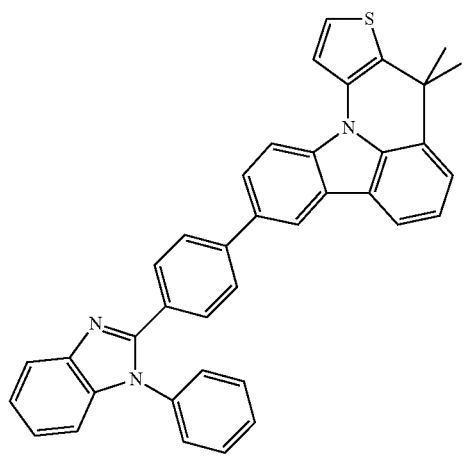
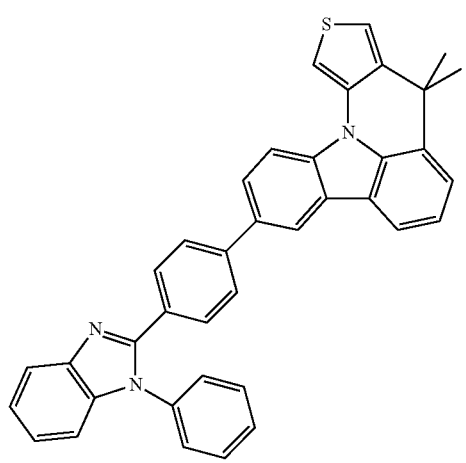

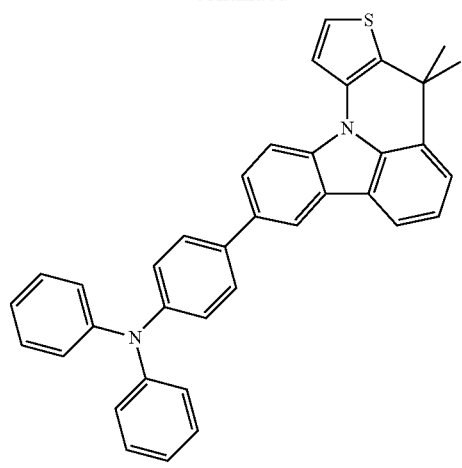 [SMILES: CC1(C)c2ccccc2N(c2ccccc2)c2ccc(-c3ccc4c(c3)c3cccc5c3n4-c3ccsc3C5(C)C)cc21]
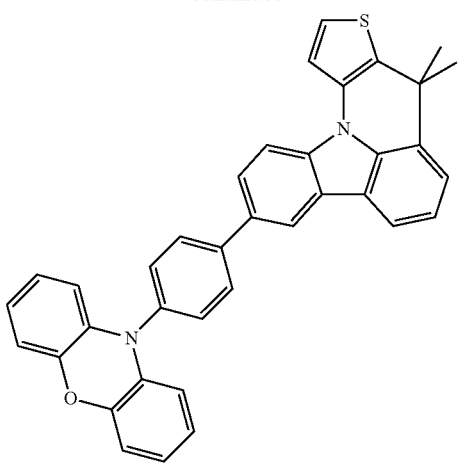

47
-continued
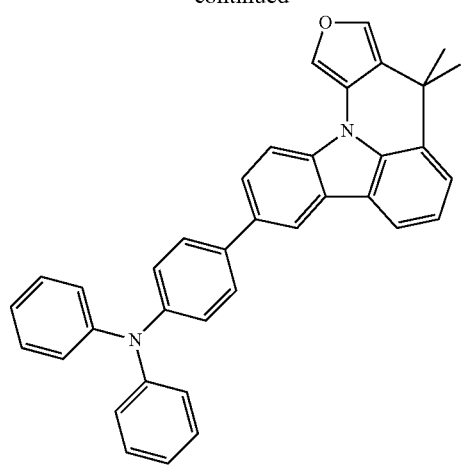
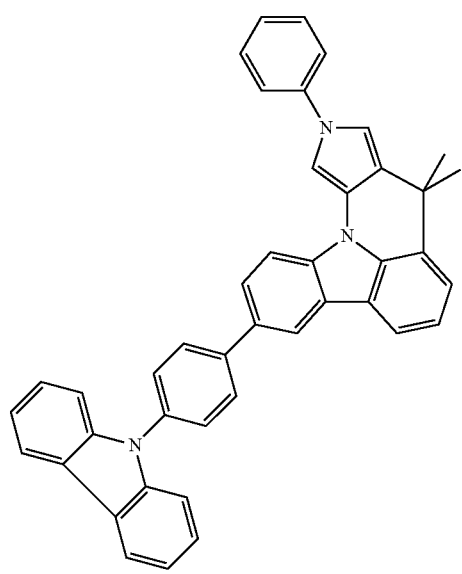
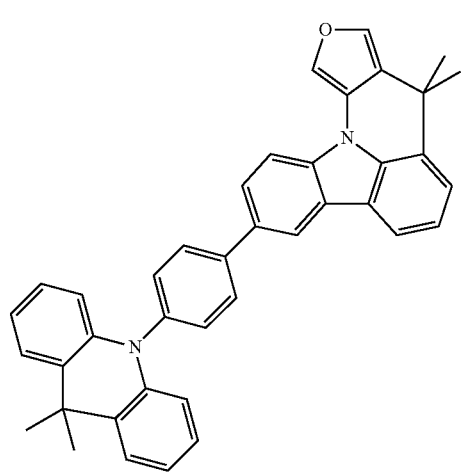
48
-continued
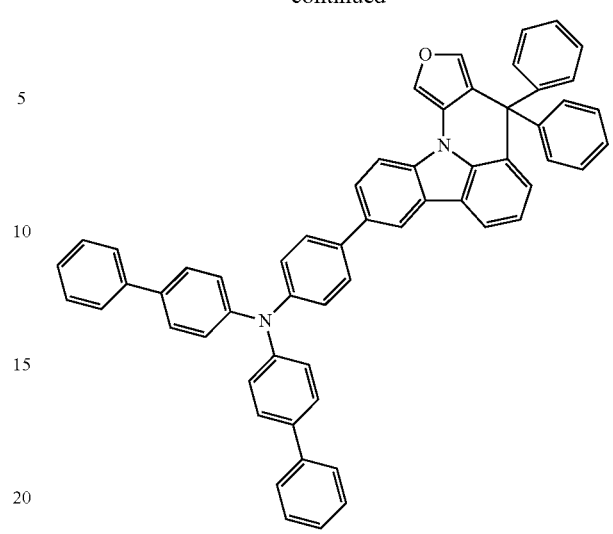
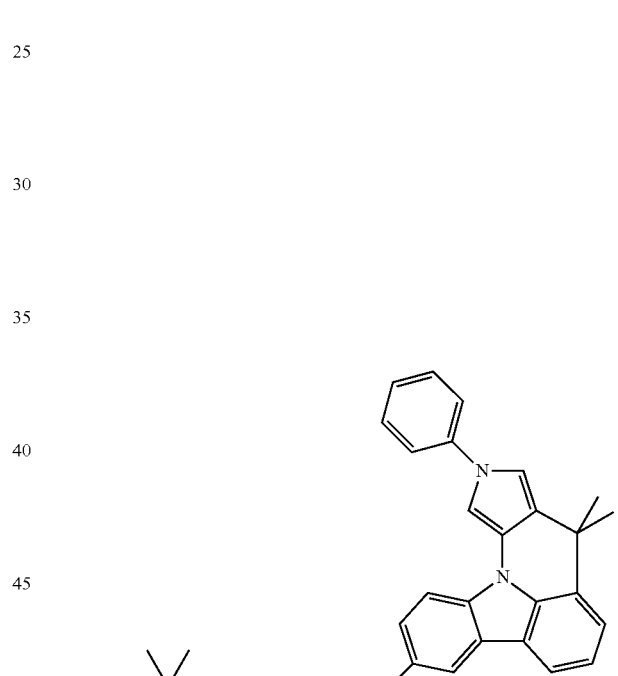

49
-continued
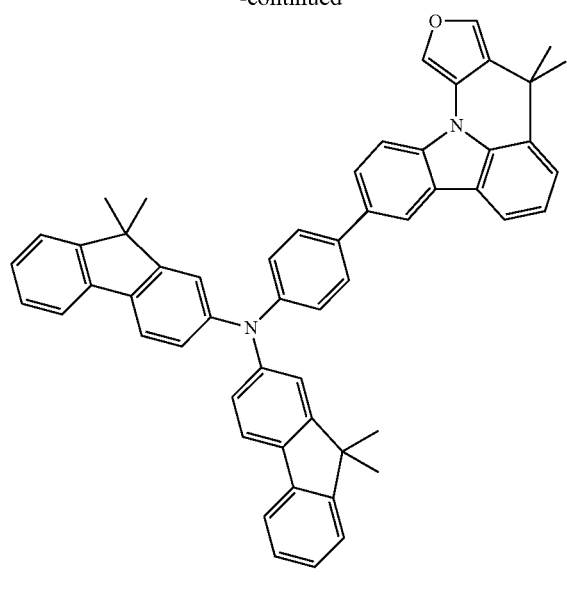
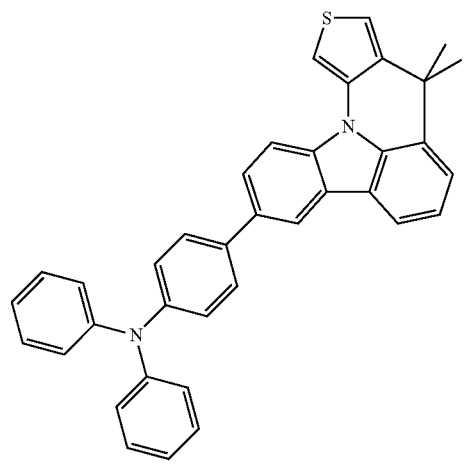
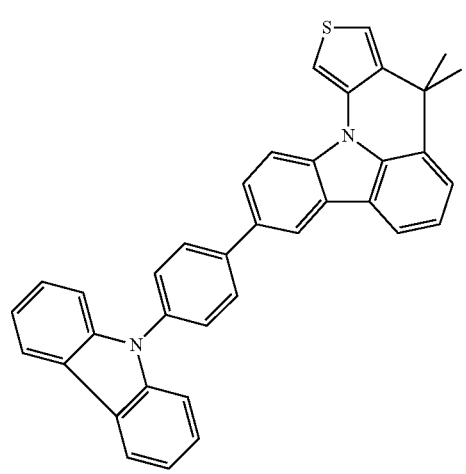
50
-continued
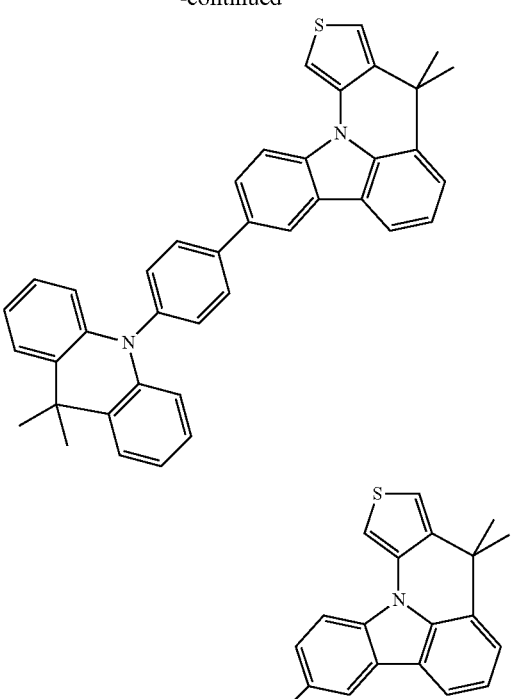
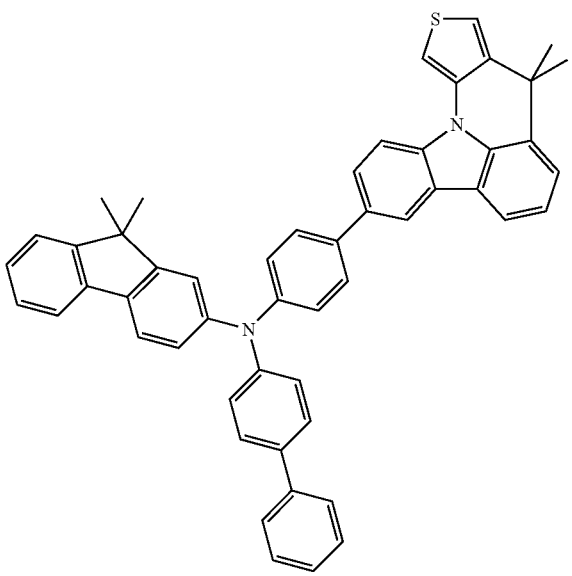

51
-continued
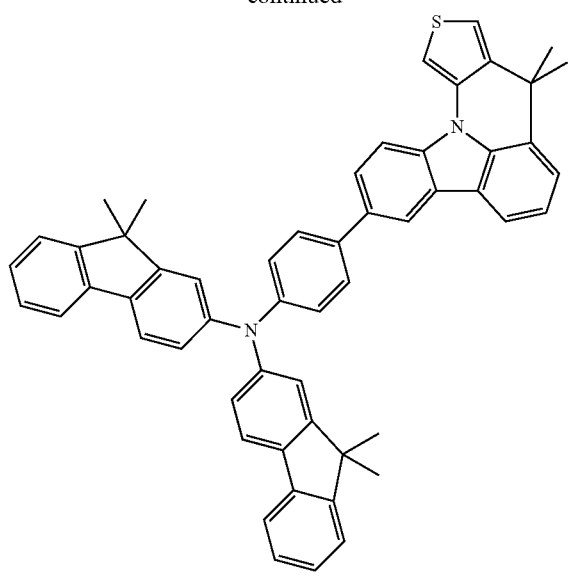
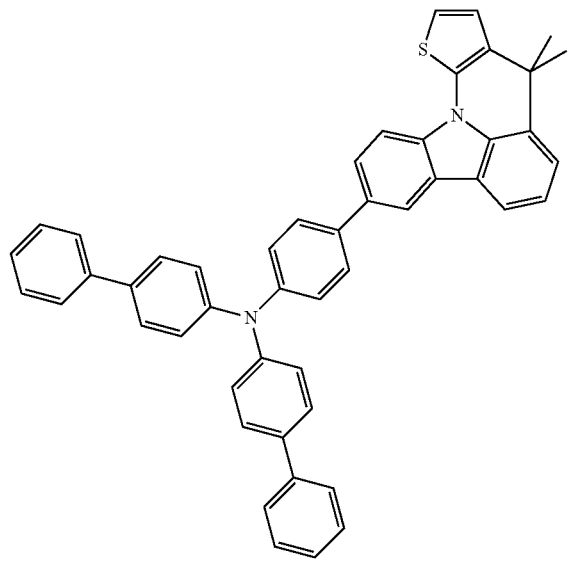
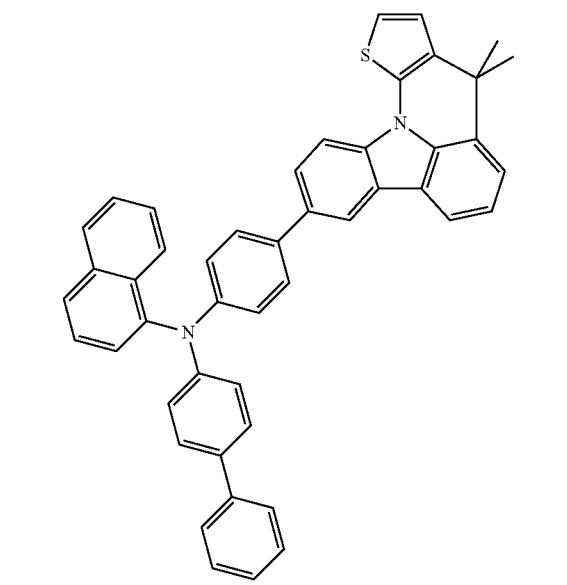
52
-continued
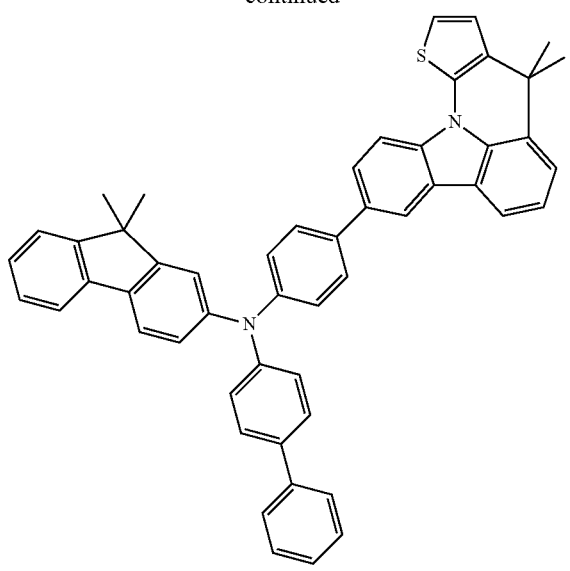
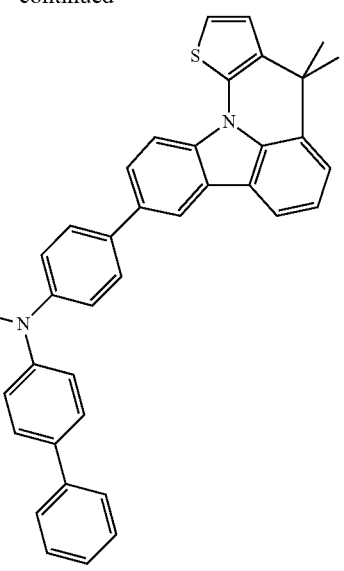
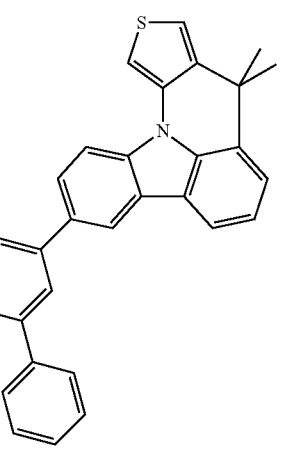

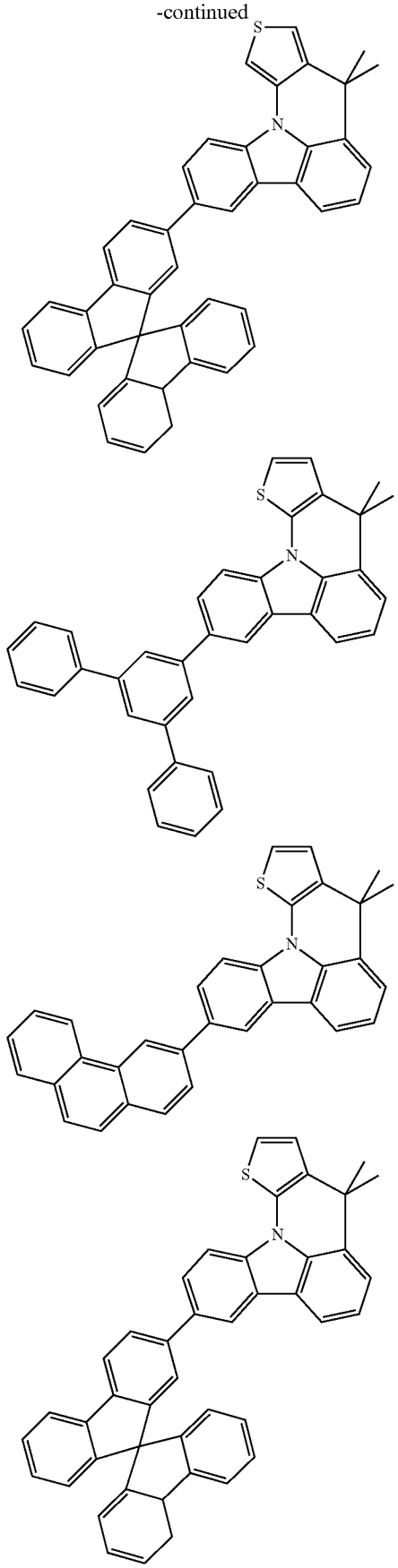
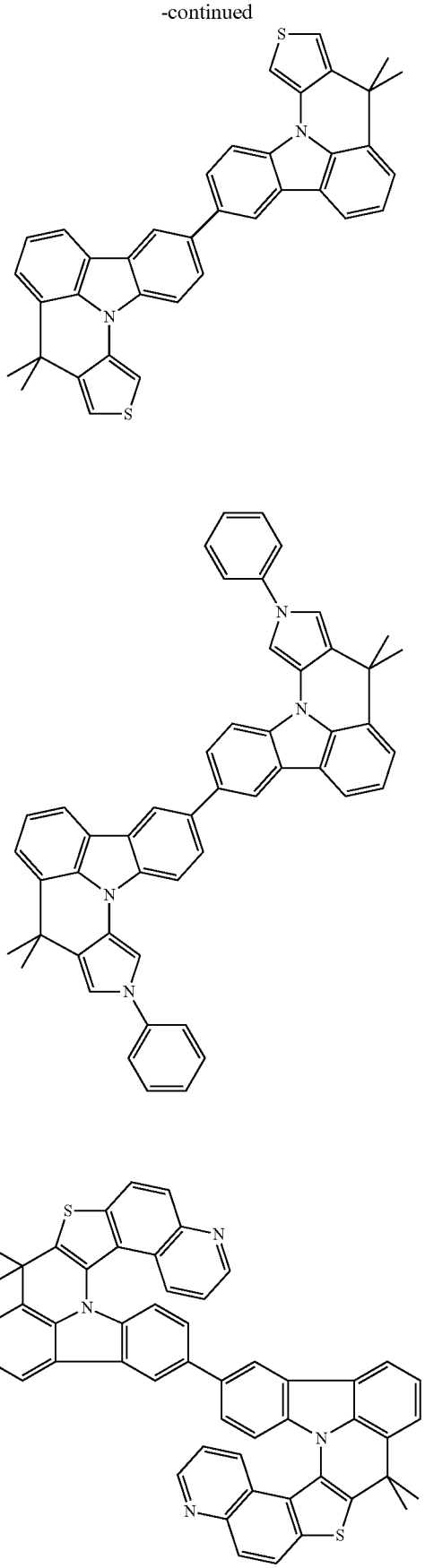

55
-continued
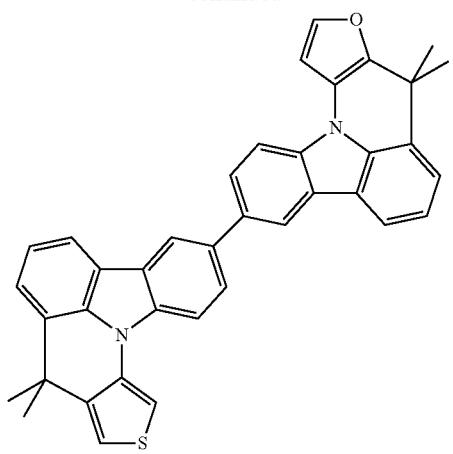
56
-continued
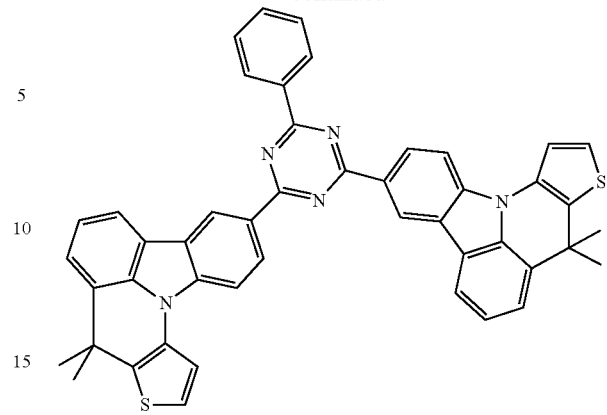
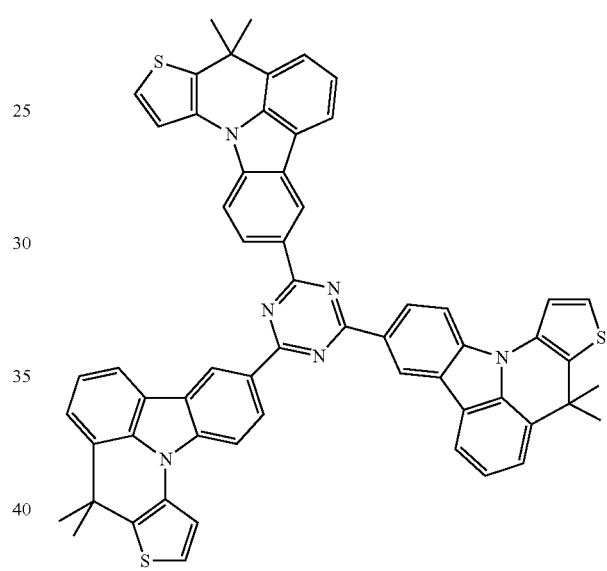
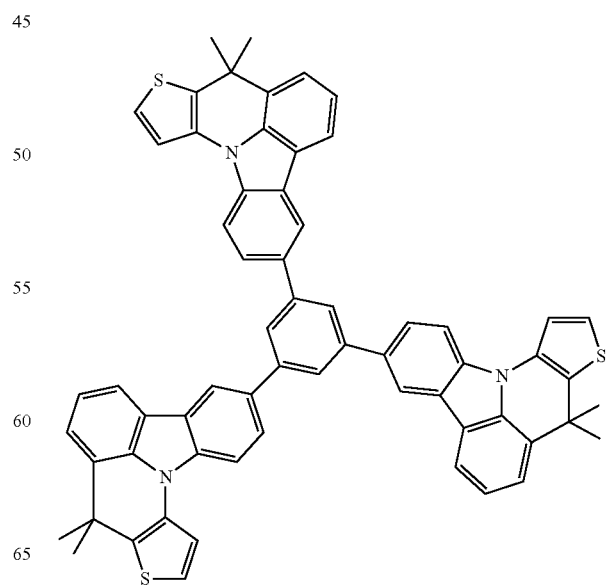

57
-continued
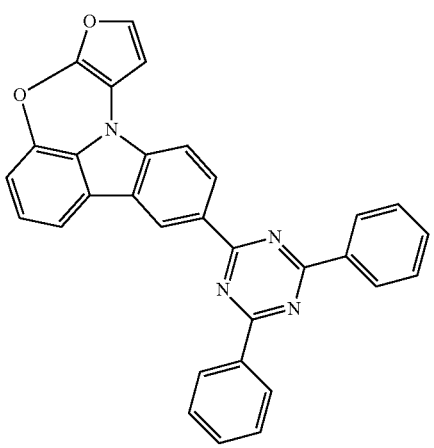
58
-continued
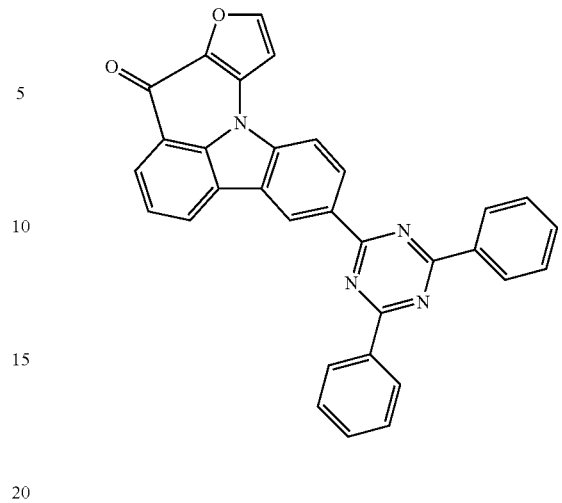
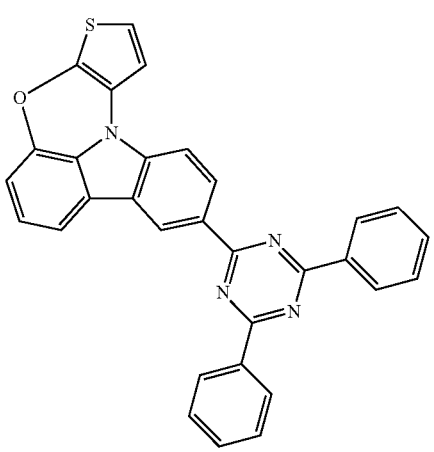
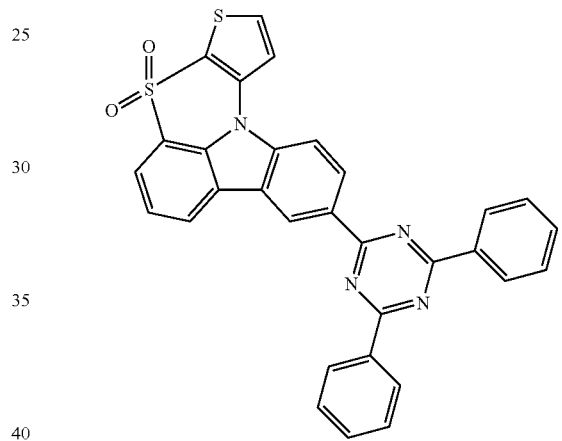
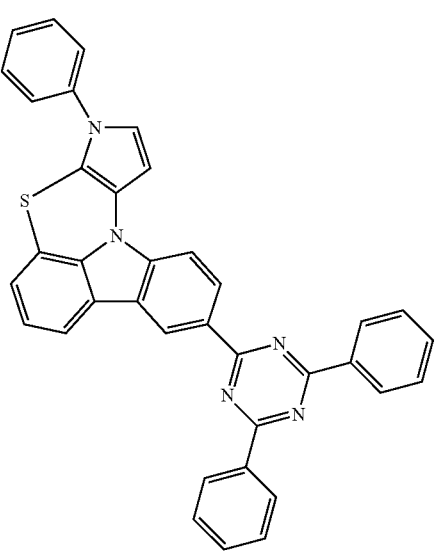
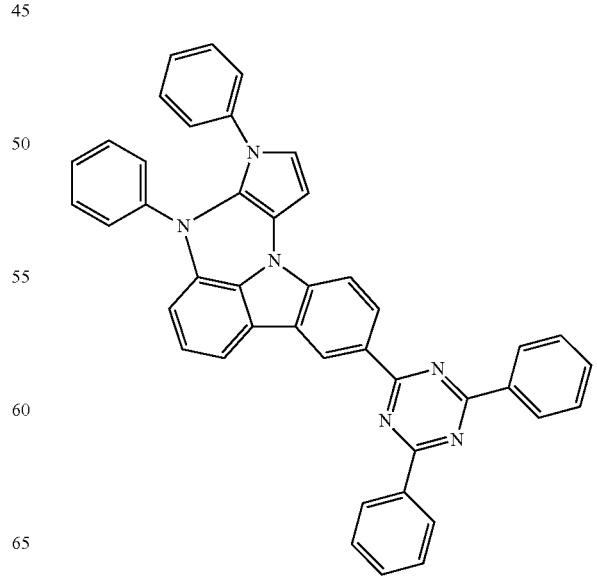

-continued
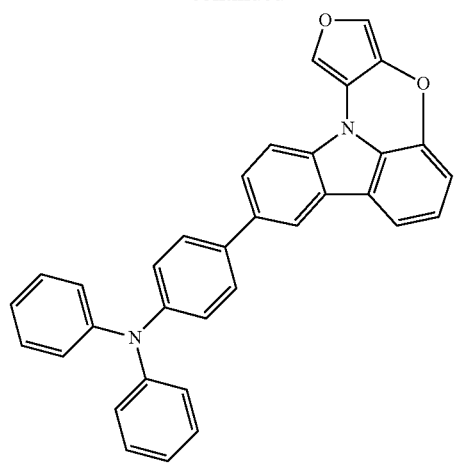
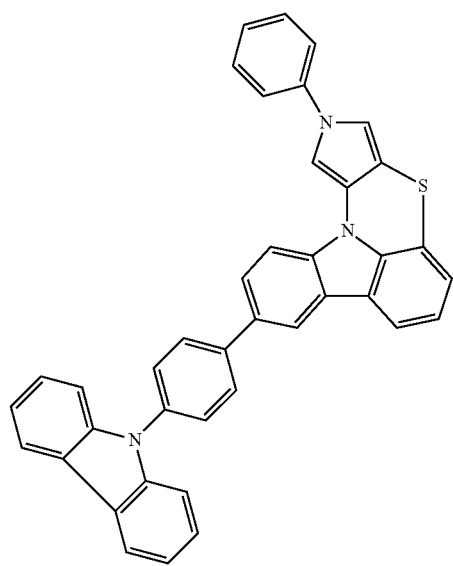
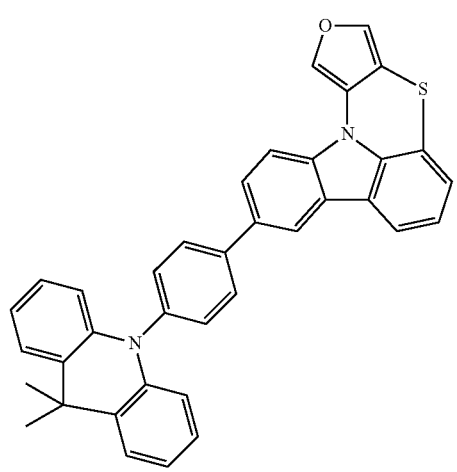
-continued
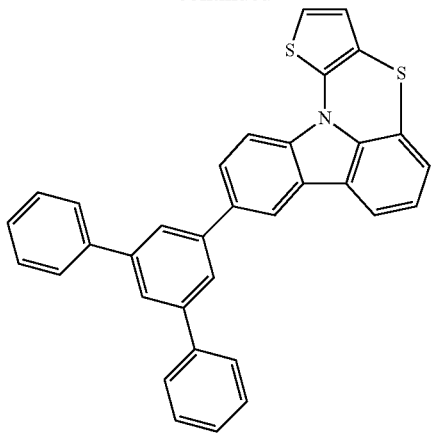
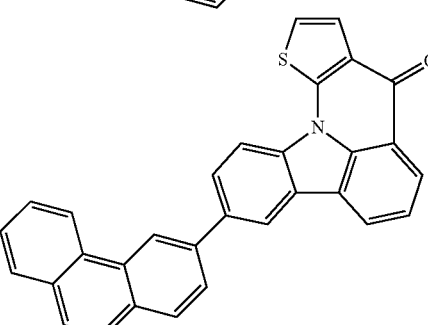
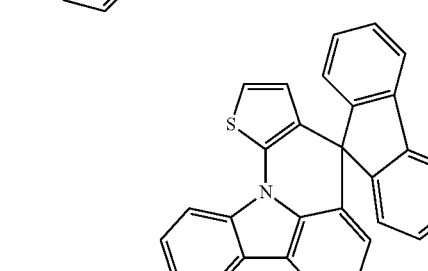
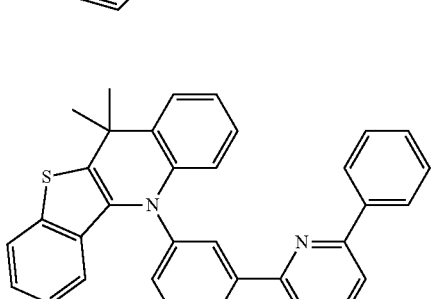

61
-continued
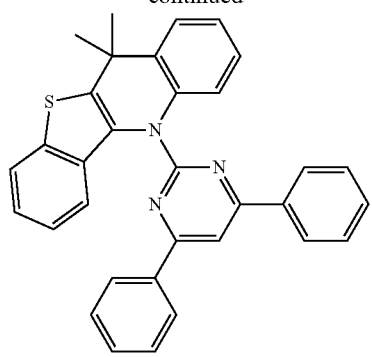
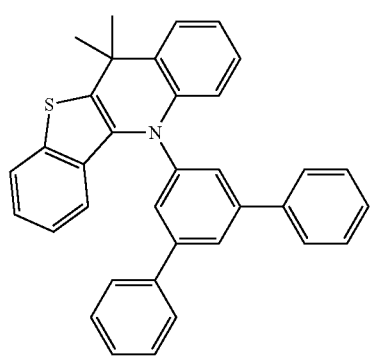
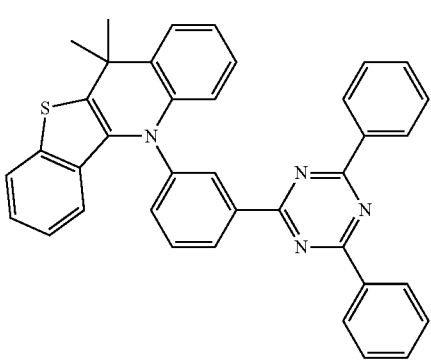
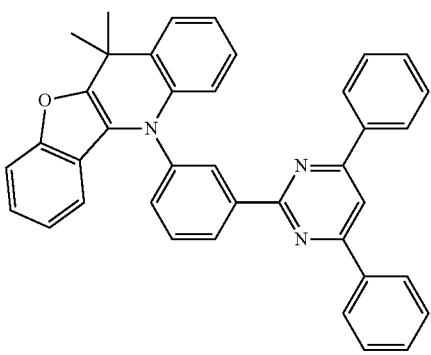
62
-continued
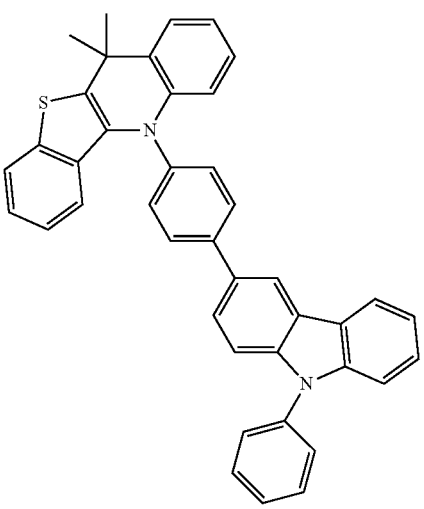
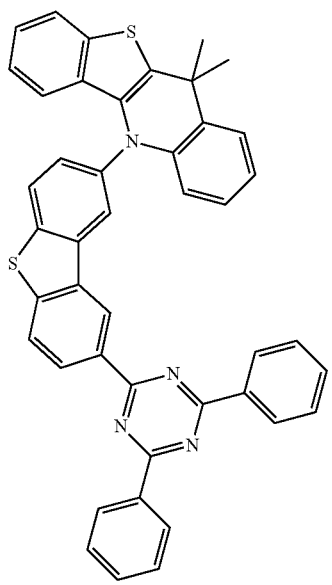
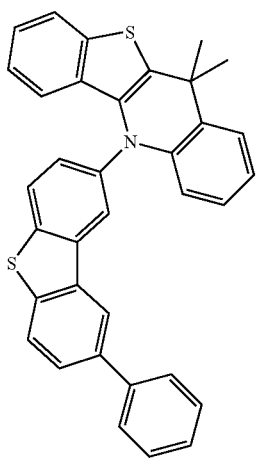

-continued

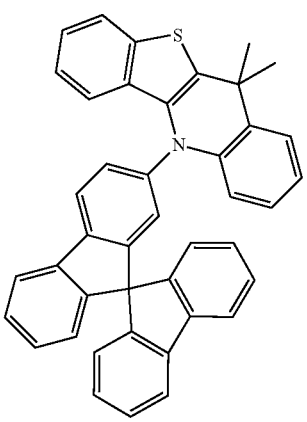 [SMILES: CC1(C)c2ccccc2N(c2ccc3c(c2)C2(c4ccccc4-c4ccccc42)c2ccccc2-3)c2c1sc1ccccc21]

The synthesis of the compounds according to the invention is shown in the following schemes. Scheme 1a and 1b and Scheme 2 show the synthesis of compounds in which Ar² and Ar³ stand for phenyl groups and Y² stands for a single bond. The starting material employed for this purpose is an optionally substituted carbazole, which is reacted with a correspondingly substituted five-membered heteroaromatic ring compound in an Ullmann coupling, a Buchwald coupling or another coupling reaction. The compounds according to the invention obtained in this way can be functionalised further by reaction sequences such as bromination and subsequent C—C and C—N coupling reactions, as also shown in Scheme 1 and 2. Depending on the desired position of the bromine substitution, cyclisation can take place via the intermediate of a tertiary alcohol before the bromination (Scheme 1) or after the bromination (Scheme 2). Ring closure under the influence of acid results in the formation of a divalent bridge between the aromatic substituent and the carbazole. Suitable here is, for example, a carboxylate group or an acetyl group, which can then be converted into a carbon bridge in the ring-closure reaction (Scheme 1 and 2). R in the schemes stands for a substituent as defined above.

Scheme 1 a)

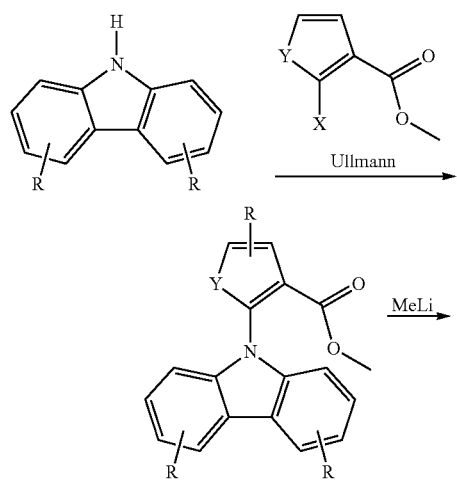

-continued

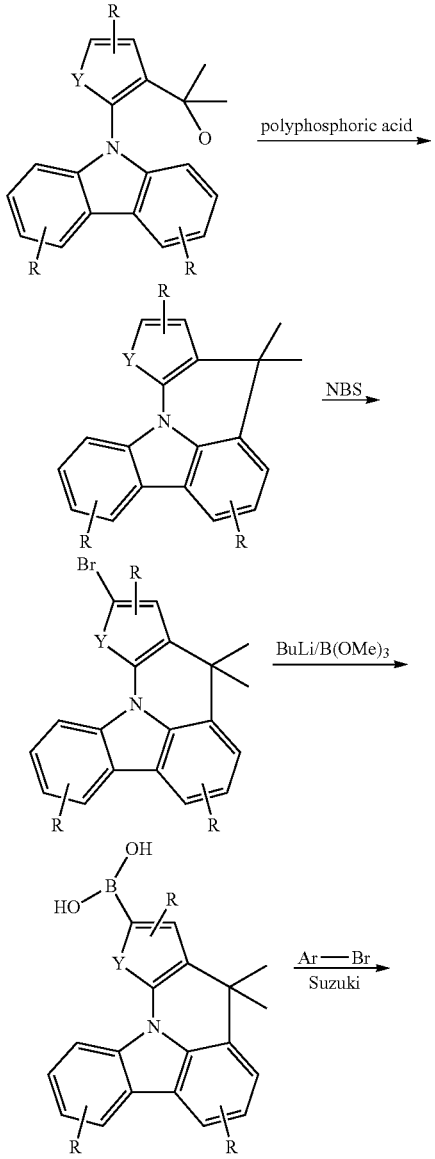

X = I, Br
Y = N—Ar, O, S b)

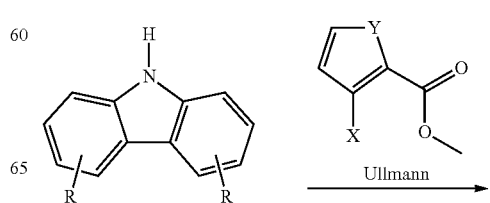

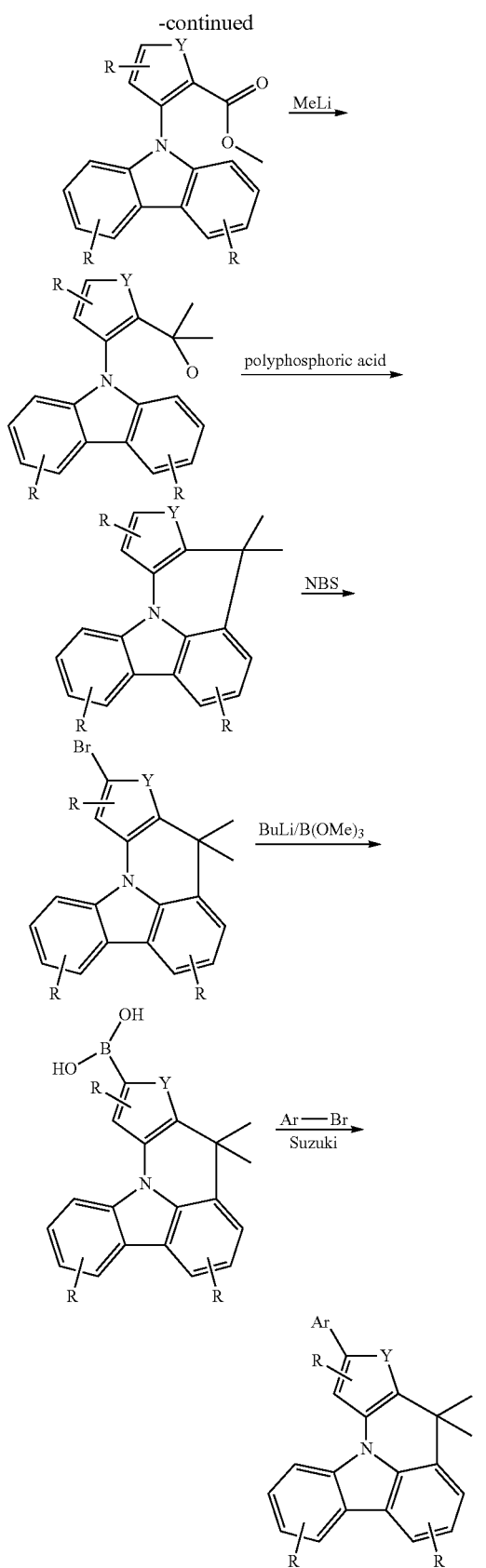
X = I, Br
Y = N—Ar, O, S
Scheme 2
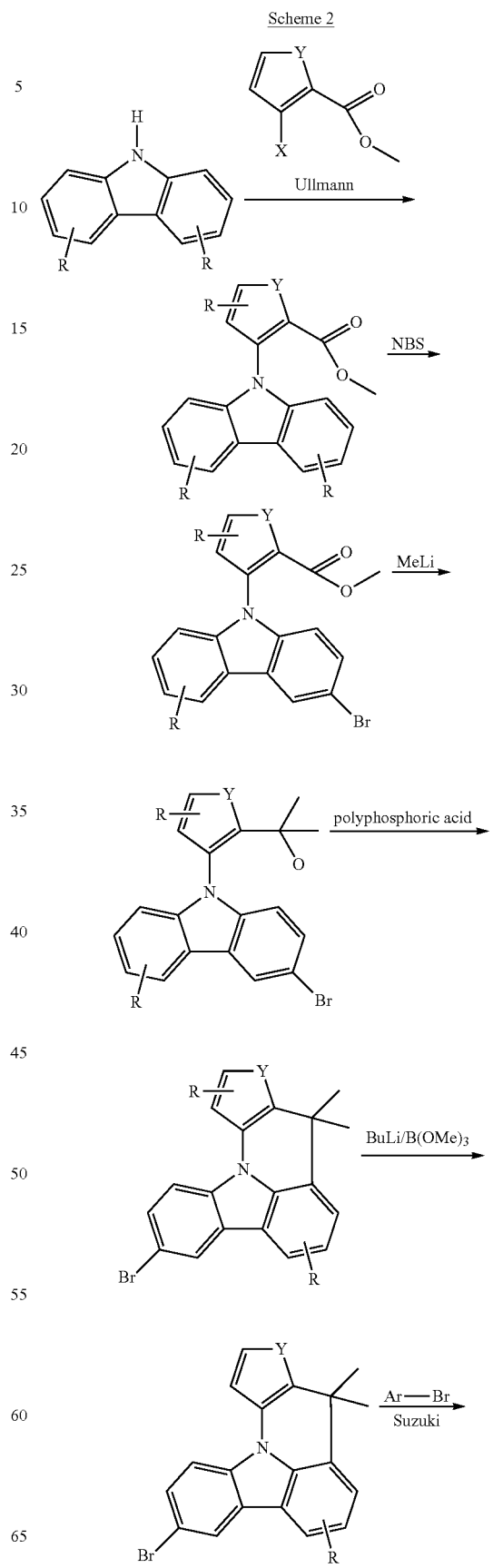

-continued

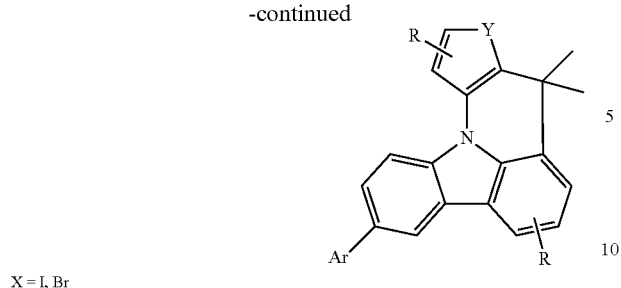

X = I, Br
Y = N—Ar, O, S

The introduction of aromatic substituents on the bridge Y is shown by way of example in the following Scheme 3. Here, the carboxylate is reacted with an aryl-organic compound, for example with an aromatic Grignard compound, instead of with an alkyl-organic compound.

Scheme 3

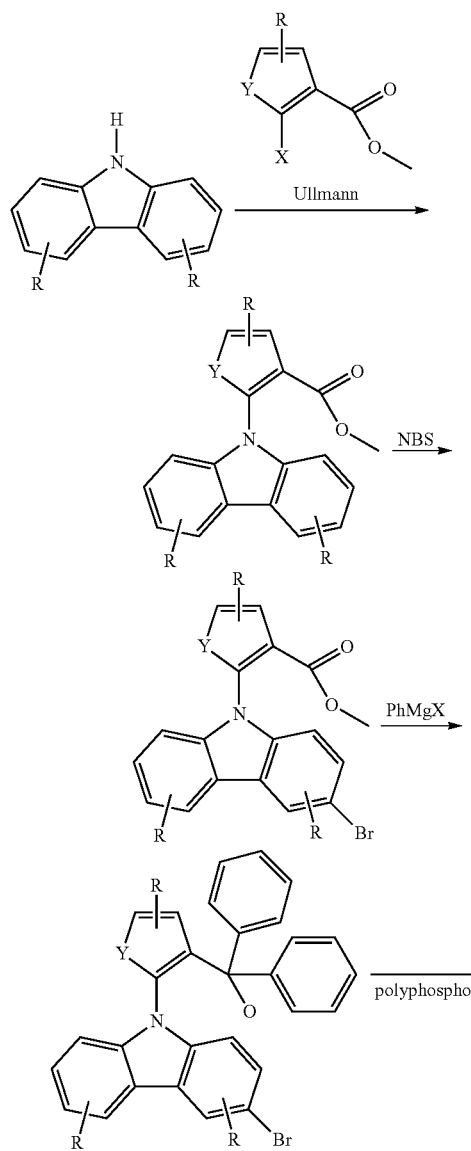

-continued

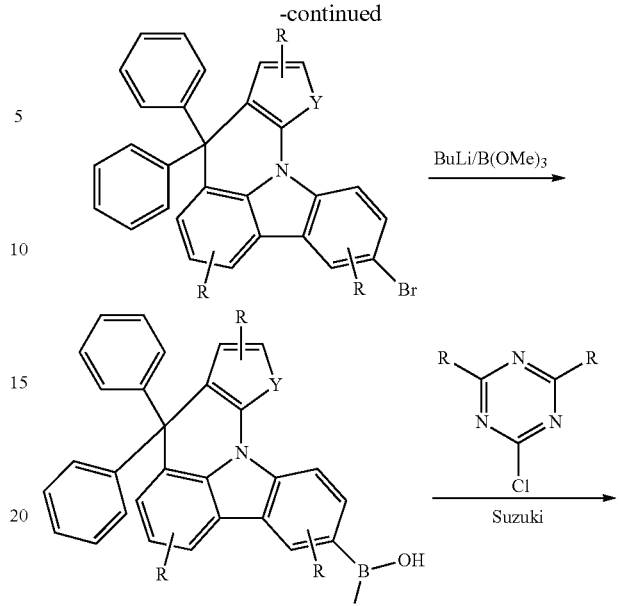

X = Br, I
Y = NAr, O, S

Also suitable is an aryl alcohol group, which can then be converted in the ring-closure reaction into an oxygen bridge, or a thio group, which can then be converted in the ring-closure reaction into a sulfur bridge (Scheme 4). Also suitable is a nitro group or amino group, which can then be converted into a nitrogen bridge in the ring-closure reaction (Scheme 5). The divalent bridge can subsequently be substituted by further radicals, for example by alkyl or aryl groups. The bridged carbazole compound prepared in this way can then be functionalised, for example halogenated, preferably brominated, in a further step.

Scheme 4

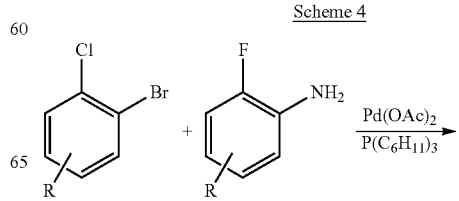

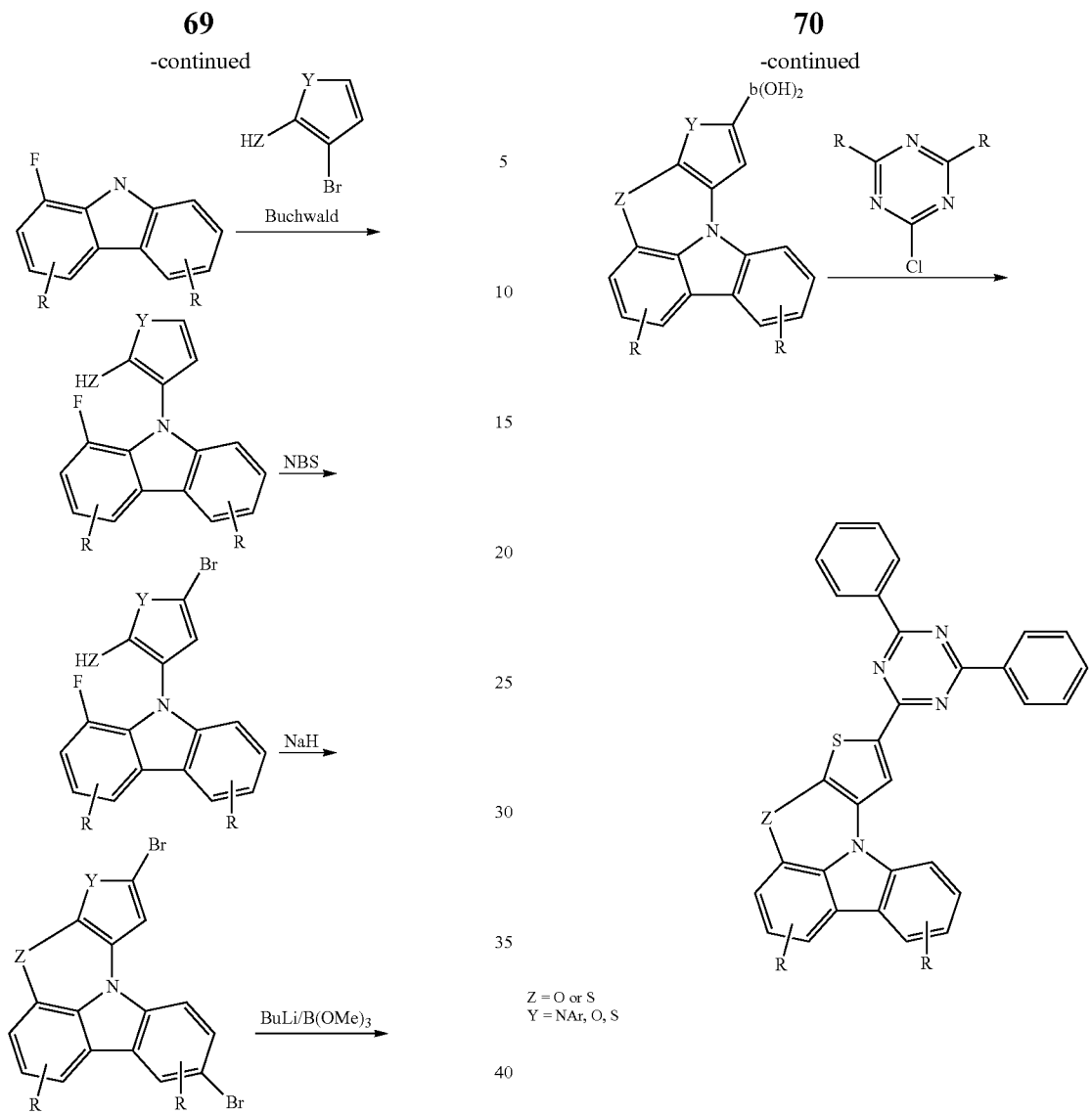
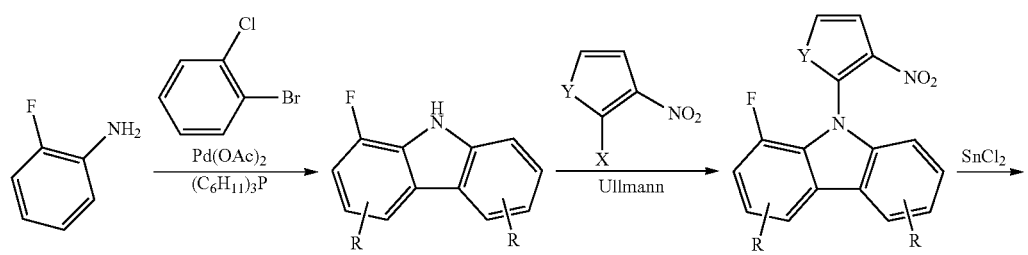
Scheme 5

-continued

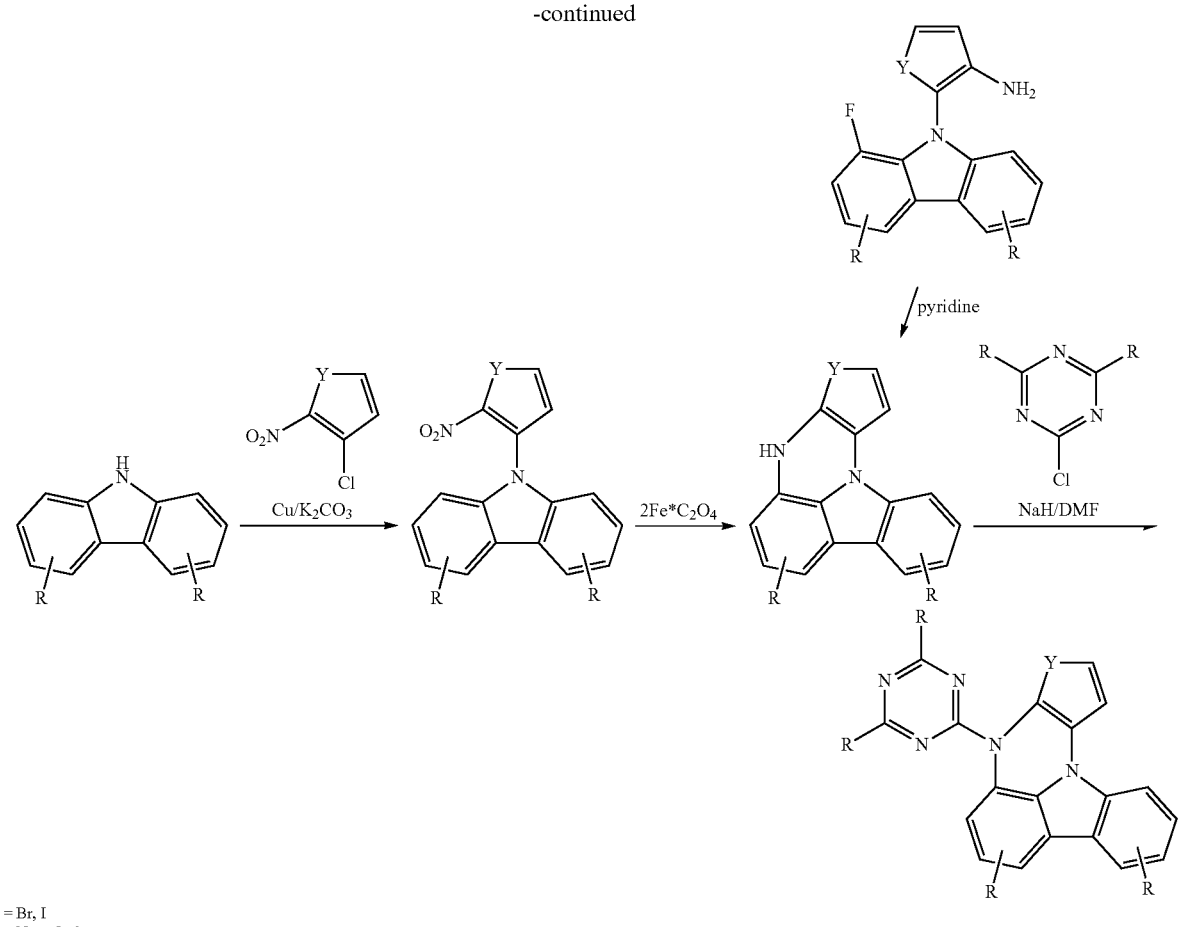

X = Br, I
Y = NAr, O, S

The functionalised, in particular brominated compounds represent the central building block for further functionalisation, as depicted in Scheme 1 to 5. Thus, these functionalised bridged compounds can easily be converted into corresponding boronic acids and converted into further compounds of the formula (1) according to the invention, for example by Suzuki coupling to halogenated aromatic compounds. Likewise, other coupling reactions (for example Stille coupling, Heck coupling, Sonogashira coupling, etc.) can be used. Hartwig-Buchwald coupling to diarylamines results in triarylamine derivatives. Correspondingly, aliphatic amines, carbazoles, etc., can be introduced as substituents. Suitable as functionalisation are furthermore formyl, alkylcarbonyl and arylcarbonyl groups or protected analogues thereof, for example in the form of the corresponding dioxolanes. The brominated compounds can furthermore be lithiated and converted into ketones by reaction with electrophiles, such as benzonitrile, and subsequent acidic hydrolysis or reacted with chlorodiphenylphosphines with subsequent oxidation to give phosphine oxides.

Compounds in which $Y^2$ stands for a divalent group instead of for a single bond are accessible entirely analogously by correspondingly employing as starting material instead of carbazole compounds which contain a different group $Y^2$.

The present invention therefore furthermore relates to a process for the preparation of a compound of the formula (1) or (2), comprising the reaction steps:

a) synthesis of the skeleton which carries a reactive leaving group instead of a group R; and
b) introduction of the group R, preferably by a coupling reaction, for example Suzuki coupling or Hartwig-Buchwald coupling.

The reactive leaving group here is preferably selected from Cl, Br, I, boronic acid or boronic acid derivatives, triflate or tosylate or Y stands for NH, i.e. the reactive leaving group is hydrogen, if a bond is formed between N and R.

The present invention furthermore relates to mixtures comprising at least one compound according to the invention and at least one further compound. The further compound can be, for example, a fluorescent or phosphorescent dopant if the compound according to the invention is used as matrix material. Suitable fluorescent and phosphorescent dopants are indicated below in connection with the organic electroluminescent devices and are also preferred for the mixtures according to the invention. The further compound can also be a dopant if the compound according to the invention is employed as hole-transport or electron-transport compound. Suitable dopants are indicated below in connection with the organic electroluminescent devices.

For processing from solution or from the liquid phase, for example by spin coating or by printing processes, solutions or formulations of the compounds or mixtures according to the invention are necessary. It may be preferred to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, a suspension or a mini-emulsion, comprising at least one compound or mixture according to the invention and one or more solvents, in particular organic solvents. The way in which solutions of this type can be prepared is known to the person skilled in the art and described, for example, in WO 2002/072714, WO 2003/019694 and the literature cited therein.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the above-mentioned compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) to (11) or formula (5a) to (11d) as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) to (11) or formula (5a) to (11d) is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) to (11) or formula (5a) to (11d) is employed as matrix material for an emitting compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state >1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1) to (11) or (5a) to (11d) and the emitting compound comprises between 99 and 1% by vol., preferably between 98 and 10% by vol., particularly preferably between 97 and 60% by vol., in particular between 95 and 80% by vol., of the compound of the formula (1) to (11) or (5a) to (11d), based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) to (11) or formula (5a) to (11d) as matrix material for a phosphorescent emitter in combination with a further matrix material. Particularly suitable matrix materials which can be employed in combination with the compounds of the formula (1) to (11) or formula (5a) to (11d) are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779, WO 2010/050778, in accordance with the unpublished applications DE 102009048791.3 or DE 102010005697.9. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709 and WO 2011/032626. Furthermore suitable are the complexes in accordance with the unpublished applications DE 102009057167.1, EP 10006208.2 and DE 102010027317.1. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1) to (11) or (5a) to (11d) is employed as electron-transport material in an electron-transport or electron-injection layer. At least one substituent R or $R^1$, here is preferably selected from structures of the formulae (12) to (33) indicated above. The emitting layer here may be fluorescent or phosphorescent. If the compound is employed as electron-transport material, it may be preferred for it to be doped, for example with alkali-metal complexes, such as, for example, Liq (lithium hydroxyquinolinate).

In still a further preferred embodiment of the invention, the compound of the formula (1) to (11) or (5a) to (11d) is employed in a hole-blocking layer. At least one substituent R or $R^1$, in particular R, here is preferably selected from structures of the formulae (12) to (33) indicated above. A hole-blocking layer is taken to mean a layer which is directly adjacent to an emitting layer on the cathode side, in particular in a phosphorescent electroluminescent device.

It is furthermore possible to use the compound of the formula (1) to (11) or (5a) to (11d) both in a hole-blocking layer or electron-transport layer and also as matrix in an emitting layer. At least one substituent R or $R^1$, in particular R, here is preferably selected from structures of the formulae (12) to (33) indicated above.

In still a further preferred embodiment of the invention, the compound of the formula (1) to (11) or (5a) to (11d) is employed in a hole-transport layer or in an electron-blocking layer or exciton-blocking layer. At least one substituent R or $R^1$, in particular R, here is preferably selected from structures of the formulae (34) to (47) indicated above.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) to (11) or formula (5a) to (11d).

Preference is furthermore given to an organic electroluminescent device, characterised in that one or more layers are coated by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose. These processes are also particularly suitable for oligomers, dendrimers and polymers.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished over the prior art by the following surprising advantages:

1. The compounds according to the invention or compounds of the formula (1) to (11) or formula (5a) to (11d), employed as matrix material for fluorescent or phosphorescent emitters, result in high efficiencies and long lifetimes. This applies, in particular, if the compounds are employed as matrix material for a phosphorescent emitter.
2. The compounds according to the invention or compounds of the formula (1) to (11) or formula (5a) to (11d) are suitable not only as matrix for red- and green-phosphorescent compounds, but, in particular, also for blue-phosphorescent compounds.
3. In contrast to many compounds in accordance with the prior art which undergo partial or complete pyrolytic decomposition during sublimation, the compounds according to the invention have high thermal stability.
4. The compounds according to the invention, employed in organic electroluminescent devices, result in high efficiencies and in steep current/voltage curves with low use voltages.
5. Also on use as electron-transport material or as hole-transport material, the compounds according to the invention result in good properties with respect to the efficiency, the lifetime and the operating voltage of organic electroluminescent devices.

These above-mentioned advantages are not accompanied by an impairment in the other electronic properties.

The invention is explained in greater detail by the following examples, without wishing to restrict it thereby. The person skilled in the art will be able to carry out the invention throughout the range disclosed on the basis of the descriptions and prepare further compounds according to the invention without inventive step and use them in electronic devices or use the process according to the invention.

EXAMPLES

The following syntheses are carried out, unless indicated otherwise, in dried solvents under a protective-gas atmosphere. The starting point used can be, for example, methyl 3-bromothiophene-2-carboxylate (Synlett 2004, 6, 1113-1116). The numbers in the case of the starting materials which are known from the literature relate to the CAS number.

Example 1a

10-Bromo-8,8-dimethyl-8H-9-thia-11b-azacyclopenta[a]-fluoranthene (Compound 1a)

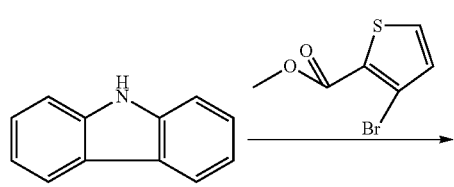

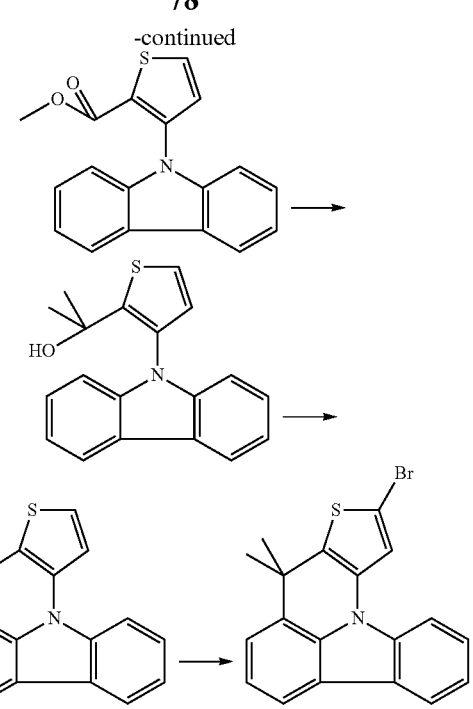

Step 1: Methyl 3-carbazol-9-ylthiophene-2-carboxylate 102 g (420 mmol) of 3-phenyl-9H-carbazole, 92 g (420 mmol) of methyl 3-bromothiophene-2-carboxylate, 24 g (375 mmol) of copper powder, 104 g (757 mmol) of potassium carbonate and 11 g (42 mmol) of 18-crown-6 are initially introduced in 1200 ml of DMF under protective gas and heated at 130° C. for 86 h. The mixture is subsequently evaporated, washed by stirring with hot heptane and purified by chromatography (heptane, dichloromethane 1:1). The product is washed by stirring with hot hexane, and the solid is isolated. Yield: 121 g (397 mmol), 65% of theory, purity according to $^1$H-NMR about 97%.

Step 2: 2-(3-Carbazol-9-ylthiophen-2-yl)propan-2-ol 85 g (277 mmol) of methyl 3-carbazol-9-ylthiophene-2-carboxylate are dissolved in 1700 ml of dried THF and degassed. The mixture is cooled to −78° C., and 740 ml (1110 mmol) of methyllithium are added over the course of 40 min. The mixture is allowed to warm to −40° C. over the course of 1 h, and the reaction is monitored by TLC. When the reaction is complete, it is carefully quenched with MeOH at −30° C. The reaction solution is evaporated to ⅓ of the volume, 1 l of methylene chloride is added, the mixture is washed, the organic phase is dried over MgSO$_4$ and evaporated. Yield: 96 g (249 mmol), 90% of theory, purity according to $^1$H-NMR about 97%.

Step 3: 8,8-Dimethyl-8H-9-thia-11b-azacyclopenta[a]fluoranthene 20 g (43.6 mmol) of 2-(3-carbazol-9-ylthiophen-2-yl)propan-2-ol are dissolved in 1.2 l of degassed toluene, and a suspension of 52 g of polyphosphoric acid and 36 ml of methanesulfonic acid is added, and the mixture is heated at 60° C. for 1 h. The batch is cooled, and water is added. A solid precipitates out and is dissolved with methylene chloride/THF (1:1). The solution is carefully rendered alkaline using 20% NaOH, the phases are separated and dried over MgSO₄. The solid obtained is washed by stirring with heptane. Yield: 12 g (41 mmol), 80% of theory, purity according to ¹H-NMR about 93%.

Step 4: 10-Bromo-8,8-dimethyl-8H-9-thia-11b-azacyclopenta[a]fluoranthene 60 g (207 mmol) of 8,8-dimethyl-8H-9-thia-11b-azacyclopenta[a]fluoranthene are cooled to −10° C. in 2 l of DMF, and 37.3 g (207 mmol) of NBS are added in portions. The mixture is subsequently allowed to come to room temperature and is stirred at this temperature for 6 h. 500 ml of water are then added to the mixture, which is then extracted with CH₂Cl₂. The organic phase is dried over MgSO₄, and the solvents are removed in vacuo. The product is washed by stirring with hot toluene, and the solid is isolated. Yield: 73 g (201 mmol), 97% of theory, purity according to ¹H-NMR about 98%.

Compounds 1b-1n are obtained analogously:

| Ex. | Starting material 1 | Starting material 1 | Product | Yield |
|---|---|---|---|---|
| 1b | 26137-08-6 | 56525-79-2 | | 95% |
| 1c | 59862-77-0 | | | 69% |
| 1d | 59862-77-0 | 56525-79-2 | | 81% |
| 1e | 478028-23-8 | | | 61% |

-continued
| Ex. | Starting material 1 | Starting material 1 | Product | Yield |
|---|---|---|---|---|
| 1f | 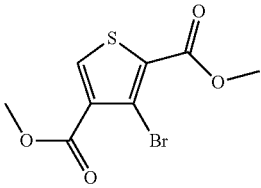 24647-86-7 | 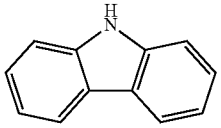 | 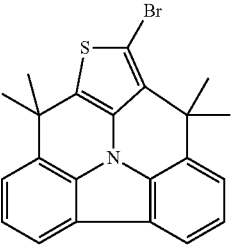 [SMILES: CC1(C)c2sc(Br)c3c2-n2c4c1cccc4c1cccc(c12)C3(C)C] | 62% |
| 1g | 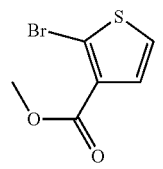 76360-43-5 | 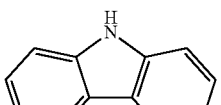 | 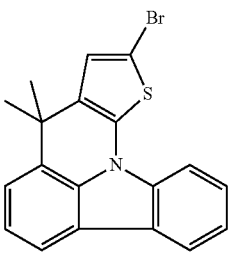 [SMILES: CC1(C)c2cc(Br)sc2-n2c3ccccc3c3cccc1c32] | 63% |
| 1g | 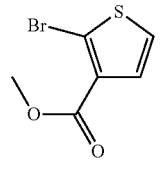 76360-43-5 | 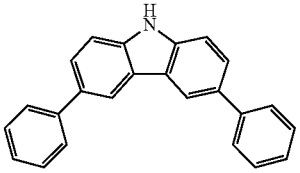 56525-79-2 56525-79-2 | 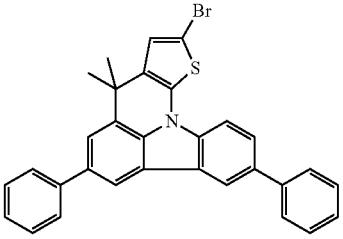 [SMILES: CC1(C)c2cc(Br)sc2-n2c3ccc(-c4ccccc4)cc3c3cc(-c4ccccc4)cc1c32] | 79% |
| 1h | 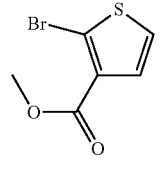 76360-43-5 | 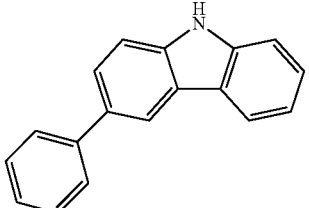 103012-26-6 | 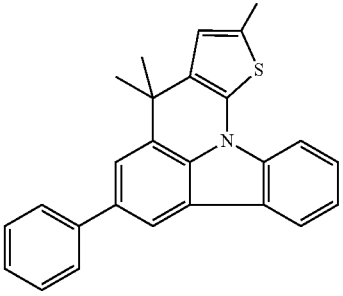 | 56% |
| 1j | 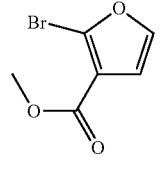 197846-06-3 | 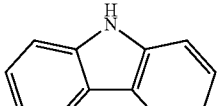 | 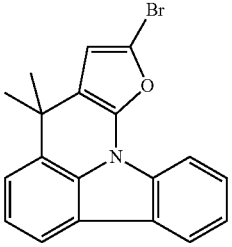 [SMILES: CC1(C)c2cc(Br)oc2-n2c3ccccc3c3cccc1c32] | 62% |

-continued

| Ex. | Starting material 1 | Starting material 1 | Product | Yield |
|---|---|---|---|---|
| 1i | 923010-50-8 | | | 71% |
| 1k | 35189-81-2 | | | 56% |
| 1l | 26137-08-6 | 244-78-0 | | 83% |
| 1m | 26137-08-6 | 6267-02-3 | | 65% |
| 1n | 26137-08-6 | 135-67-1 | | 62% |

Example 2a

3-Bromo-8,8-dimethyl-8H-9-thia-11b-azacyclopenta[a]-fluoranthene (Compound 2a)

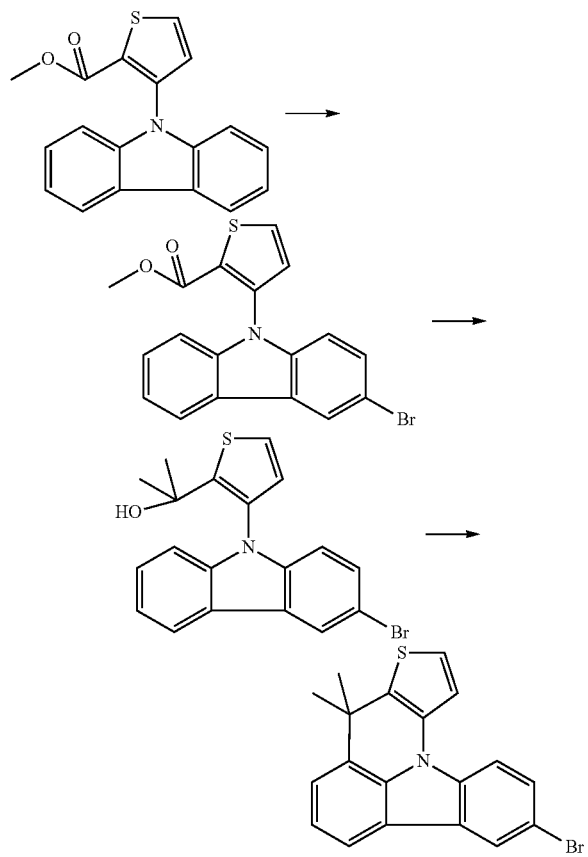

Step 1: Methyl 3-(3-bromocarbazol-9-yl)thiophene-2-carboxylate 63.5 g (207 mmol) of 8,8-dimethyl-8H-9-thia-11b-azacyclopenta[a]fluoranthene are cooled to −10° C. in 2 l of DMF, and 37.3 g (207 mmol) of NBS are added in portions. The mixture is subsequently allowed to come to room temperature and is stirred at this temperature for 6 h. 500 ml of water are then added to the mixture, which is then extracted with CH$_2$Cl$_2$. The organic phase is dried over MgSO$_4$, and the solvents are removed in vacuo. The product is washed by stirring with hot toluene, and the solid is isolated. Yield: 72 g (186 mmol), 90% of theory, purity according to $^1$H-NMR about 97%.

Step 2: 2-[3-(3-Bromocarbazol-9-yl)thiophen-2-yl]propan-2-ol 106 g (277 mmol) of methyl 3-(3-bromocarbazol-9-yl)thiophene-2-carboxylate are dissolved in 1700 ml of dried THF and degassed. The mixture is cooled to −78° C., and 740 ml (1110 mmol) of methyllithium are added over the course of 40 min. The mixture is allowed to warm to −40° C. over the course of 1 h, and the reaction is monitored by TLC. When the reaction is complete, it is carefully quenched with MeOH at −30° C. The reaction solution is evaporated to ⅓ of the volume, 1 l of methylene chloride is added, the mixture is washed, the organic phase is dried over MgSO$_4$ and evaporated. Yield: 97 g (251 mmol), 91% of theory, purity according to $^1$H-NMR about 97%.

Step 3: 8,8-Dimethyl-8H-9-thia-11b-azacyclopenta[a]fluoranthene 20 g (43.6 mmol) of 2-(3-bromocarbazol-9-ylthiophen-2-yl)propan-2-ol are dissolved in 1.2 l of degassed toluene, and a suspension of 52 g of polyphosphoric acid and 36 ml of methanesulfonic acid is added, and the mixture is heated at 60° C. for 1 h. The batch is cooled, and water is added. A solid precipitates out and is dissolved with methylene chloride/THF (1:1). The solution is carefully rendered alkaline using 20% NaOH, the phases are separated and dried over MgSO$_4$. The solid obtained is washed by stirring from heptane. Yield: 12 g (41 mmol), 80% of theory, purity according to $^1$H-NMR about 93%.

Step 4: 3-Bromo-8,8-dimethyl-8H-9-thia-11b-azacyclopenta[a]fluoranthene 80 g (207 mmol) of 8,8-dimethyl-8H-9-thia-11b-azacyclopenta[a]fluoranthene is cooled to −10° C. in 2 l of DMF, and 37.3 g (207 mmol) of NBS are added in portions. The mixture is subsequently allowed to come to room temperature and is stirred at this temperature for 6 h. 500 ml of water are then added to the mixture, which is then extracted with CH$_2$Cl$_2$. The organic phase is dried over MgSO$_4$, and the solvents are removed in vacuo. The product is washed by stirring with hot toluene, and the solid is isolated. Yield: 70 g (190 mmol), 92% of theory, purity according to $^1$H-NMR about 98%.

Compounds 2b-2e are obtained analogously:

| Ex. | Starting material 1 | Product | Yield |
|---|---|---|---|
| 2b | (34128-30-8) | | 59% |
| 2c | (1248548-62-0) | | 74% |

-continued

| Ex. | Starting material 1 | Product | Yield |
|---|---|---|---|
| 2d | 145429-99-8 | | 65% |
| 2e | 1188365-72-1 | | 51% |

Example 3a 8,8-Dimethyl-8H-9-thia-11b-azacyclopenta[a]fluoranthene-10-boronic acid (Compound 3a)

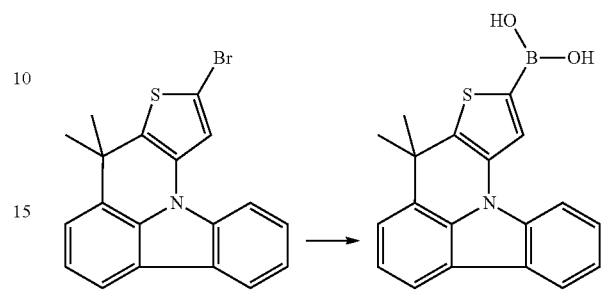

85 g (233 mmol) of 10-bromo-8,8-dimethyl-8H-9-thia-11b-azacyclopenta-[a]fluoranthene are dissolved in 1400 ml of dry THF, 121 ml (303 mmol) of a 2.5 M solution of n-butyllithium in cyclohexane are added dropwise at −70° C., after 1 h 33 ml of trimethyl borate (302 mmol) are added dropwise, the mixture is allowed to come to room temperature over the course of 1 h, the solvent is removed, and the residue, which is uniform according to $^1$H-NMR, is employed in the subsequent reaction without further purification. The yield is 69 g (207 mmol), corresponding to 90% of theory.

Compounds 3b-3o are obtained analogously:

| Ex. | Starting material 1 | Product | Yield |
|---|---|---|---|
| 3b | | | 86% |
| 3c | | | 79% |

-continued

| Ex. | Starting material 1 | Product | Yield |
|---|---|---|---|
| 3d | | | 83% |
| 3e | | | 83% |
| 3f | | | 77% |
| 3g | | | 86% |

-continued

| Ex. | Starting material 1 | Product | Yield |
|---|---|---|---|
| 3h | | | 80% |
| 3j | | | 69% |
| 3i | | | 82% |
| 3k | | | 64% |
| 3l | | | 56% |

| Ex. | Starting material 1 | Product | Yield |
|---|---|---|---|
| 3m | | | 80% |
| 3n | | | 75% |
| 3o | | | 78% |
Example 4a
10-(4,6-Diphenyl-1,3,5-triazin-2-yl)-8,8-dimethyl-8H-9-thia-11b-azacyclopenta[a]fluoranthene (Compound 4a)
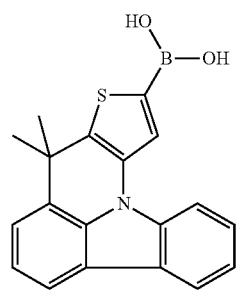 
-continued
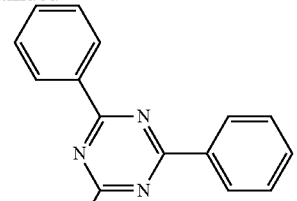
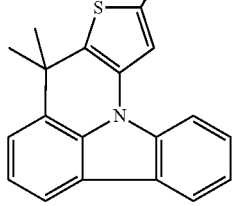
36.6 g (110.0 mmol) of 8,8-dimethyl-8H-9-thia-11b-azacyclopenta[a]-fluoranthene-10-boronic acid, 29.5 g (110.0 mmol) of 2-chloro-4,6-diphenyl-1,3,5-triazine and 44.6 g (210.0 mmol) of tripotassium phosphate are suspended in 500 ml of toluene, 500 ml of dioxane and 500 ml of water.

913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum, purity is 99.9%. The yield is 45 g (88 mmol), corresponding to 80% of theory.

Compounds 4b-4r are obtained analogously:

| Ex. | Starting material 1 | Product |
|---|---|---|
| 4b | [structure] | [structure] 3842-55-5 |
| 4c | [structure] | [structure] 3842-55-5 |
| 4d | [structure] | [structure] 103068-20-8 |
| 4e | [structure] | [structure] 864377-28-6 |
| 4f | [structure] | [structure] 3842-55-5 |

-continued
| | | | |
|---|---|---|---|
| 4g | 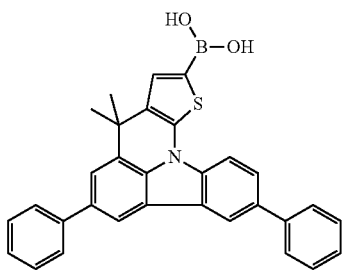 | 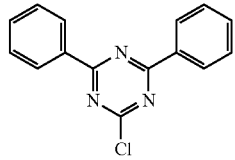
3842-55-5 | |
| 4h | 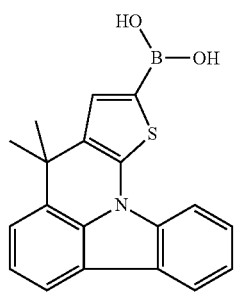 | 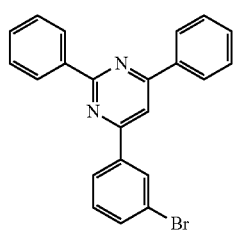 [SMILES: Brc1cccc(-c2cc(-c3ccccc3)nc(-c3ccccc3)n2)c1]
864377-28-6 | |
| 4j | 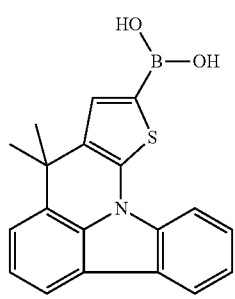 [SMILES: CC1(C)c2cc(B(O)O)sc2-n2c3ccccc3c3cccc1c32] | 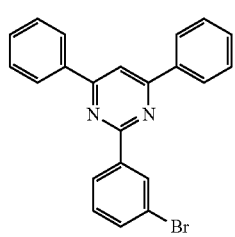 [SMILES: Brc1cccc(-c2nc(-c3ccccc3)cc(-c3ccccc3)n2)c1]
864377-22-0 | |
| 4i | 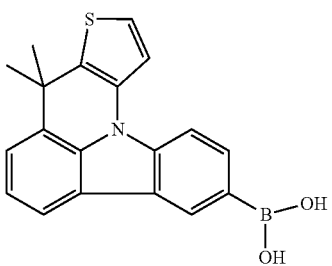 [SMILES: CC1(C)c2sccc2-n2c3ccc(B(O)O)cc3c3cccc1c32] | 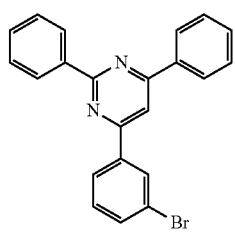 [SMILES: Brc1cccc(-c2cc(-c3ccccc3)nc(-c3ccccc3)n2)c1]
864377-28-6 | |
| 4k | 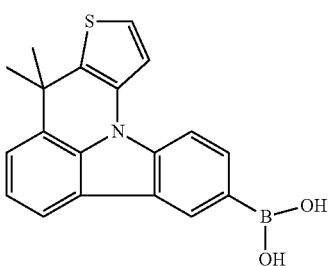 | 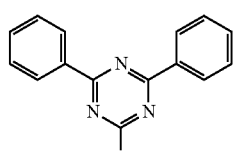 | |

-continued
| | | | |
|---|---|---|---|
| 4l | 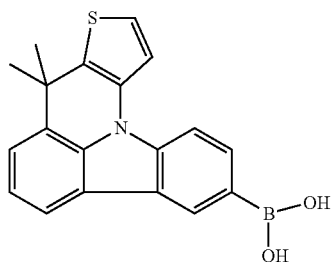 [SMILES: CC1(C)c2sccc2-n2c3ccc(B(O)O)cc3c3cccc1c32] | 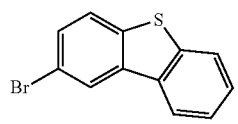 [SMILES: Brc1ccc2sc3ccccc3c2c1] 22439-61-8 | |
| 4m | 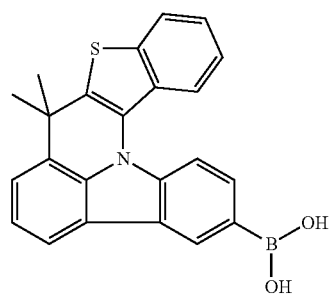 [SMILES: CC1(C)c2sc3ccccc3c2-n2c3ccc(B(O)O)cc3c3cccc1c32] | 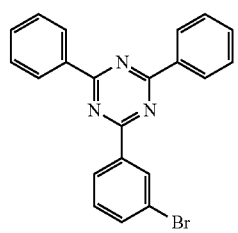 [SMILES: Brc1cccc(-c2nc(-c3ccccc3)nc(-c3ccccc3)n2)c1] 864377-28-6 | |
| 4n | 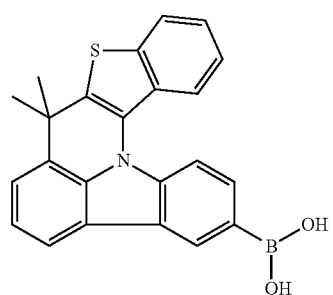 [SMILES: CC1(C)c2sc3ccccc3c2-n2c3ccc(B(O)O)cc3c3cccc1c32] | 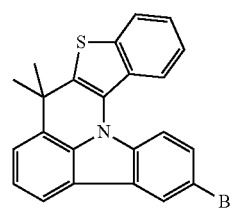 | |
| 4o | 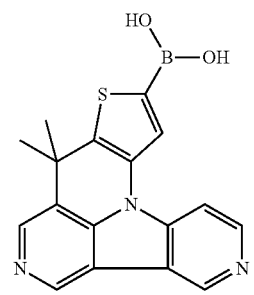 [SMILES: CC1(C)c2sc(B(O)O)cc2-n2c3ccncc3c3cncc1c32] | 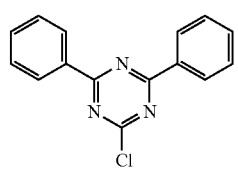 [SMILES: Clc1nc(-c2ccccc2)nc(-c2ccccc2)n1] 3842-55-5 | |
| 4p | 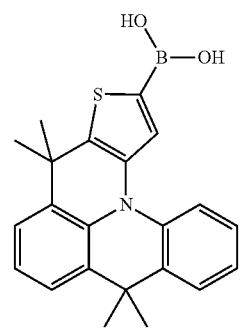 [SMILES: CC1(C)c2ccccc2N2c3cc(B(O)O)sc3C(C)(C)c3cccc1c32] | 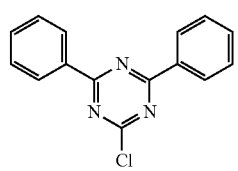 [SMILES: Clc1nc(-c2ccccc2)nc(-c2ccccc2)n1] 3842-55-5 | |

-continued
| 4q | 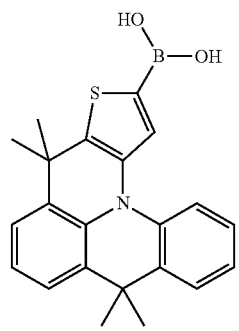 [SMILES: CC1(C)c2ccccc2N2c3cc(B(O)O)sc3C(C)(C)c3cccc1c32] | 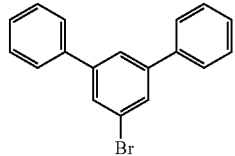 [SMILES: Brc1cc(-c2ccccc2)cc(-c2ccccc2)c1] |
|---|---|---|
| | | 103068-20-8 |
| 4r | 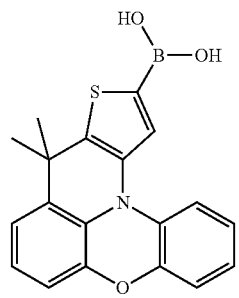 [SMILES: CC1(C)c2cccc3c2N(c2ccccc2O3)c2cc(B(O)O)sc21] | 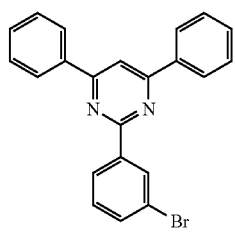 [SMILES: Brc1cccc(-c2nc(-c3ccccc3)cc(-c3ccccc3)n2)c1] |
| | | 864377-22-0 |
| Ex. | Product | Yield |
|---|---|---|
| 4b | 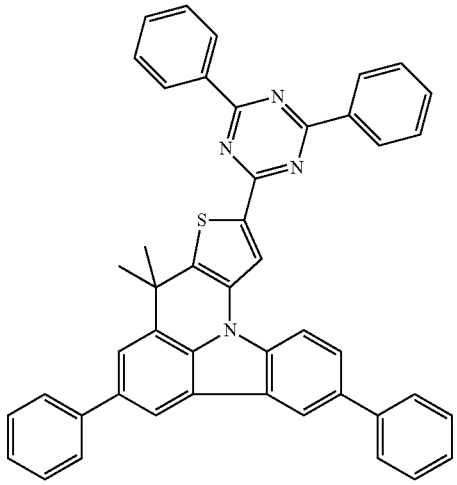 [SMILES: CC1(C)c2sc(-c3nc(-c4ccccc4)nc(-c4ccccc4)n3)cc2-n2c3ccc(-c4ccccc4)cc3c3cc(-c4ccccc4)cc1c32] | 83% |
| 4c | 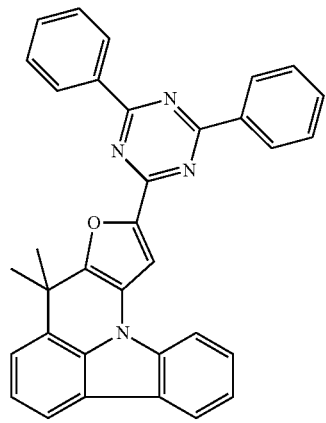 [SMILES: CC1(C)c2oc(-c3nc(-c4ccccc4)nc(-c4ccccc4)n3)cc2-n2c3ccccc3c3cccc1c32] | 87% |

| | | -continued | |
|---|---|---|---|
| 4d | 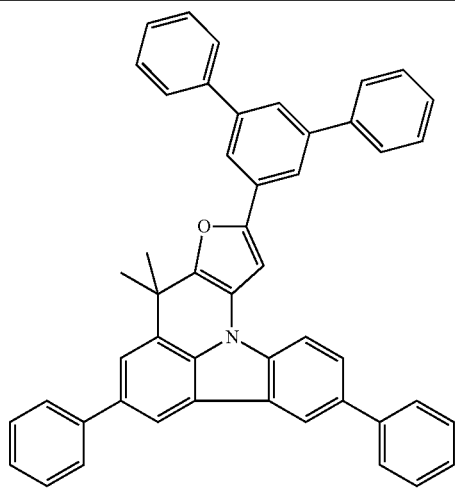 | | 80% |
| 4e | 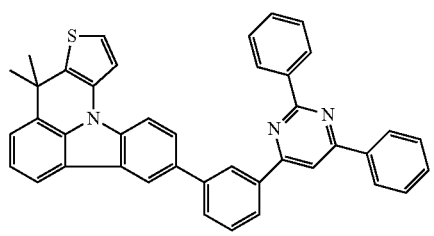 [SMILES: CC1(C)c2sccc2-n2c3ccc(-c4cccc(-c5cc(-c6ccccc6)nc(-c6ccccc6)n5)c4)cc3c3cccc1c32] | | 83% |
| 4f | 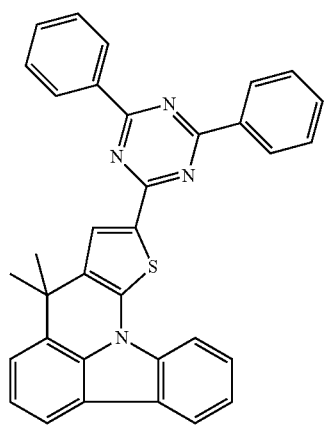 [SMILES: CC1(C)c2cc(-c3nc(-c4ccccc4)nc(-c4ccccc4)n3)sc2-n2c3ccccc3c3cccc1c32] | | 67% |
| 4g | 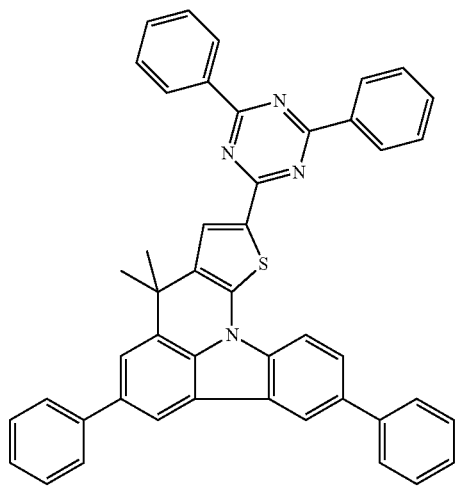 [SMILES: CC1(C)c2cc(-c3nc(-c4ccccc4)nc(-c4ccccc4)n3)sc2-n2c3ccc(-c4ccccc4)cc3c3cc(-c4ccccc4)cc1c32] | | 86% |

| | | |
|---|---|---|
| 4h | 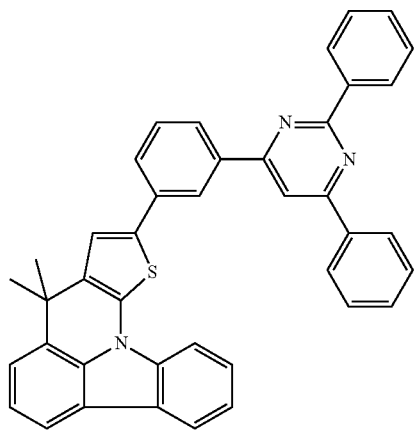 [SMILES: CC1(C)c2cc(-c3cccc(-c4cc(-c5ccccc5)nc(-c5ccccc5)n4)c3)sc2-n2c3ccccc3c3cccc1c32] | 80% |
| 4j | 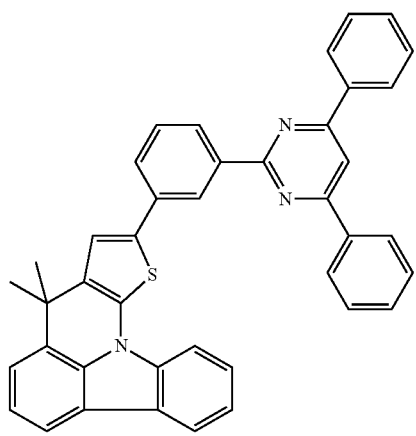 [SMILES: CC1(C)c2cc(-c3cccc(-c4nc(-c5ccccc5)cc(-c5ccccc5)n4)c3)sc2-n2c3ccccc3c3cccc1c32] | 69% |
| 4i | 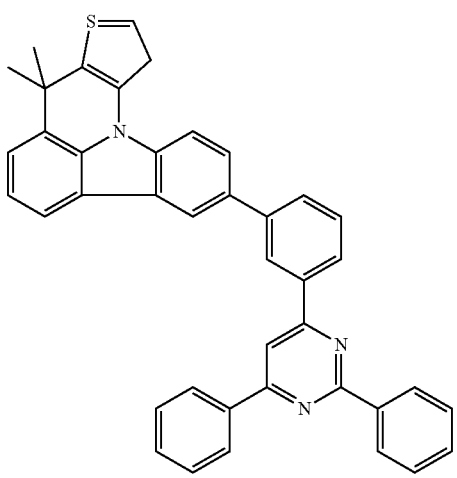 | 82% |

| | | |
|---|---|---|
| 4k | 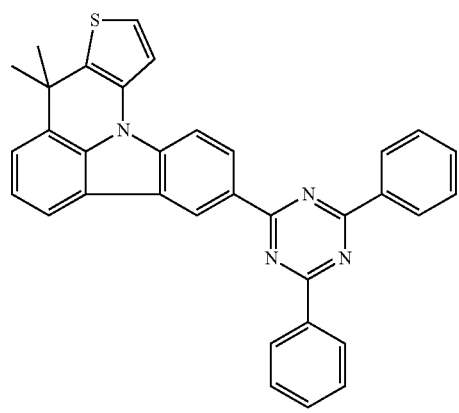 [SMILES: CC1(C)c2sccc2-n2c3ccc(-c4nc(-c5ccccc5)nc(-c5ccccc5)n4)cc3c3cccc1c32] | 75% |
| 4l | 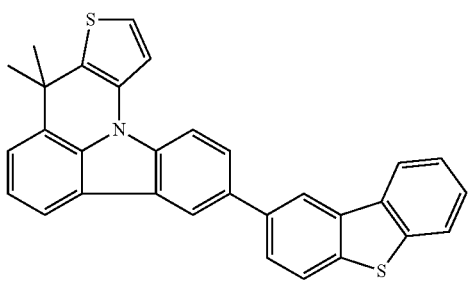 [SMILES: CC1(C)c2sccc2-n2c3ccc(-c4ccc5sc6ccccc6c5c4)cc3c3cccc1c32] | 87% |
| 4m | 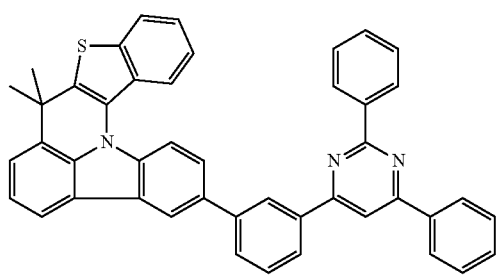 [SMILES: CC1(C)c2sc3ccccc3c2-n2c3ccc(-c4cccc(-c5cc(-c6ccccc6)nc(-c6ccccc6)n5)c4)cc3c3cccc1c32] | 65% |
| 4n | 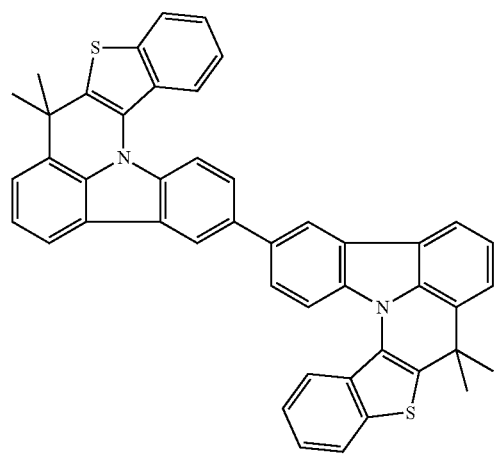 [SMILES: CC1(C)c2sc3ccccc3c2-n2c3ccc(-c4ccc5c(c4)c4cccc6c4n5-c4c(sc5ccccc45)C6(C)C)cc3c3cccc1c32] | 69% |

| | | |
|---|---|---|
| 4o | 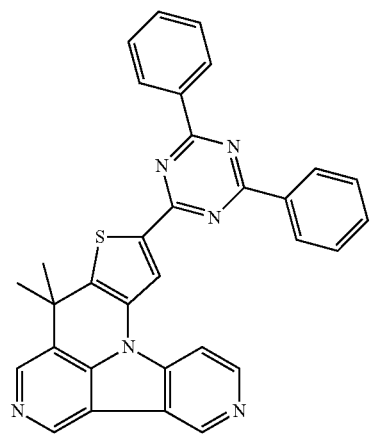 [SMILES: CC1(C)c2sc(-c3nc(-c4ccccc4)nc(-c4ccccc4)n3)cc2-n2c3ccncc3c3cncc1c32] | 73% |
| 4p | 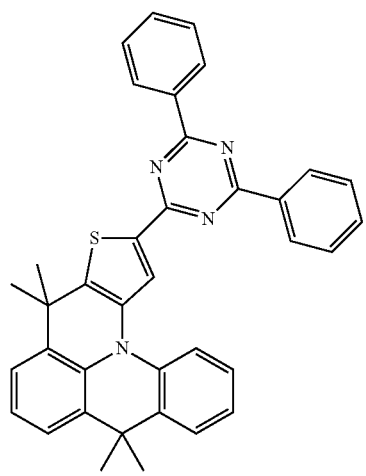 [SMILES: CC1(C)c2ccccc2N2c3cc(-c4nc(-c5ccccc5)nc(-c5ccccc5)n4)sc3C(C)(C)c3cccc1c32] | 78% |
| 4q | 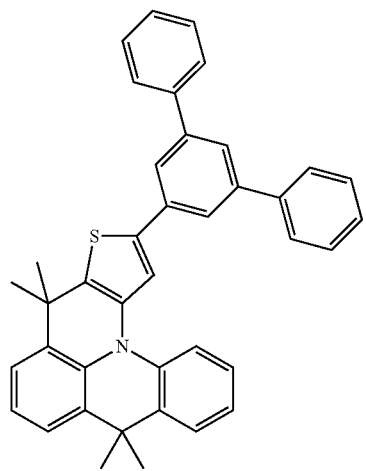 [SMILES: CC1(C)c2ccccc2N2c3cc(-c4cc(-c5ccccc5)cc(-c5ccccc5)c4)sc3C(C)(C)c3cccc1c32] | 68% |

| 4r | 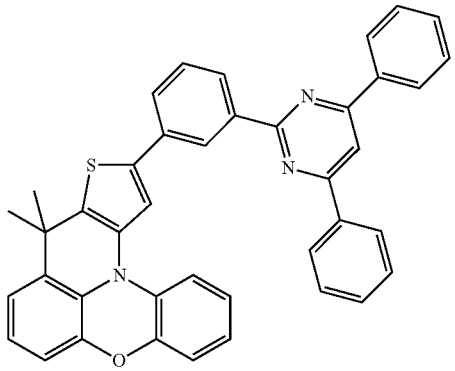 [SMILES: CC1(C)c2cccc3c2N(c2ccccc2O3)c2cc(-c3cccc(-c4nc(-c5ccccc5)cc(-c5ccccc5)n4)c3)sc21] | 71% |

Example 5

8,8-Dimethyl-6-[4-(1-phenyl-1H-benzoimidazol-2-yl)-phenyl]-8H-9-thia-11b-azacyclopenta[a]fluoranthene (Compound 5)

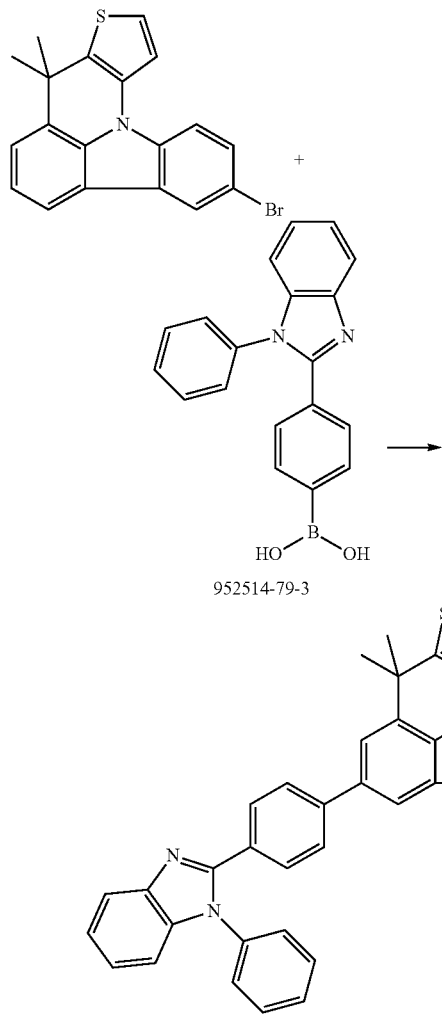

0.27 g (0.9 mmol) of tri-o-tolylphosphine and then 33.5 mg (0.15 mmol) of palladium(II) acetate are added with vigorous stirring to a degassed suspension of 10.3 g (28 mmol) of 6-bromo-8,8-dimethyl-8H-indolo[3,2,1,-de]-acridine and 9.42 g (30 mmol) of benzimidazoleboronic acid and 7.8 g (31.5 mmol) of potassium phosphate hydrate in a mixture of 7.5 ml of dioxane, 15 ml of toluene and 18 ml of water. After heating under reflux for 5 h, the mixture is allowed to cool. The precipitate is filtered off with suction, washed three times with 10 ml of ethanol/water (1:1, v:v) and three times with 5 ml of ethanol, subsequently dried in vacuo and recrystallised from dioxane. Yield: 12.7 g (22.9 mmol), 82% of theory, purity according to $^1$H-NMR about 99.9%.

Example 6a

8,8-Dimethyl-3-(9-phenyl-9H-carbazol-3-yl)-8H-9-thia-11b-azacyclopenta[a]fluoranthene (Compound 6a)

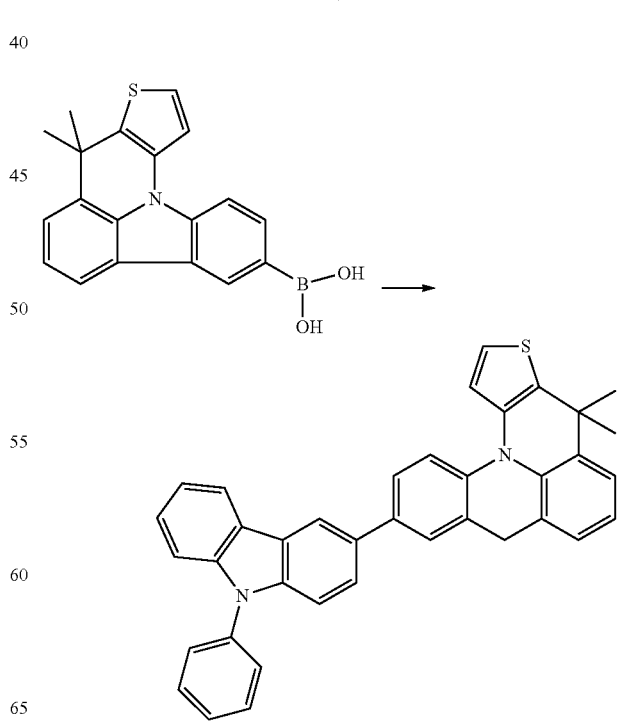

36.6 g (110 mmol) of 8,8-dimethyl-8H-9-thia-11b-azacyclopenta[a]fluoranthene-3-boronic acid, 35 g (110 mmol) of 3-bromo-9-phenyl-9H-carbazole and 9.7 g (92 mmol) of sodium carbonate are suspended in 350 ml of toluene, 350 ml of dioxane and 500 ml of water. 913 mg (3.0 mmol) of tri-o-tolylphosphine and 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from $CH_2Cl_2$/isopropanol and finally sublimed in a high vacuum. Yield: 52.4 g (100 mmol), 90% of theory, purity according to HPLC 99.9%.

Compounds 6b-6j are obtained analogously:

| Ex. | Starting material 1 | Product |
| --- | --- | --- |
| 6b | | 1153-85-1 |
| 6c | | 57102-42-8 |
| 6d | | 499128-71-1 |
| 6e | | 71041-21-9 |

-continued
| | | | |
|---|---|---|---|
| 6f | 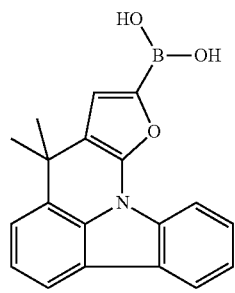 [SMILES: CC1(C)c2cc(B(O)O)oc2-n2c3ccccc3c3cccc1c32] | 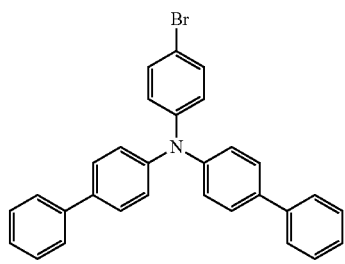 [SMILES: Brc1ccc(N(c2ccc(-c3ccccc3)cc2)c2ccc(-c3ccccc3)cc2)cc1] 499128-71-1 | |
| 6g | 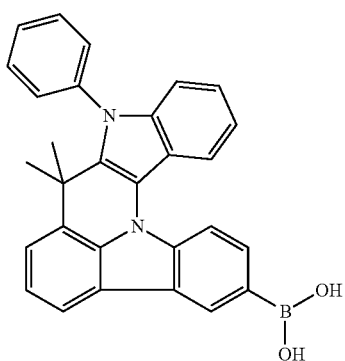 [SMILES: CC1(C)c2cccc3c4cc(B(O)O)ccc4n(c23)-c2c1n(-c1ccccc1)c1ccccc21] | 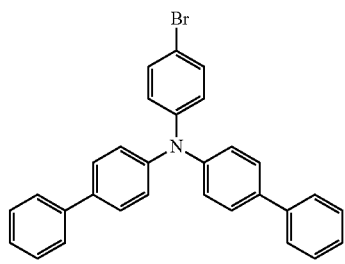 [SMILES: Brc1ccc(N(c2ccc(-c3ccccc3)cc2)c2ccc(-c3ccccc3)cc2)cc1] 499128-71-1 | |
| 6h | 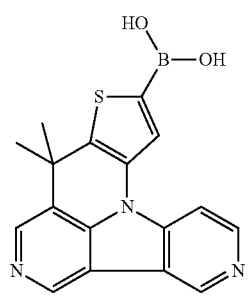 [SMILES: CC1(C)c2sc(B(O)O)cc2-n2c3ccncc3c3cncc1c32] | 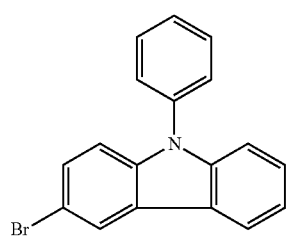 [SMILES: Brc1ccc2c(c1)c1ccccc1n2-c1ccccc1] 1153-85-1 | |
| 6i | 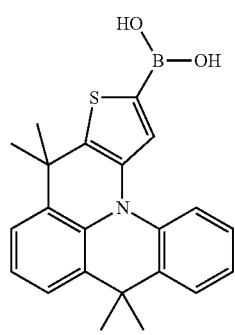 [SMILES: CC1(C)c2ccccc2N2c3cc(B(O)O)sc3C(C)(C)c3cccc1c32] | 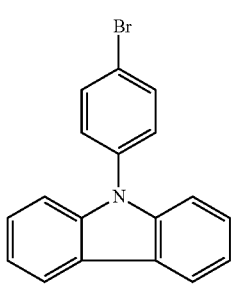 [SMILES: Brc1ccc(-n2c3ccccc3c3ccccc32)cc1] 57102-42-8 | |
| 6j | 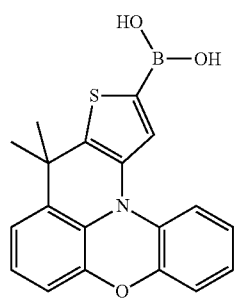 [SMILES: CC1(C)c2cccc3c2N(c2ccccc2O3)c2cc(B(O)O)sc21] | 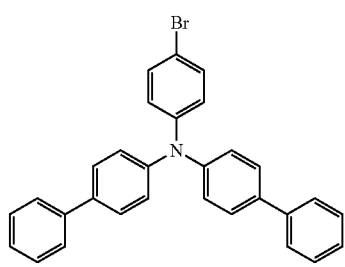 [SMILES: Brc1ccc(N(c2ccc(-c3ccccc3)cc2)c2ccc(-c3ccccc3)cc2)cc1] 499128-71-1 | |

| Ex. | Product | Yield |
|---|---|---|
| 6b | 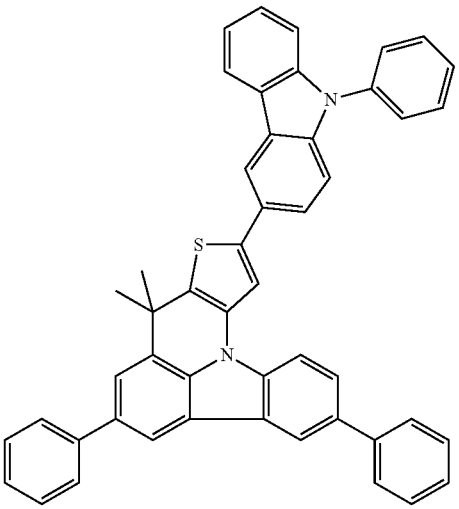 [SMILES: CC1(C)c2sc(-c3ccc4c(c3)c3ccccc3n4-c3ccccc3)cc2-n2c3ccc(-c4ccccc4)cc3c3cc(-c4ccccc4)cc1c32] | 81% |
| 6c | 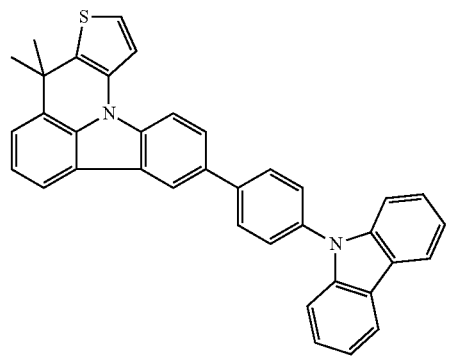 [SMILES: CC1(C)c2sccc2-n2c3ccc(-c4ccc(-n5c6ccccc6c6ccccc65)cc4)cc3c3cccc1c32] | 84% |
| 6d | 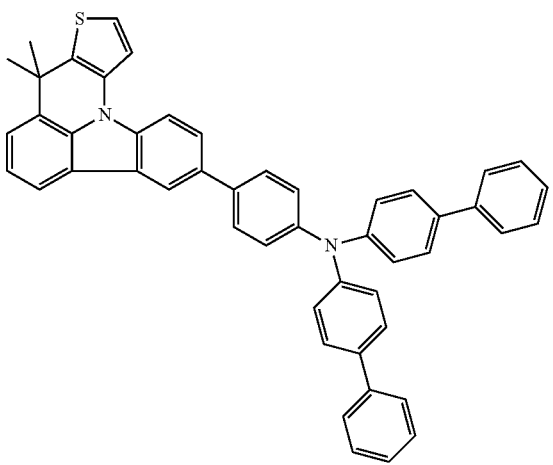 [SMILES: CC1(C)c2sccc2-n2c3ccc(-c4ccc(N(c5ccc(-c6ccccc6)cc5)c5ccc(-c6ccccc6)cc5)cc4)cc3c3cccc1c32] | 79% |

-continued
| | | |
|---|---|---|
| 6e | 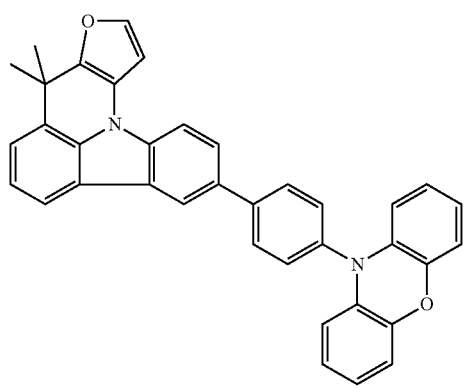 [SMILES: CC1(C)c2occc2-n2c3ccc(-c4ccc(N5c6ccccc6Oc6ccccc65)cc4)cc3c3cccc1c32] | 83% |
| 6f | 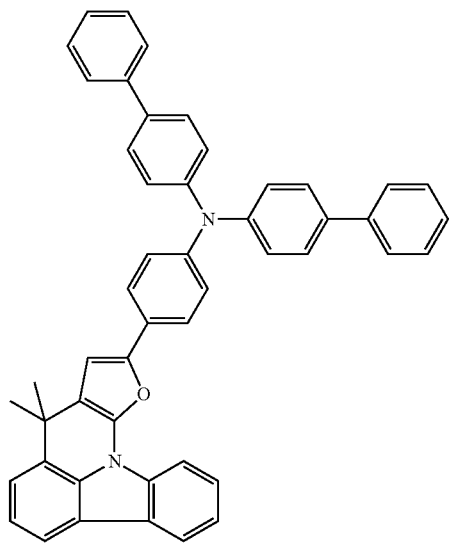 [SMILES: CC1(C)c2cc(-c3ccc(N(c4ccc(-c5ccccc5)cc4)c4ccc(-c5ccccc5)cc4)cc3)oc2-n2c3ccccc3c3cccc1c32] | 67% |
| 6g | 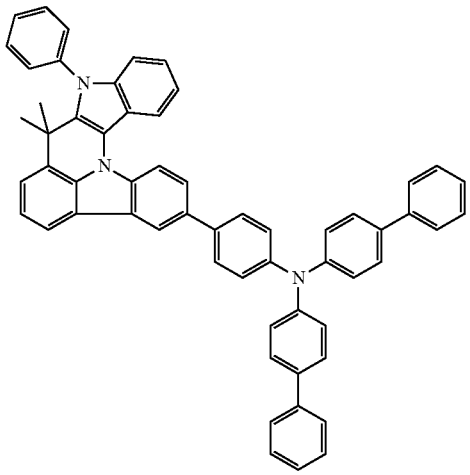 [SMILES: CC1(C)c2cccc3c4cc(-c5ccc(N(c6ccc(-c7ccccc7)cc6)c6ccc(-c7ccccc7)cc6)cc5)ccc4n(c23)-c2c1n(-c1ccccc1)c1ccccc21] | 77% |

| | | |
|---|---|---|
| 6h | 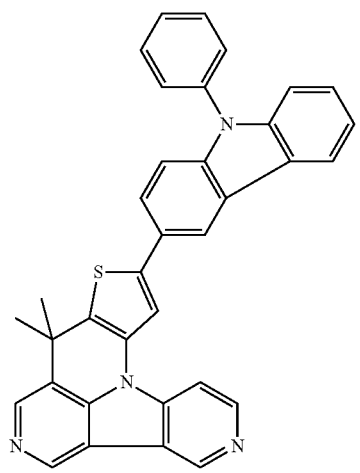 [SMILES: CC1(C)c2sc(-c3ccc4c(c3)c3ccccc3n4-c3ccccc3)cc2-n2c3ccncc3c3cncc1c32] | 71% |
| 6i | 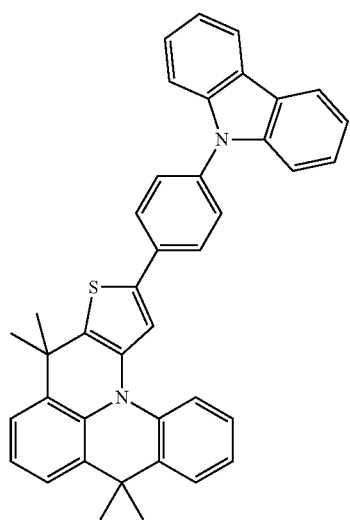 [SMILES: CC1(C)c2ccccc2N2c3cc(-c4ccc(-n5c6ccccc6c6ccccc65)cc4)sc3C(C)(C)c3cccc1c32] | 75% |
| 6j | 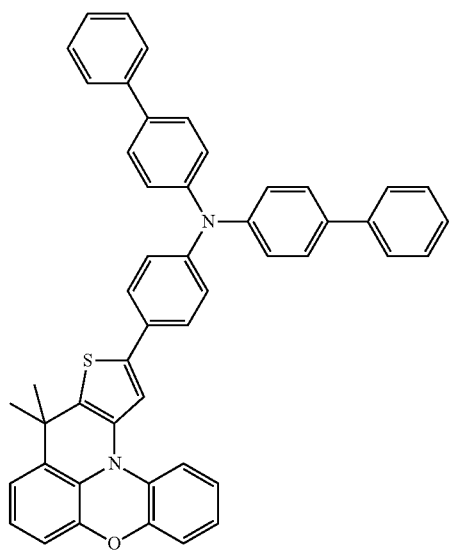 [SMILES: CC1(C)c2cccc3c2N(c2ccccc2O3)c2cc(-c3ccc(N(c4ccc(-c5ccccc5)cc4)c4ccc(-c5ccccc5)cc4)cc3)sc21] | 82% |

Example 7

Biphenyl-4-yl-(9,9-dimethyl-9H-fluoren-2-yl)-[4-(8,8-dimethyl-8H-9-thia-11b-azacyclopenta[a]fluoranthen-3-yl)phenyl]amine (Compound 7)

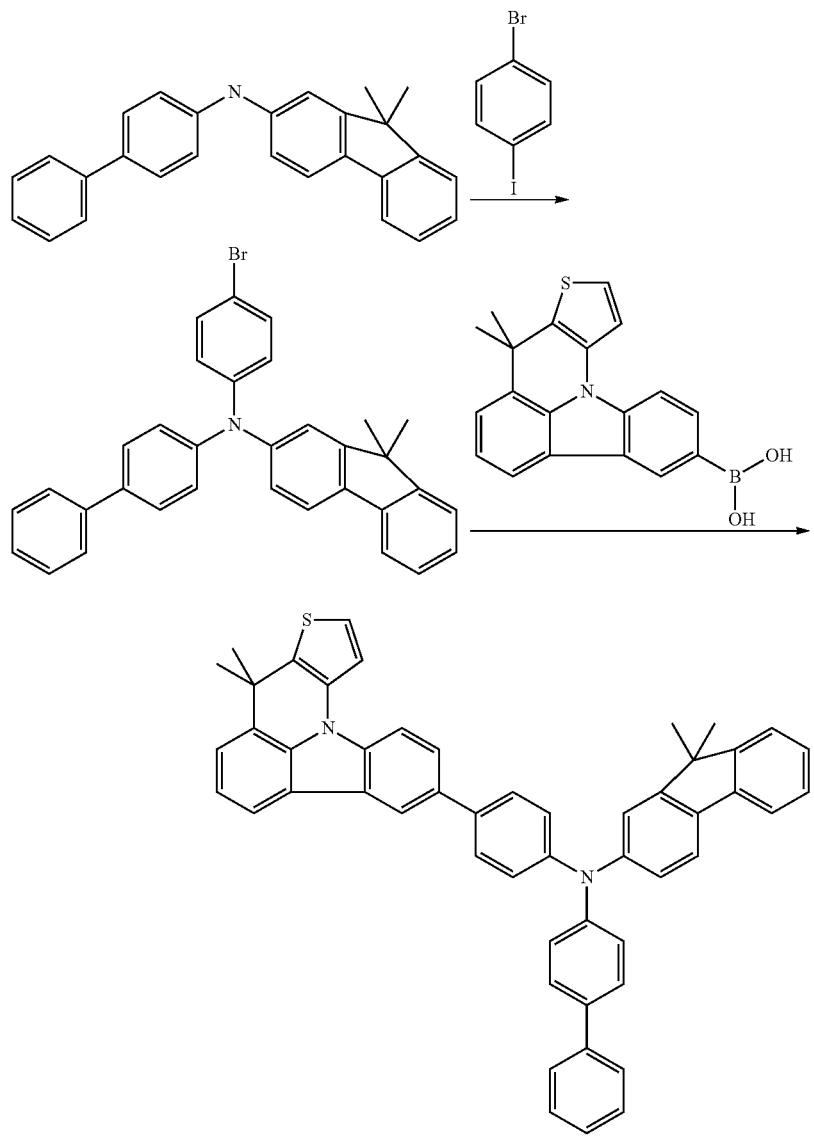

Step 1: Biphenyl-4-yl-(4-bromophenyl)-(9,9-dimethyl-9H-fluoren-2-yl)amine

A degassed solution of 490 mg (0.16 mmol) of copper(I) chloride and 906 mg (5 mmol) of 1,10-phenanthroline in 100 ml of toluene is saturated with $N_2$ for 1 h and heated to 130° C. 18 g (50 mmol) of N-[1,1-biphenyl]-4-yl-9,9-dimethyl-9H-fluoren-2-amine and 14 g (50 mmol) of 1-bromo-4-iodobenzene are subsequently added to the solution, and the mixture is heated at 180° C. for 2 h. After cooling, 180 ml of water are added to the mixture, the organic phase is separated off, and the solvent is removed in vacuo. The product is recrystallised from n-hexane. Yield: 15 g (29 mmol), 58% of theory, purity according to $^1$H-NMR about 98%.

Step 2: Biphenyl-4-yl-(9,9-dimethyl-9H-fluoren-2-yl)-[4-(8,8-dimethyl-8H-9-thia-11b-azacyclopenta[a]fluoranthen-3-yl)phenyl]amine The compound is synthesised in accordance with the same procedure as Example 6a by reaction of the corresponding 8,8-dimethyl-8H-9-thia-11b-azacyclopenta[a]fluoranthene-3-boronic acid with 56.8 g (110 mmol) of biphenyl-4-yl-(4-bromophenyl)-(9,9-dimethyl-9H-fluoren-2-yl)amine. The residue is recrystallised from ethyl acetate/heptane and finally sublimed in a high vacuum. Yield: 57 g (79 mmol), 72% of theory, purity according to HPLC 99.9%.

Example 8

5-[3-(4,6-Diphenylpyrimidin-2-yl)phenyl]-10,10-dimethyl-5,5a,9a,10-tetrahydro-1'-thia-5-azabenzo[b]fluorene (Compound 8)

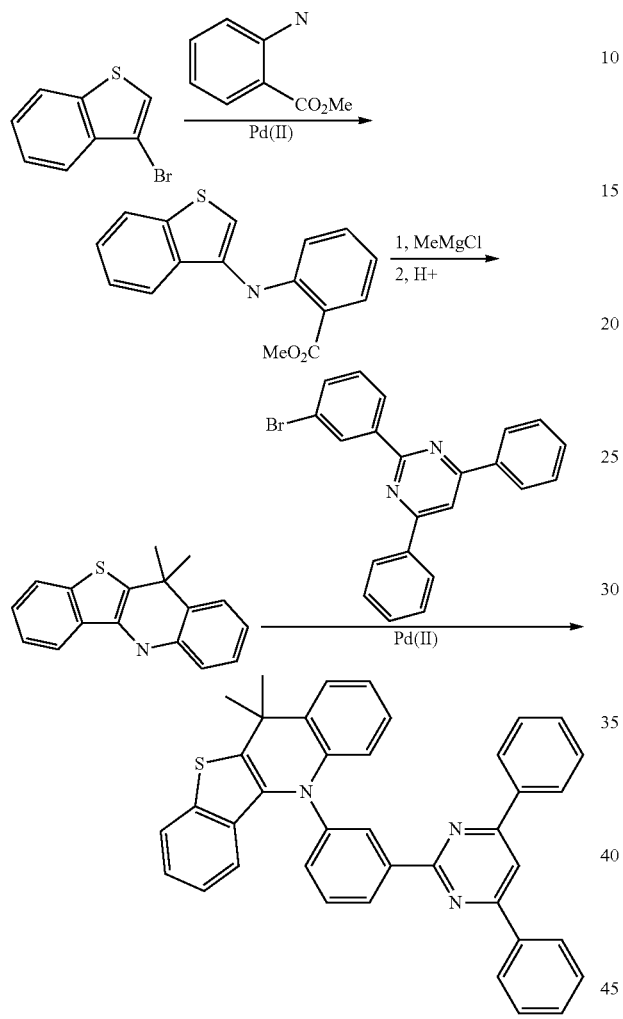

Step 1: Methyl 2-(benzo[b]thiophen-3-ylamino)benzoate 40 g (187.7 mmol) of 3-bromobenzothiophene, 24.25 ml (187.7 mmol) of 2-methyl anthranilate, and 122 g (375 mmol) of $Cs_2CO_3$ are suspended in 600 ml of toluene. 2.10 g (9.38 mmol) of palladium acetate and 3.69 g of xantphos (18.77 mmol) are added to this suspension. The reaction mixture is heated under reflux for 24 h. After cooling, the mixture is evaporated and subsequently partitioned between ethyl acetate and water. The organic phase is washed three times with water and dried over $Na_2SO_4$, evaporated in a rotary evaporator and subsequently evaporated to dryness. The residue is recrystallised from heptane. Yield: 32 g (60%)

Step 2: 10,10-Dimethyl-5,5a,9a,10-tetrahydro-11-thia-5-azabenzo[b]-fluorene 25.9 g (105 mmol) of anhydrous cerium(III) chloride are initially introduced in 400 ml of dry THF. 30 g (105 mmol) of methyl 2-(benzo[b]thiophen-3-ylamino)benzoate are metered into this solution in portions, and the mixture is stirred for 1 h. The reaction mixture is cooled, and 140 ml (420 mmol) of methylmagnesium chloride solution (3 mol/l in THF) are added dropwise over the course of 40 min at 5° C. After one hour, the reaction mixture is carefully poured onto ice and extracted three times with dichloromethane. The combined organic phases are dried over $Na_2SO_4$ and evaporated. The residue is recrystallised from toluene. Yield: 29.5 g (95%)

35.60 g (309 mmol) of polyphosphoric acid and 20 ml (309 mmol) of methanesulfonic acid are initially introduced in 300 ml of $CH_2Cl_2$. 25 g (88 mmol) of 2-[2-(benzo[b]thiophen-3-ylamino)phenyl]propan-2-ol in $CH_2Cl_2$ solution (100 ml) are added dropwise to this solution over the course of 30 min, and the mixture is stirred at room temperature for 1 h. The reaction mixture is cooled, carefully poured onto ice and extracted three times with dichloromethane. The combined organic phases are dried over $Na_2SO_4$ and evaporated. The residue is recrystallised from toluene. Yield: 20 g of 10,10-dimethyl-5,5a,9a,10-tetrahydro-1'-thia-5-azabenzo[b]-fluorene (85%).

Step 3: 5-[3-(4,6-Diphenylpyrimidin-2-yl)phenyl]-10,10-dimethyl-5,5a,9a,10-tetrahydro-1'-thia-5-azabenzo[b]fluorene 18 g (68 mmol) of 10,10-dimethyl-5,5a,9a,10-tetrahydro-1'-thia-5-azabenzo[b]fluorene, 28.9 g (75 mmol) of 2-(3-bromophenyl)-4,6-diphenylpyrimidine and 19.6 g of NaOtBu (203 mmol) are suspended in 500 ml of p-xylene. 0.3 g (1.36 mmol) of $Pd(OAc)_2$ and 2.7 ml of a 1M tri-tert-butylphosphine solution are added to this suspension. The reaction mixture is heated under reflux for 16 h. After cooling, the organic phase is separated off washed three times with 200 ml of water and subsequently evaporated to dryness. The residue is extracted with hot toluene and recrystallised from toluene and finally sublimed in a high vacuum, purity is 99.9%.

Example 9

5,10-Bisbiphenyl-4-yl-11,11-dimethyl-10,11-dihydro-5H-indolo[3,2-b]quinoline (Compound 9)

Step 1: Methyl 2-(1-biphenyl-4-yl-1H-indol-3-ylamino)benzoate

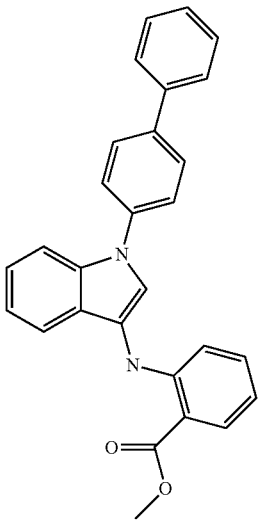 [SMILES: COC(=O)c1ccccc1Nc1cn(-c2ccc(-c3ccccc3)cc2)c2ccccc12]

25 g (213 mmol) of 1H-indole, 89.6 g (320 mmol) of monoiodobiphenyl and 100 g of $K_3PO_4$ are suspended in 1 l of toluene. 16.3 g (85 mmol) of CuI and 7.5 g of N,N'-dimethylenediamine (85 mmol) are added to this suspension. The reaction mixture is heated under reflux for 48 h. After cooling, the precipitate is filtered off via a fluted filter. The reaction solution was subsequently partitioned between ethyl acetate and water, the organic phase was washed three times with water, dried over $Na_2SO_4$, evaporated in a rotary evaporator, the organic phase was separated off, washed three times with 200 ml of water and subsequently evaporated to dryness. The black-green oil remaining was filtered through silica gel with heptane:toluene. The evaporated filtrate residue was recrystallised from methanol. Yield: 41 g of 1-biphenyl-4-yl-1H-indole (70%).

40 g (149 mmol) of 1-biphenyl-4-yl-1H-indole are initially introduced in 500 ml of dichloromethane. A solution of 26.4 g (149 mmol) of NBS in 200 ml of dichloromethane is subsequently added dropwise at 0° C. with exclusion of light, the mixture is allowed to come to room temperature and is stirred for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction. Yield: 49.1 g (95%).

49 g (141 mmol) of 1-biphenyl-4-yl-3-bromo-1H-indole, 18 ml (141 mmol) of 2-methyl anthranilate and 91.7 g (281 mmol) of $Cs_2CO_3$ are suspended in 800 ml of toluene. 0.8 g (3.52 mmol) of palladium acetate and 4 g of xantphos (7.04 mmol) are added to this suspension. The reaction mixture is heated under reflux for 24 h. After cooling, the mixture is evaporated and subsequently partitioned between ethyl acetate and water. The organic phase is washed three times with water, dried over $Na_2SO_4$, evaporated in a rotary evaporator, organic phase is separated off, washed three times with 200 ml of water and subsequently evaporated to dryness. The residue is recrystallised from heptane. Yield: 53 g (90%)

Step 2: 10-Biphenyl-4-yl-11,11-dimethyl-10,11-dihydro-5H-indolo-[3,2-b]quinoline

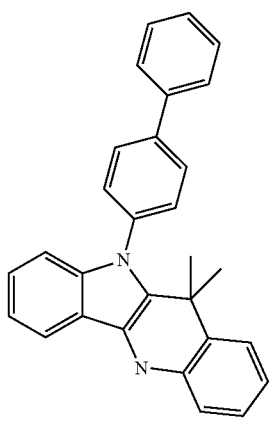 [SMILES: CC1(C)c2ccccc2Nc2c1n(-c1ccc(-c3ccccc3)cc1)c1ccccc21]

22.8 g (92 mmol) of anhydrous cerium(III) chloride are initially introduced in 700 ml of dry THF. 35 g (84 mmol) of methyl 2-(1-biphenyl-4-yl-1H-indol-3-ylamino)benzoate are metered into this solution in portions, and the mixture is stirred for 1 h. The reaction mixture is cooled, and 117 ml (351 mmol) of methylmagnesium chloride solution (3 mol/l in THF) are added dropwise over the course of 40 min at 5° C. After one hour, the reaction mixture is carefully poured onto ice and extracted three times with dichloromethane. The combined organic phases are dried over $Na_2SO_4$ and evaporated. The residue is recrystallised from toluene. Yield: 32.9 g (94%)

28.9 g (250.9 mmol) of polyphosphoric acid and 16.5 ml of methanesulfonic acid are initially introduced in 200 ml of $CH_2Cl_2$. 30 g (72 mmol) of 2-[2-(1-biphenyl-4-yl-1H-indol-3-ylamino)phenyl]propan-2-ol in $CH_2Cl_2$ solution (50 ml) are added dropwise to this solution over the course of 30 min, and the mixture is stirred at 50° C. for 1 h. After this time, the reaction mixture is cooled, 150 ml of ethanol are carefully added, and the mixture is extracted three times with dichloromethane. The combined organic phases are dried over $Na_2SO_4$ and evaporated. Yield: 24.4 g of 10-biphenyl-4-yl-11,11-dimethyl-10,11-dihydro-5H-indolo[3,2-b]quinoline (85%).

Step 3: 5,10-Bisbiphenyl-4-yl-11,11-dimethyl-10,11-dihydro-5H-indolo[3,2-b]quinoline

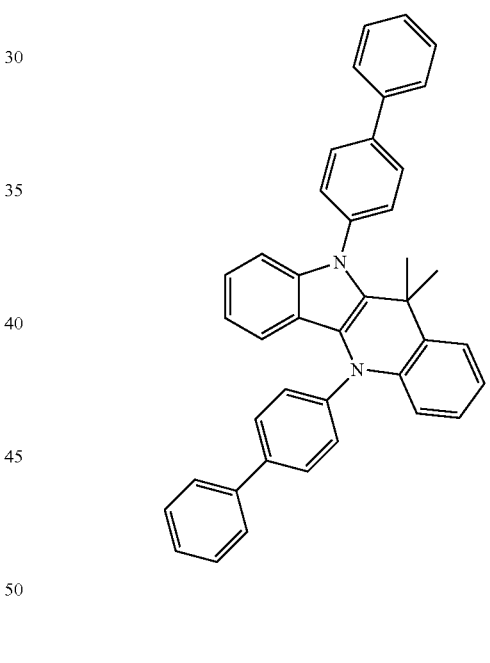

24 g (60 mmol) of the indoloquinoline derivative, 15.4 g (66 mmol) of bromobiphenyl and 16.6 g (191.7 mmol) of NaOtBu are suspended in 500 ml of toluene. 0.34 g (1.5 mmol) of $Pd(OAc)_2$ and 3 ml of a 1M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, purity is 99.9%.

Example 10

Compound 10

Step 1: Methyl 1-phenyl-3-(pyren-1-ylamino)-1H-indole-2-carboxylate

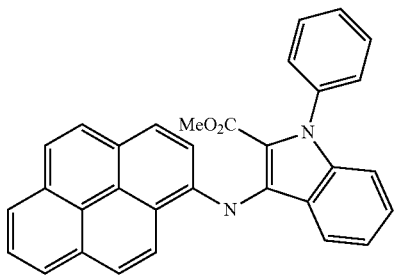 [SMILES: COC(=O)c1c(Nc2ccc3ccc4cccc5ccc2c3c45)c2ccccc2n1-c1ccccc1]

25 g (99 mmol) of methyl 1-phenyl-1H-indole-2-carboxylate are initially introduced in 400 ml of dichloromethane. A solution of 17.7 g (99 mmol) of NBS in 100 ml of dichloromethane is subsequently added dropwise at 0° C. with exclusion of light, the mixture is allowed to come to room temperature and is stirred for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction. Yield: 32 g, (95%)

30 g (91 mmol) of methyl 1-phenyl-3-bromo-1H-indole-2-carboxylate, 10.7 g (91 mmol) of aminopyrene and 59.2 g (181 mmol) of $Cs_2CO_3$ are suspended in 800 ml of toluene. 0.5 g (2.27 mmol) of palladium acetate and 2.6 g (4.54 mmol) of xantphos are added to this suspension. The reaction mixture is heated under reflux for 24 h. After cooling, the mixture is evaporated and subsequently partitioned between ethyl acetate and water. The organic phase is washed three times with water, dried over $Na_2SO_4$, evaporated in a rotary evaporator, organic phase is separated off, washed three times with 200 ml of water and subsequently evaporated to dryness. The residue is recrystallised from heptane. Yield: 36 g (85%).

Step 2

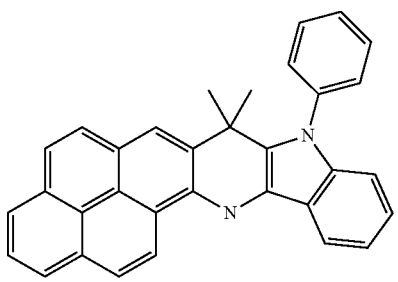 [SMILES: CC1(C)c2cc3ccc4cccc5ccc(c2Nc2c1n(-c1ccccc1)c1ccccc21)c3c45]

21.03 g (84.9 mmol) of anhydrous cerium(III) chloride are initially introduced in 700 ml of dry THF. 36 g (84 mmol) of methyl 1-phenyl-3-(pyren-1-ylamino)-1H-indole-2-carboxylate are metered into this solution in portions, and the mixture is stirred for 1 h. The reaction mixture is cooled, and 108 ml (324 mmol) of methylmagnesium chloride solution (3 mol/l in THF) are added dropwise over the course of 40 min at 5° C. After 1 h, the reaction mixture is carefully poured onto ice and extracted three times with dichloromethane. The combined organic phases are dried over $Na_2SO_4$ and evaporated. The residue is recrystallised from toluene. Yield: 34.2 g (95%)

26 g (225 mmol) of polyphosphoric acid and 14.8 ml (225 mmol) of methanesulfonic acid are initially introduced in 200 ml of $CH_2Cl_2$. 30 g (54 mmol) of 2-[1-phenyl-3-(pyren-1-ylamino)-1H-indol-2-yl]propan-2-ol in $CH_2Cl_2$ solution (100 ml) are added dropwise to this solution over the course of 30 min, and the mixture is stirred at 50° C. for 1 h. After this time, the reaction mixture is cooled, 150 ml of ethanol are carefully added, and the mixture is extracted three times with dichloromethane. The combined organic phases are dried over $Na_2SO_4$ and evaporated. Yield: 27 g (76%)

Step 3

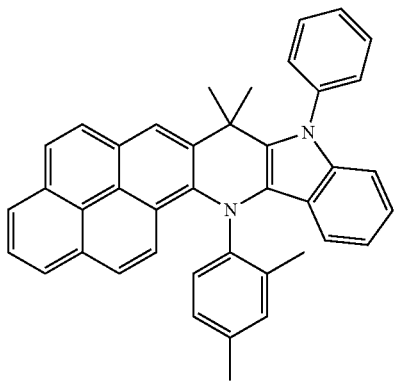 [SMILES: Cc1ccc(N2c3c(cc4ccc5cccc6ccc3c4c56)C(C)(C)c3c2c2ccccc2n3-c2ccccc2)c(C)c1]

25 g (56 mmol) of the indoloquinoline derivative, 11.3 g (61 mmol) of 1-bromo-2,4-dimethylphenyl and 175 g of NaOtBu (178.3 mmol) are suspended in 500 ml of toluene. 0.31 g (1.4 mmol) of $Pd(OAc)_2$ and 2.8 ml of a 1M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene and recrystallised from toluene and finally sublimed in a high vacuum, purity is 99.9%.

Example 11

Production of OLEDs

OLEDs according to the invention are produced by a general process in accordance with WO 2004/058911, which is adapted to the circumstances described here (layer-thickness variation, materials).

The data for various OLEDs are presented in Examples E1-E28 below (see Tables 1 and 2). Glass plates coated with structured ITO (indium tin oxide) in a thickness of 150 nm are coated with 20 nm of PEDOT (poly(3,4-ethylenedioxythiophene), applied by spin coating from water; purchased from H. C. Starck, Goslar, Germany) for improved processing. These coated glass plates form the substrates to which the OLEDs are applied. The OLEDs have in principle the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium cathode with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by coevaporation. An expression such as ST1:6b:TER1 (65%:20%:15%) here means that material ST1 is present in the layer in a proportion by volume of 65%, material 6b is present in the layer in a proportion of 20% and material TER1 is present in the layer in a proportion of 15%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), assuming Lambert emission characteristics, are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiencies achieved at 1000 cd/m$^2$. Finally, EQE1000 denotes the external quantum efficiency at an operating luminous density of 1000 cd/m$^2$.

The data for the various OLEDs are summarised in Table 2. The materials according to the invention can be employed in various layers depending on the substitution pattern. Very good values are achieved here for efficiency and voltage.

TABLE 1

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| E1 | HATCN 5 nm | SpA1 110 nm | — | NPB 20 nm | M2:D2 (90%:10%) 30 nm | — | 4b 20 nm | LiQ 3 nm |
| E2 | — | SpA1 20 nm | — | NPB 20 nm | ST1:4d:TER2 (65%:20%:15%) 30 nm | — | Alq$_3$ 20 nm | LiF 1 nm |
| E3 | — | SpA1 70 nm | HATCN 5 nm | BPA1 90 nm | 4e:TEG1 (90%:10%) 30 nm | — | ST2:LiQ (50%:50%) 40 nm | — |
| E4 | — | SpA1 70 nm | HATCN 5 nm | BPA1 90 nm | 4e:TEG1 (90%:10%) 30 nm | IC1 10 nm | ST2:LiQ (50%:50%) 30 nm | — |
| E5 | — | SpA1 70 nm | HATCN 5 nm | BPA1 90 nm | ST1:4l:TEG1 (30%:60%:10%) 30 nm | IC1 10 nm | ST2:LiQ (50%:50%) 30 nm | — |
| E6 | — | SpA1 70 nm | HATCN 5 nm | BPA1 90 nm | 4k:TEG1 (90%:10%) 30 nm | — | ST1:LiQ (50%:50%) 40 nm | — |
| E7 | — | SpA1 20 nm | — | NPB 20 nm | 4k:TER1 (85%:15%) 30 nm | — | Alq$_3$ 20 nm | LiF 1 nm |
| E8 | — | SpA1 20 nm | — | NPB 20 nm | 4m:TER1 (85%:15%) 30 nm | — | Alq$_3$ 20 nm | LiF 1 nm |
| E9 | — | SpA1 20 nm | — | 4n 20 nm | ST1:TER1 (85%:15%) 30 nm | — | Alq$_3$ 20 nm | LiF 1 nm |
| E10 | — | SpA1 70 nm | HATCN 5 nm | BPA1 20 nm | ST1:TEG1 (90%:10%) 30 nm | ST1 10 nm | 4o 30 nm | LiQ 3 nm |
| E11 | — | SpA1 20 nm | BPA1 10 nm | 4q 10 nm | ST1:TER1 (85%:15%) 30 nm | — | Alq$_3$ 20 nm | LiF 1 nm |
| E12 | — | SpA1 20 nm | — | NPB 20 nm | 5a:TER2 (85%:15%) 30 nm | — | Alq$_3$ 20 nm | LiF 1 nm |
| E13 | — | SpA1 70 nm | HATCN 5 nm | BPA1 90 nm | IC1:6a:TEG1 (60%:30%:10%) 30 nm | IC1 10 nm | ST2:LiQ (50%:50%) 30 nm | — |
| E14 | — | SpA1 20 nm | — | NPB 20 nm | ST1:6b:TER1 (65%:20%:15%) 30 nm | ST1 10 nm | Alq$_3$ 20 nm | LiF 1 nm |
| E15 | — | SpA1 70 nm | HATCN 5 nm | BPA1 90 nm | IC1:6c:TEG1 (45%:45%:10%) 30 nm | IC1 10 nm | ST2:LiQ (50%:50%) 30 nm | — |
| E16 | — | SpA1 70 nm | HATCN 5 nm | 6d 20 nm | ST1:TEG1 (90%:10%) 30 nm | — | ST1:LiQ (50%:50%) 30 nm | — |
| E17 | HATCN 5 nm | SpA1 110 nm | — | 6d 20 nm | M2:D2 (90%:10%) 30 nm | — | Alq$_3$ 20 nm | LiF 1 nm |
| E18 | — | SpA1 140 nm | HATCN 5 nm | 6d 20 nm | M1:D1 (95%:5%) 20 nm | — | Alq3 30 nm | LiF 1 nm |
| E19 | — | SpA1 70 nm | HATCN 5 nm | BPA1 90 nm | ST1:6e:TEG1 (50%:40%:10%) 30 nm | — | ST1:LiQ (50%:50%) 40 nm | — |
| E20 | — | 6f 20 nm | — | NPB 20 nm | ST1:TER2 (85%:15%) 30 nm | — | Alq$_3$ 20 nm | LiF 1 nm |
| E21 | — | 6g 20 nm | — | NPB 20 nm | ST1:TER2 (85%:15%) 30 nm | — | Alq$_3$ 20 nm | LiF 1 nm |
| E22 | — | SPA1 20 nm | — | NPB 20 nm | 6h:TER2 (85%:15%) 30 nm | — | Alq$_3$ 20 nm | LiF 1 nm |
| E23 | — | SpA1 20 nm | — | NPB 20 nm | ST1:6i:TER2 (70%:15%:15%) 30 nm | ST2 5 nm | ST2:LiQ (50%:50%) 25 nm | — |
| E24 | — | SpA1 20 nm | — | 6j 20 nm | ST1:TER1 (85%:15%) 30 nm | — | Alq$_3$ 20 nm | LiF 1 nm |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| E25 | — | 9 20 nm | — | NPB 20 nm | ST1:TER2 (85%:15%) 30 nm | — | Alq$_3$ 20 nm | LiF 1 nm |
| E26 | — | SpA1 70 nm | HATCN 5 nm | BPA1 90 nm | 8a:TEG1 (90%:10%) 30 nm | IC1 10 nm | ST1:LiQ (50%:50%) 30 nm | — |
| E27 | — | SpA1 70 nm | HATCN 5 nm | BPA1 90 nm | 8a:IC2:TEG1 (20%:70%:10%) 30 nm | IC1 10 nm | ST1:LiQ (50%:50%) 30 nm | — |
| E28 | HATCN 5 nm | SpA1 140 nm | — | NPB 20 nm | M2:10 (97%:3%) 20 nm | — | ST2:LiQ (50%:50%) 30 nm | — |

TABLE 2

Data of the OLEDs

| Ex. | U1000 (V) | CE1000 (cd/A) | PE1000 (lm/W) | EQE 1000 | CIE x/y |
|---|---|---|---|---|---|
| E1 | 5.4 | 17.7 | 10.3 | 5.2% | 0.29/0.61 |
| E2 | 5.6 | 11.3 | 6.4 | 10.5% | 0.66/0.33 |
| E3 | 3.8 | 50 | 41 | 13.8% | 0.36/0.61 |
| E4 | 3.9 | 52 | 41 | 14.3% | 0.36/0.61 |
| E5 | 3.6 | 46 | 41 | 12.8% | 0.36/0.61 |
| E6 | 3.5 | 54 | 50 | 15.0% | 0.36/0.61 |
| E7 | 4.8 | 7.6 | 5.0 | 12.9% | 0.69/0.31 |
| E8 | 4.6 | 5.5 | 3.8 | 9.4% | 0.69/0.31 |
| E9 | 5.4 | 6.6 | 3.8 | 10.8% | 0.69/0.31 |
| E10 | 4.5 | 49 | 34 | 13.6% | 0.36/0.59 |
| E11 | 5.2 | 6.7 | 4.1 | 11.3% | 0.69/0.31 |
| E12 | 7.2 | 7.2 | 3.1 | 6.6% | 0.66/0.33 |
| E13 | 3.4 | 47 | 43 | 15.7% | 0.69/0.60 |
| E14 | 4.0 | 7.7 | 6.1 | 12.9% | 0.69/0.31 |
| E15 | 3.7 | 51 | 43 | 14.2% | 0.36/0.61 |
| E16 | 4.0 | 52 | 42 | 14.6% | 0.37/0.60 |
| E17 | 5.0 | 18.8 | 11.9 | 5.5% | 0.28/0.61 |
| E18 | 6.3 | 6.2 | 3.1 | 5.1% | 0.14/0.15 |
| E19 | 3.3 | 47 | 44 | 13.0% | 0.36/0.61 |
| E20 | 6.6 | 9.3 | 4.5 | 8.6% | 0.66/0.33 |
| E21 | 6.2 | 8.9 | 4.5 | 8.2% | 0.66/0.33 |
| E22 | 6.9 | 8.2 | 3.7 | 7.6% | 0.66/0.33 |
| E23 | 5.9 | 10.7 | 5.7 | 9.9% | 0.66/0.33 |
| E24 | 5.1 | 7.8 | 4.8 | 13.0% | 0.69/0.31 |
| E25 | 6.4 | 9.6 | 4.7 | 8.8% | 0.66/0.33 |
| E26 | 3.5 | 52 | 47 | 14.4% | 0.36/0.60 |
| E27 | 3.6 | 55 | 48 | 15.3% | 0.36/0.61 |
| E28 | 4.5 | 6.5 | 4.6 | 5.4% | 0.14/0.15 |

TABLE 3

Structural formulae of the materials for the OLEDs

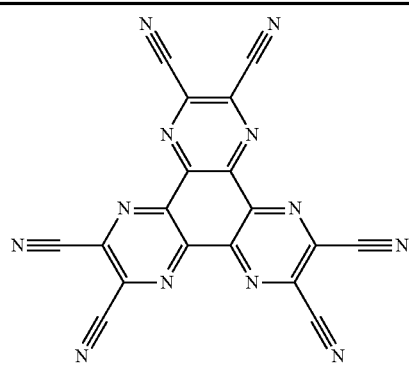

HATCN

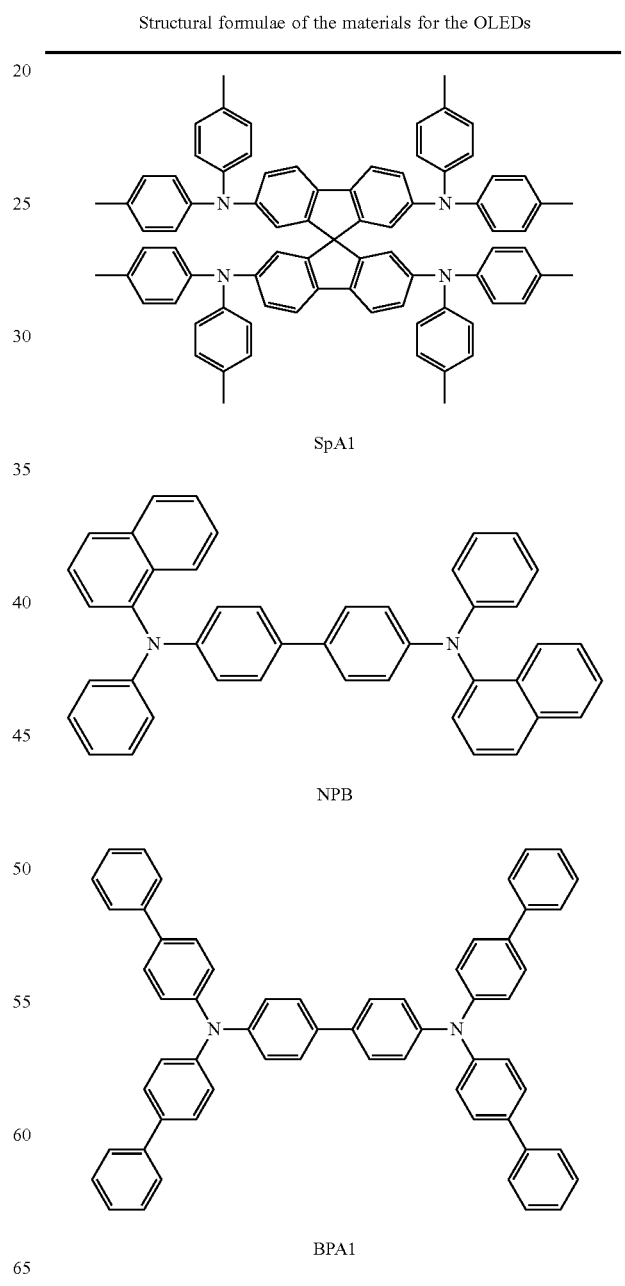

SpA1

NPB

BPA1

TABLE 3-continued
Structural formulae of the materials for the OLEDs
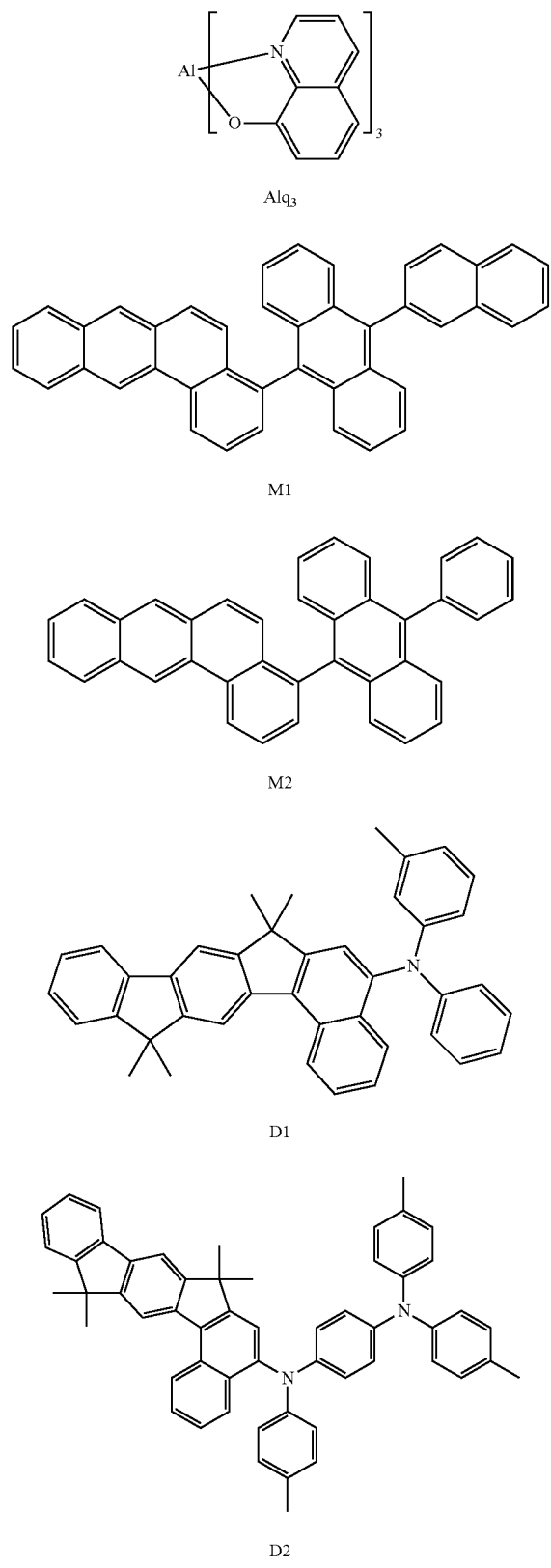
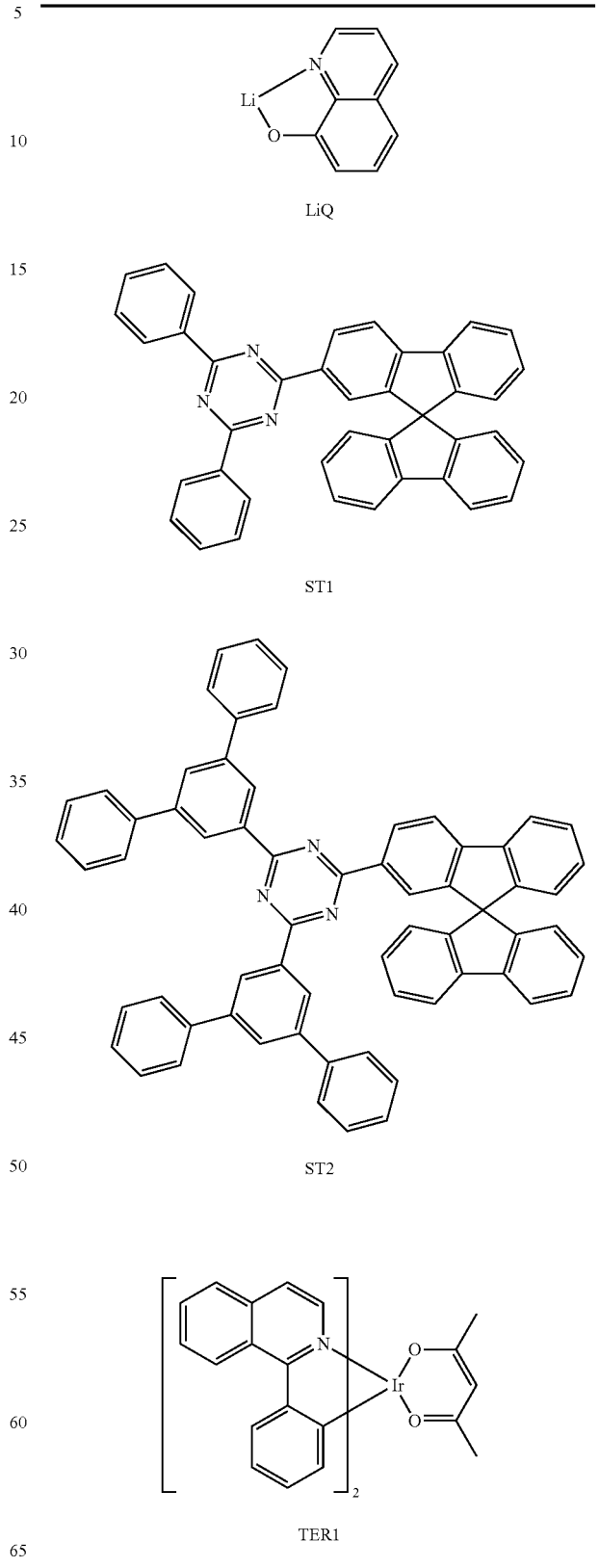

TABLE 3-continued
Structural formulae of the materials for the OLEDs
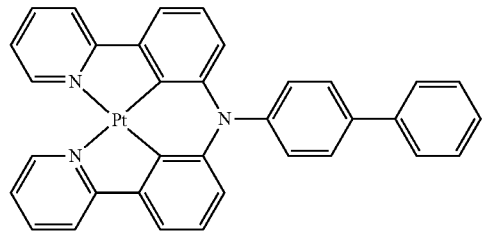
TER2
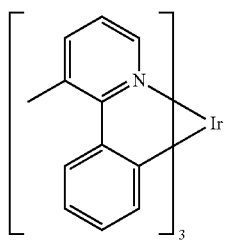
TEG1
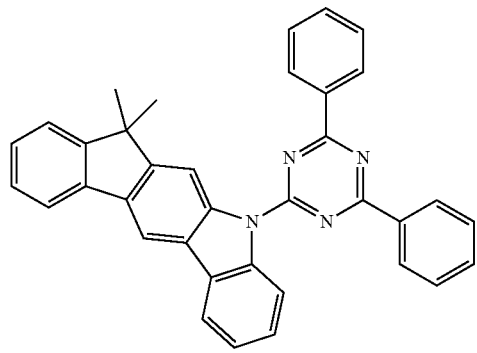 [SMILES: CC1(C)c2ccccc2-c2cc3c4ccccc4n(-c4nc(-c5ccccc5)nc(-c5ccccc5)n4)c3cc21]
IC1
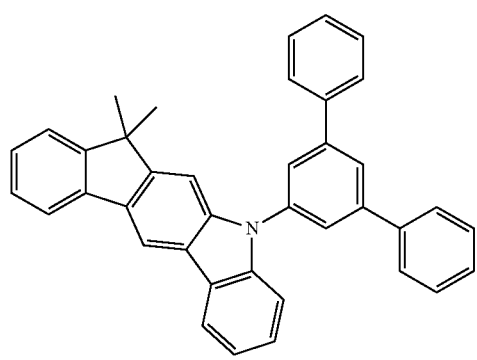 [SMILES: CC1(C)c2ccccc2-c2cc3c4ccccc4n(-c4cc(-c5ccccc5)cc(-c5ccccc5)c4)c3cc21]
IC2
TABLE 3-continued
Structural formulae of the materials for the OLEDs
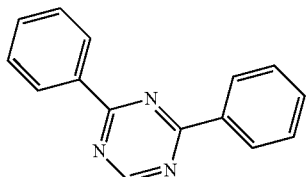
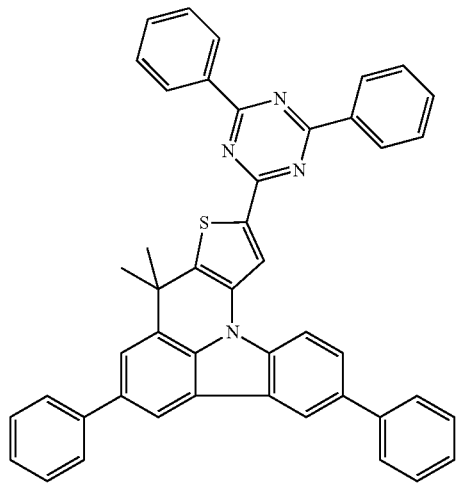 [SMILES: CC1(C)c2sc(-c3nc(-c4ccccc4)nc(-c4ccccc4)n3)cc2-n2c3ccc(-c4ccccc4)cc3c3cc(-c4ccccc4)cc1c32]
4b
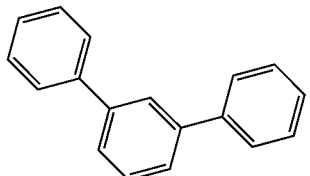
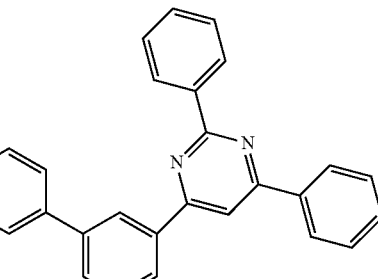
4d
4e TABLE 3-continued
Structural formulae of the materials for the OLEDs
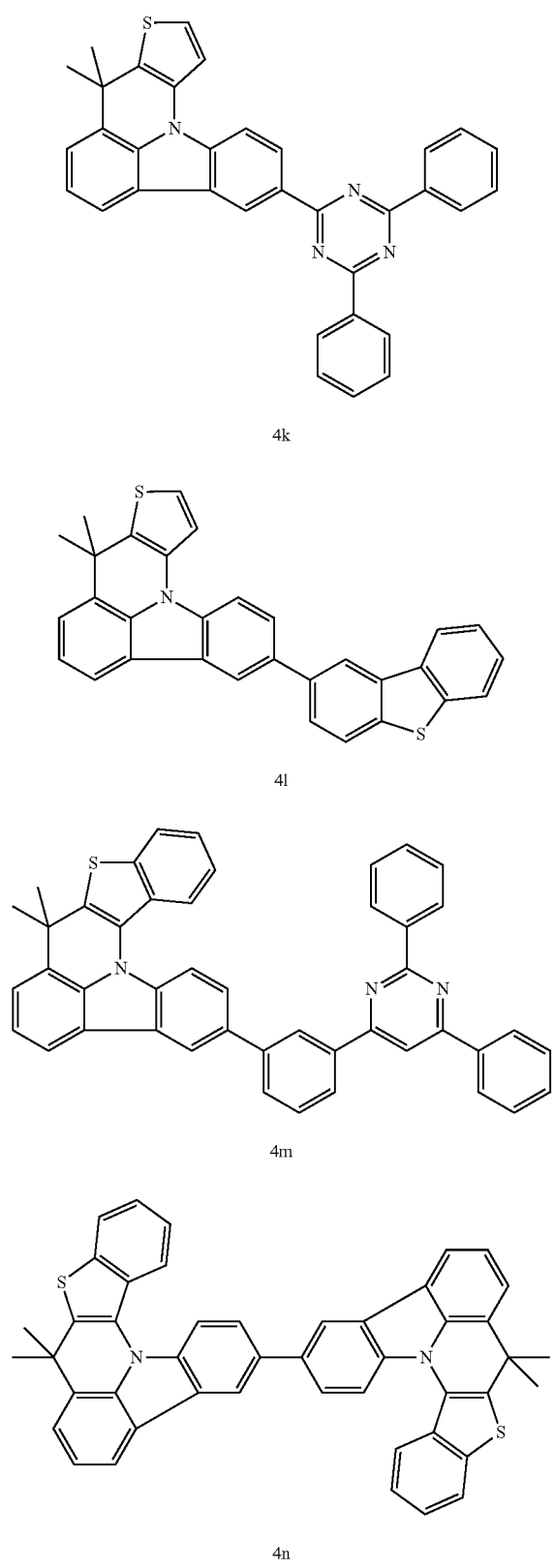
4k
4l
4m
4n
TABLE 3-continued
Structural formulae of the materials for the OLEDs
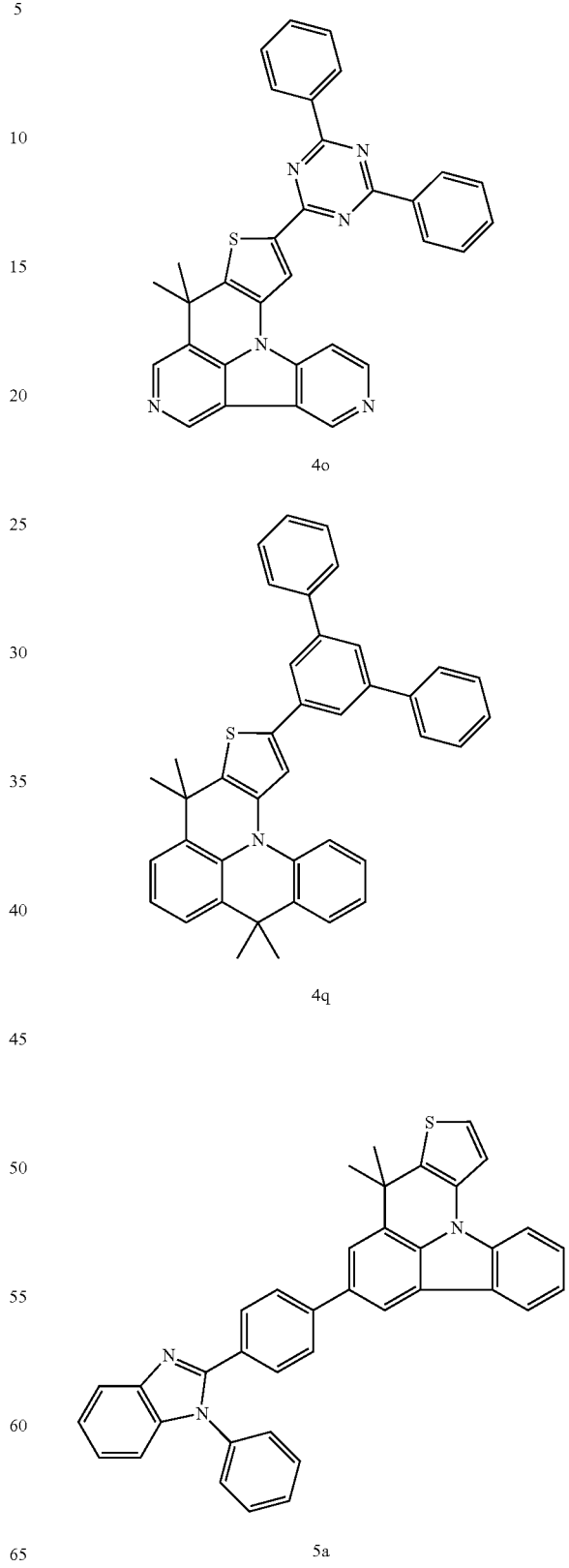
4o
4q
5a TABLE 3-continued
Structural formulae of the materials for the OLEDs
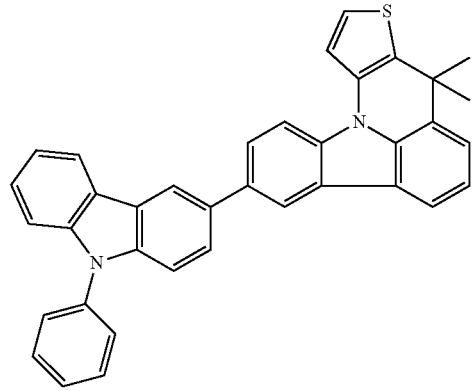 [SMILES: CC1(C)c2sccc2-n2c3ccc(-c4ccc5c(c4)c4ccccc4n5-c4ccccc4)cc3c3cccc1c32]
6a
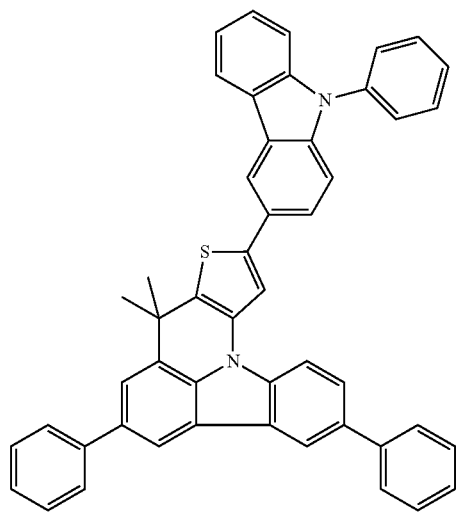 [SMILES: CC1(C)c2sc(-c3ccc4c(c3)c3ccccc3n4-c3ccccc3)cc2-n2c3ccc(-c4ccccc4)cc3c3cc(-c4ccccc4)cc1c32]
6b
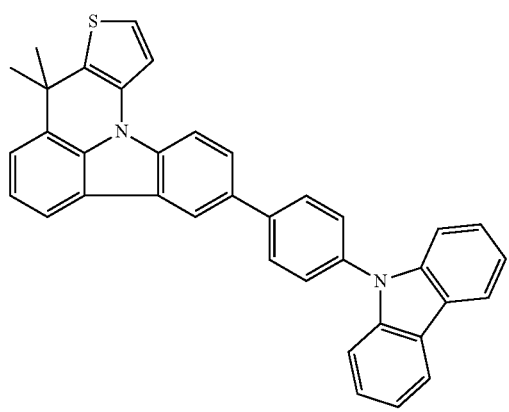 [SMILES: CC1(C)c2sccc2-n2c3ccc(-c4ccc(-n5c6ccccc6c6ccccc65)cc4)cc3c3cccc1c32]
6c
TABLE 3-continued
Structural formulae of the materials for the OLEDs
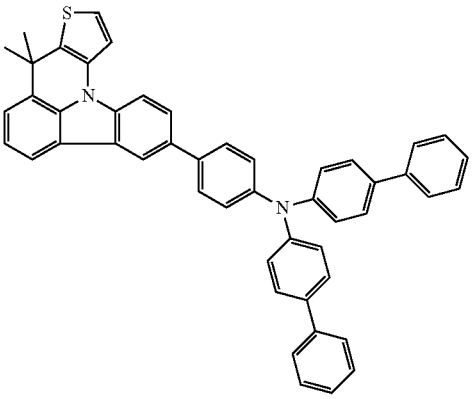 [SMILES: CC1(C)c2sccc2-n2c3ccc(-c4ccc(N(c5ccc(-c6ccccc6)cc5)c5ccc(-c6ccccc6)cc5)cc4)cc3c3cccc1c32]
6d
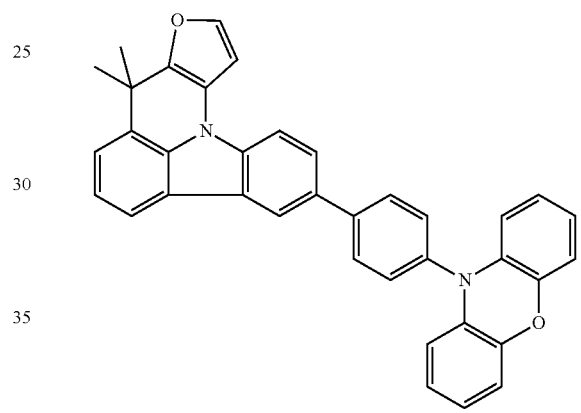
6e
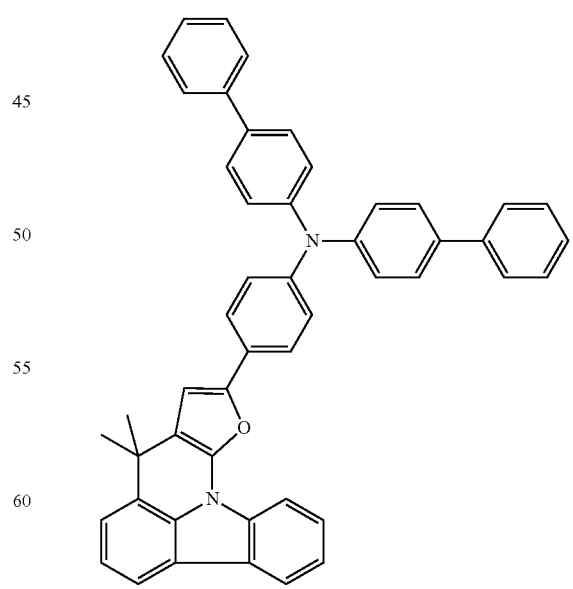
6f TABLE 3-continued
Structural formulae of the materials for the OLEDs
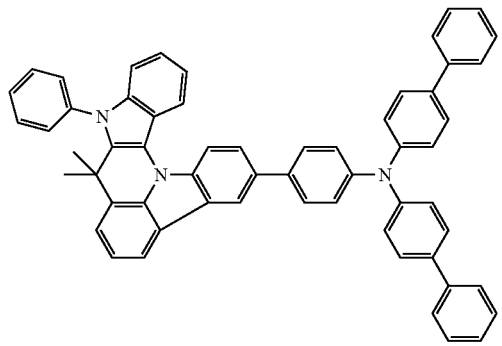 [SMILES: CC1(C)c2cccc3c4cc(-c5ccc(N(c6ccc(-c7ccccc7)cc6)c6ccc(-c7ccccc7)cc6)cc5)ccc4n(c23)-c2c1n(-c1ccccc1)c1ccccc21]
6g
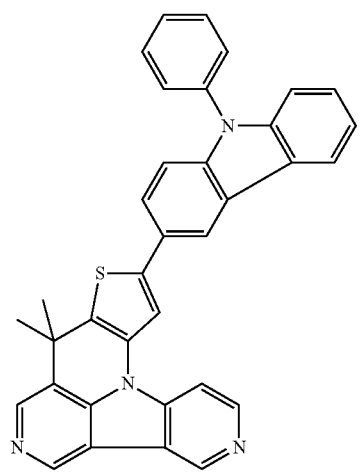 [SMILES: CC1(C)c2sc(-c3ccc4c(c3)c3ccccc3n4-c3ccccc3)cc2-n2c3ccncc3c3cncc1c32]
6h
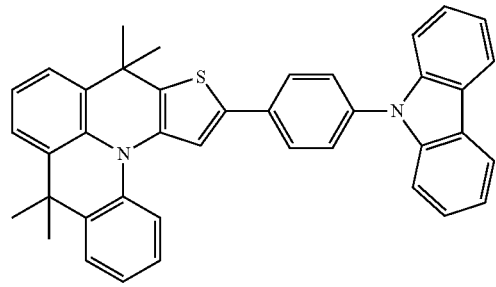 [SMILES: CC1(C)c2ccccc2N2c3cc(-c4ccc(-n5c6ccccc6c6ccccc65)cc4)sc3C(C)(C)c3cccc1c32]
6i
TABLE 3-continued
Structural formulae of the materials for the OLEDs
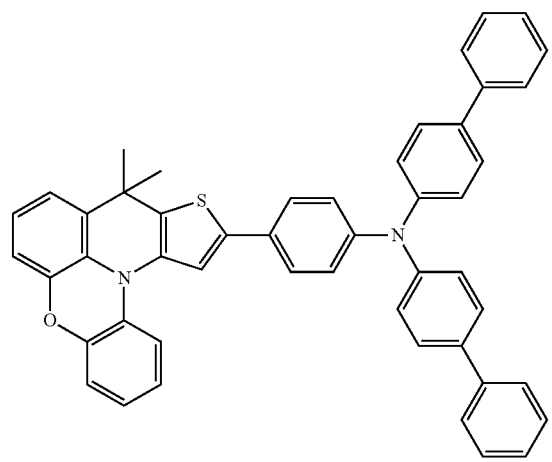 [SMILES: CC1(C)c2cccc3c2N(c2ccccc2O3)c2cc(-c3ccc(N(c4ccc(-c5ccccc5)cc4)c4ccc(-c5ccccc5)cc4)cc3)sc21]
6j
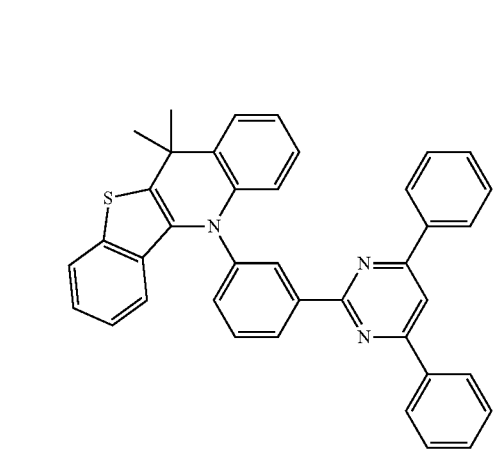 [SMILES: CC1(C)c2ccccc2N(c2cccc(-c3nc(-c4ccccc4)cc(-c4ccccc4)n3)c2)c2c1sc1ccccc21]
8a
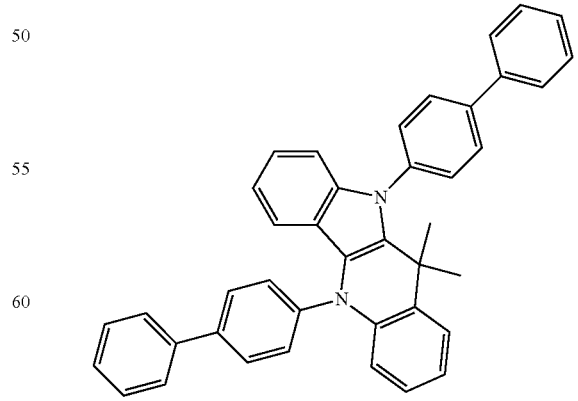
9

TABLE 3-continued

Structural formulae of the materials for the OLEDs

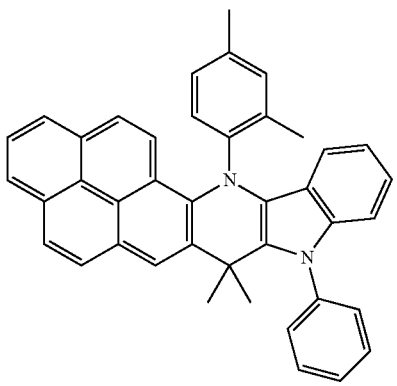 [SMILES: Cc1ccc(N2c3c(cc4ccc5cccc6ccc3c4c56)C(C)(C)c3c2c2ccccc2n3-c2ccccc2)c(C)c1]

10

The invention claimed is:

1. A compound of formula (1) or formula (2),

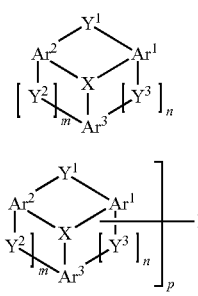

wherein

X is, identically or differently on each occurrence, N, P, or P=O;

Y1 is, identically or differently on each occurrence, C(R$^1$)$_2$ or NR$^1$;

Y$^2$, Y$^3$ is, identically or differently on each occurrence, a single bond or C(R$^1$)$_2$, NR$^1$, O, S, C=O, C=NR$^1$, C=C(R$^1$)$_2$, Si(R$^1$)$_2$, BR$^1$, PR$^1$, P(=O)R$^1$, SO, or SO$_2$; with the proviso that if any one of Y$^1$, Y$^2$ or Y$^3$ is NR$^1$, then R$^1$ of NR$^1$ is an aromatic or heteroaromatic ring system, which is optionally substituted by one or more radicals R$^2$;

Ar$^1$ is, identically or differently on each occurrence, a group of the following formula (3), formula (4), or formula (5),

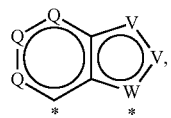

wherein the group is bonded to X and to Y$^1$ via the two positions denoted by * and wherein the group is optionally bonded to Y$^3$ via a further adjacent position and wherein W is, identically or differently on each occurrence, C or N;

V for W=C, is, identically or differently on each occurrence, CR, N, NR, S, or O, with the proviso that precisely one symbol V stands for NR, S, or O; or, for W=N is, identically or differently on each occurrence, CR or N;

Q is on each occurrence, identically or differently; CR or N;

wherein V or Q stands for C if a group Y$^3$ is bonded to this group V or Q;

Ar$^2$, Ar$^3$ is, identically or differently on each occurrence, an aryl or heteroaryl group having 5 to 18 aromatic ring atoms, optionally substituted by one or more radicals R;

L is a di-, tri-, tetra-, penta- or hexavalent straight-chain alkylene, alkylidene, alkyleneoxy, or thioalkyleneoxy group having 1 to 40 C atoms, or a branched or cyclic alkylene, alkylidene, alkyleneoxy, or thioalkyleneoxy group having 3 to 40 C atoms, or an alkenylene or alkynylene group having 2 to 40 C atoms, optionally substituted by in each case one or more radicals R$^2$, wherein one or more non-adjacent CH$_2$ groups are optionally replaced by —R$^2$C=CR$^2$—, —C≡C—, Si(R$^2$)$_2$, C=O, C=NR$^2$, P(=O)R$^2$, S=O, SO$_2$, —O—, —S—, or —CONR$^2$—, and wherein one or more H atoms are optionally replaced by D, F, Cl, Br, I, CN, or NO$_2$, or a di-, tri-, tetra-, penta- or hexavalent aromatic or heteroaromatic ring system having 5 to 40 aromatic ring atoms, optionally substituted by one or more radicals R$^2$, or P(R$^2$)$_{3-p}$, P(=O)(R$^2$)$_{3-p}$, C(R$^2$)$_{4-p}$, Si(R$^2$)$_{4-p}$, N(Ar)$_{3-p}$, or a combination of two, three, four, or five of these systems; or L is a chemical bond; L is bonded to any desired position of Ar$^1$, Ar$^2$, Ar$^3$, Y$^1$, Y$^2$ or Y$^3$ instead of a radical R or R$^1$;

R, R$^1$ is, identically or differently on each occurrence, selected from the group consisting of H, D, F, Cl, Br, I, CN, NO$_2$, N(Ar)$_2$, N(R$^2$)$_2$, C(=O)Ar, C(=O)R$^2$, P(=O)(Ar)$_2$, a straight-chain alkyl, alkoxy or thioalkyl group having 1 to 40 C atoms, a branched or cyclic alkyl, alkoxy or thioalkyl group having 3 to 40 C atoms, and an alkenyl or alkynyl group having 2 to 40 C atoms, each of which is optionally substituted by one or more radicals R$^2$, wherein one or more non-adjacent CH$_2$ groups are optionally replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S, or CONR$^2$, and wherein one or more H atoms are optionally replaced by D, F, Cl, Br, I, CN, NO$_2$, an aromatic or heteroaromatic ring system having 5 to 80, aromatic ring atoms, optionally substituted by one or more radicals R$^2$, an aryloxy or heteroaryloxy group having 5 to 60 aromatic ring atoms, optionally substituted by one or more radicals R$^2$, or an aralkyl or heteroaralkyl group having 5 to 60 aromatic ring atoms, optionally substituted by one or more radicals R², wherein two or more adjacent substituents R or two substituents R¹ which are bonded in the same group Y optionally define a mono- or polycyclic, aliphatic, aromatic, or heteroaromatic ring system, optionally substituted by one or more radicals R²;

R² is, identically or differently on each occurrence, selected from the group consisting of H, D, F, Cl, Br, I, CN, NO₂, N(Ar)₂, N(R³)₂, C(=O)Ar, C(=O)R³, P(=O)(Ar)₂, a straight-chain alkyl, alkoxy or thioalkyl group having 1 to 40 C atoms, a branched or cyclic alkyl, alkoxy or thioalkyl group having 3 to 40 C atoms, or an alkenyl or alkynyl group having 2 to 40 C atoms, optionally substituted by one or more radicals R³, wherein one or more non-adjacent CH₂ groups are optionally replaced by R³C=CR³, C≡C, Si(R³)₂, Ge(R³)₂, Sn(R³)₂, C=O, C=S, C=Se, C=NR³, P(O)(R³), SO, SO₂, NR³, O, S, or CONR³, and wherein one or more H atoms are optionally replaced by D, F, Cl, Br, I, CN, NO₂, an aromatic or heteroaromatic ring system having 5 to 60 aromatic ring atoms, optionally substituted by one or more radicals R³, an aryloxy or heteroaryloxy group having 5 to 60 aromatic ring atoms, optionally substituted by one or more radicals R³, or an aralkyl or heteroaralkyl group having 5 to 60 aromatic ring atoms, wherein two or more adjacent substituents R² optionally define a monocyclic or polycyclic, aliphatic, aromatic, or heteroaromatic ring system, optionally substituted by one or more radicals R³;

Ar is, identically or differently on each occurrence, an aromatic or heteroaromatic ring system having 5-30 aromatic ring atoms, optionally substituted by one or more non-aromatic radicals R³; two radicals Ar which are bonded to the same N atom or P atom are optionally bridged to one another by a single bond or a bridge selected from N(R³), C(R³)₂, O, or S;

R³ is selected from the group consisting of H, D, F, CN, an aliphatic hydrocarbon radical having 1 to 20 C atoms, and an aromatic or heteroaromatic ring system having 5 to 30 aromatic ring atoms, in which one or more H atoms are optionally replaced by D, F, Cl, Br, I, or CN, wherein two or more adjacent substituents R³ optionally define a mono- or polycyclic, aliphatic, aromatic or heteroaromatic ring system;

m, n are, identically or differently on each occurrence, 0 or 1, wherein m=0 or n=0 means that no group Y is present;

p is 2, 3, 4, 5, or 6, with the proviso that p is not greater than the maximum valence of L;

wherein the following compounds are excluded from the invention:

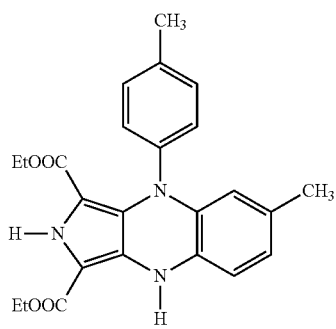

-continued

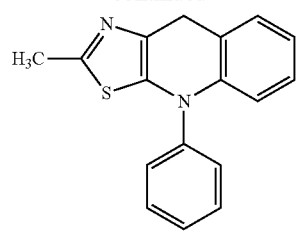

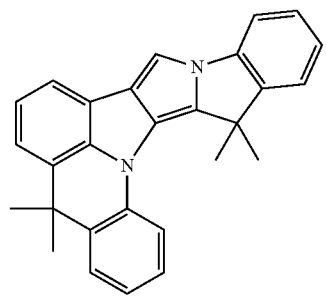

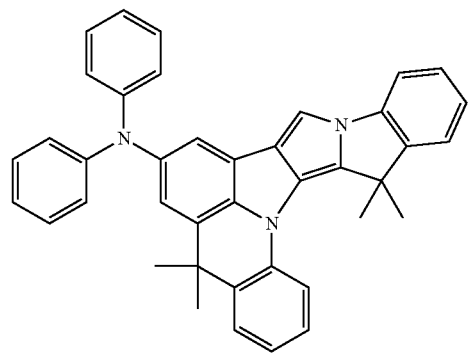

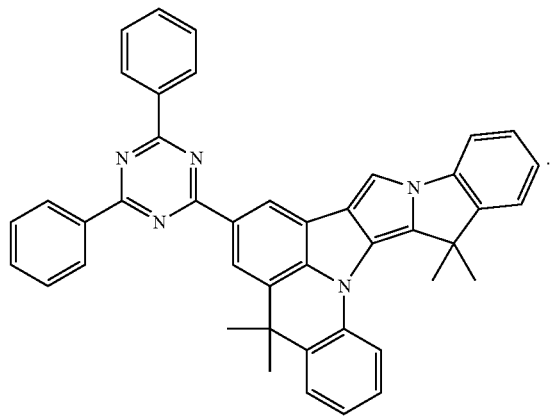

2. The compound of claim 1, wherein Ar² and Ar³ are, identically or differently on each occurrence, an aryl or heteroaryl group having 5 to 10 aromatic ring atoms, optionally substituted by one or more radicals R.

3. The compound of claim 1, wherein the compound is selected from the compounds of formulae (5) to (11):

formula (5)

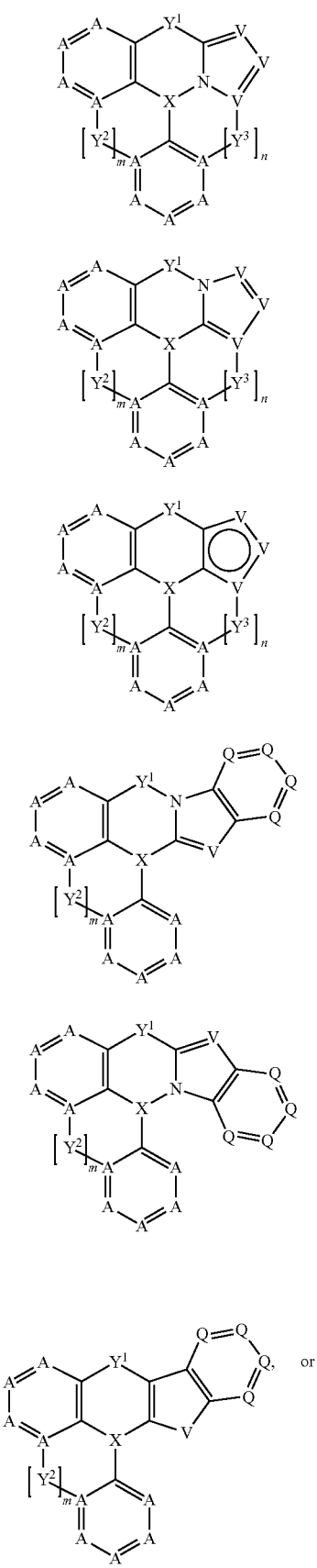

formula (6)

formula (7)

formula (8)

formula (9)

formula (10) or

-continued

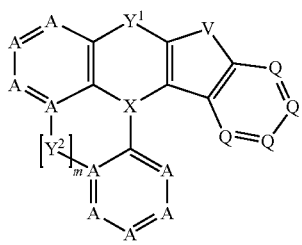

formula (11)

wherein

A is, identically or differently on each occurrence, CR or N; or two adjacent groups A together stand for NR, O or S, so that a five-membered ring arises; A is C if a group $Y^2$ or $Y^3$ is bonded to this A;

or selected from two or more compounds of the formulae (5) to (11), identical or different on each occurrence, connected to one another via L.

4. The compound of claim 1, wherein the compound is selected from the compounds of formulae (5a) to (11a),

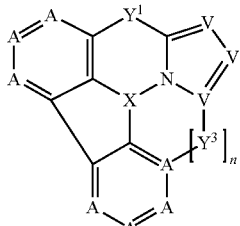

formula (5a)

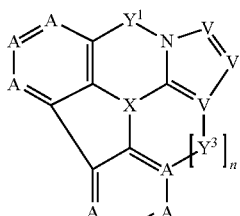

formula (6a)

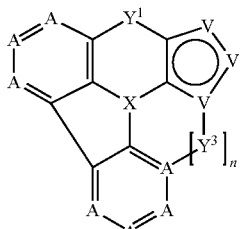

formula (7a)

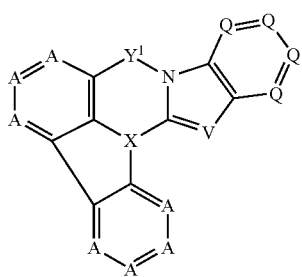

formula (8a)

-continued

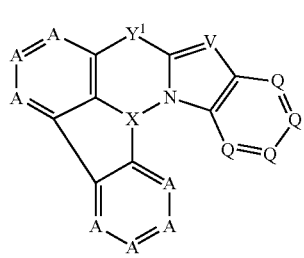

formula (9a)

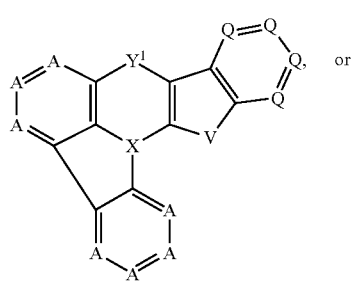

formula (10a) or

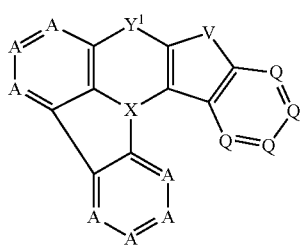

formula (11a)

wherein
A is, identically or differently on each occurrence, CR or N; or two adjacent groups A together stand for NR, O or S, so that a five-membered ring arises; A is C if a group $Y^2$ or $Y^3$ is bonded to this A;
or selected from two or more compounds of the formulae (5a) to (11a), identical or different on each occurrence, connected to one another via L.

5. The compound of claim 1, wherein the compound is selected from the compounds of formulae (5b) to (11b),

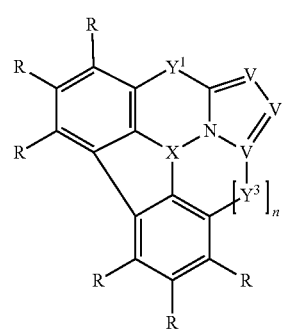

formula (5b)

-continued

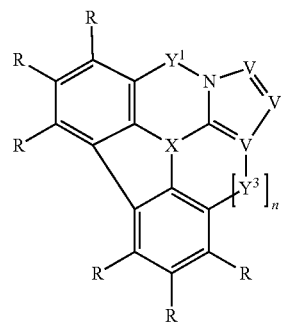

formula (6b)

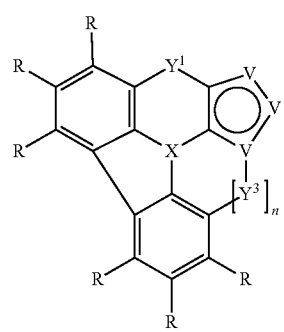

formula (7b)

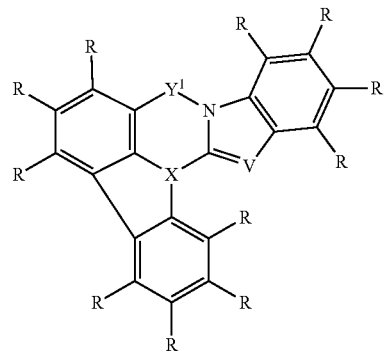

formula (8b)

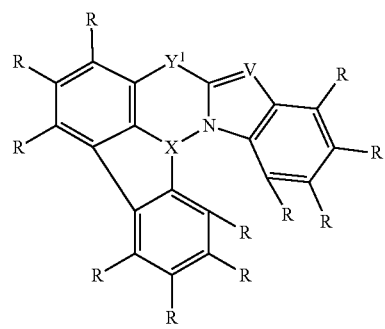

formula (9b)

formula (10b)

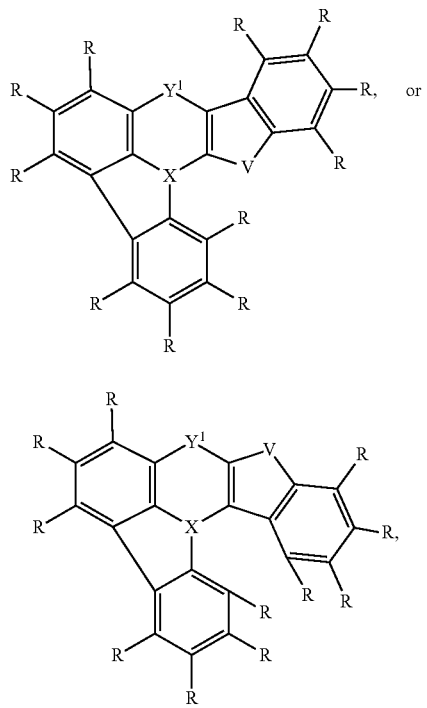

formula (11b)

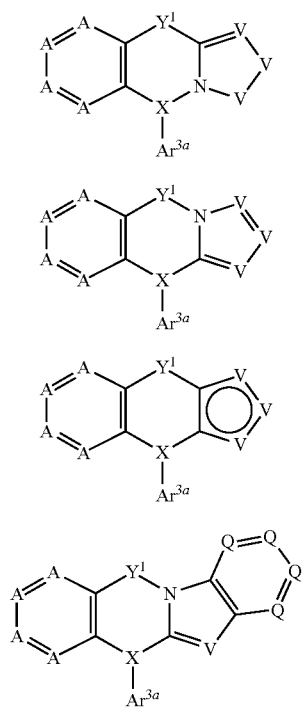

or selected from two or more compounds of the formulae (5b) to (11b), identical or different on each occurrence, connected to one another via L.

6. The compound of claim 1, selected from the o the compounds of the formulae (5c) to (11c), formula (5c)

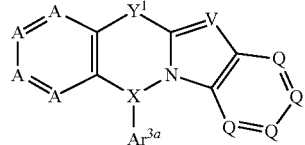

formula (6c)

formula (7c)

formula (8c)

formula (9c)

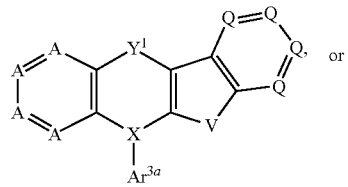

formula (10c)

formula (11c)

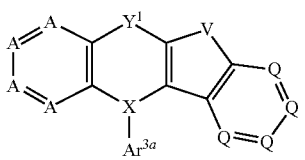

wherein

Ar$^{3a}$ is a six-membered aryl ring group or a six-membered heteroaryl ring group, optionally substituted by one or more radicals R;

or selected from two or more compounds of the formulae (5c) to (11c), identical or different on each occurrence, connected to one another via L.

7. The compound of claim 1, wherein X is nitrogen.

8. The compound of claim 1, wherein Y$^2$ and Y$^3$ are, identically or differently on each occurrence, a single bond, C(R$^1$)$_2$, or N(R$^1$).

9. The compound of claim 1, wherein the compound is selected from the compounds of formulae (5d) to (11d), formula (5d)

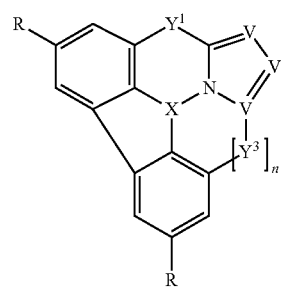

formula (6d)

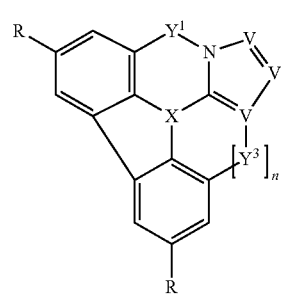

-continued

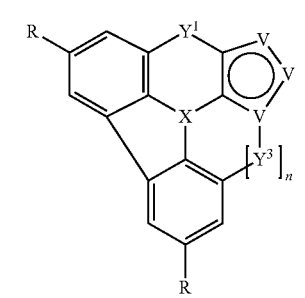
formula (7d)

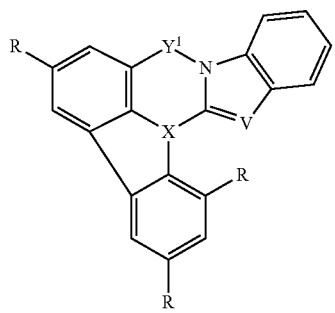
formula (8d)

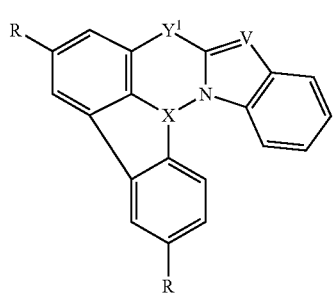
formula (9d)

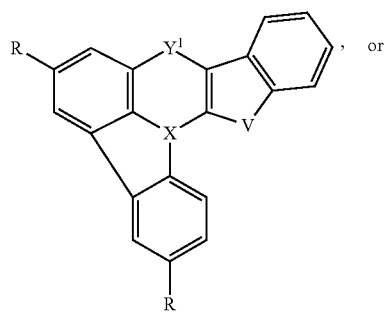
formula (10d), or

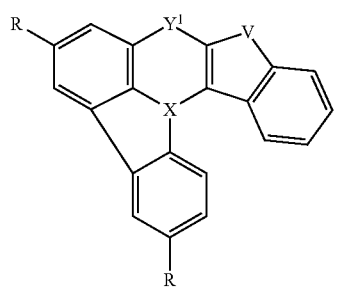
formula (11d)

or selected from two or more compounds of the formulae (5d) to (11d), identical or different on each occurrence, connected to one another via L.

10. The compound of claim 9, wherein at least one radical R is selected from structures of the formulae (12) to (15),

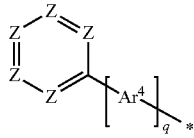
formula (12)

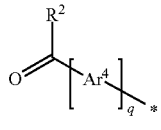
formula (13)

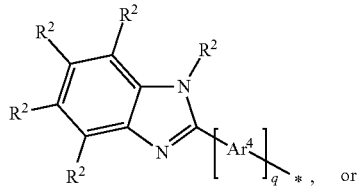
formula (14)

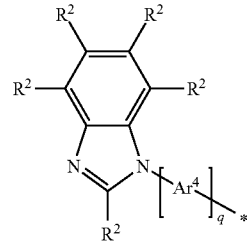
formula (15)

and/or wherein at least one group L stands for a group selected from formulae (16) to (18),

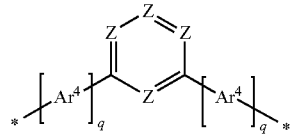
formula (16)

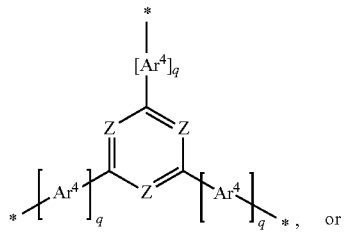
formula (17), or

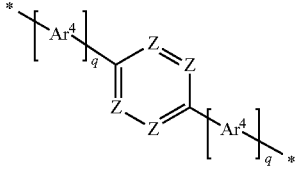
formula (18)

wherein

* indicates the position of the bond of the group of the formula (12) to (18);

Z is, identically or differently on each occurrence, $CR^2$ or N, with the proviso that one group Z, two groups Z, or three groups Z, stand for N;

$Ar^4$ is, identically or differently on each occurrence, a divalent aryl or heteroaryl group having 5 to 18 C atoms, optionally substituted by one or more radicals $R^2$;

q is on each occurrence, identically or differently, 0, 1, 2, or 3;

and/or wherein at least one substituent R is selected from the group consisting of —$NAr_2$, a triarylamine derivative, a carbazole derivative, an indenocarbazole derivative, an indolocarbazole derivative, an azacarbazole derivative, an indole derivative, a furan derivative, a benzofuran derivative, a dibenzofuran derivative, a thiophene derivative, a benzothiophene derivative, and a dibenzothiophene derivative, each of which is optionally substituted by one or more radicals $R^2$.

11. The compound of claim 1, wherein at least one radical R is selected from structures of the formulae (12) to (15),

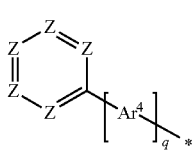

formula (12)

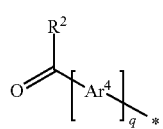

formula (13)

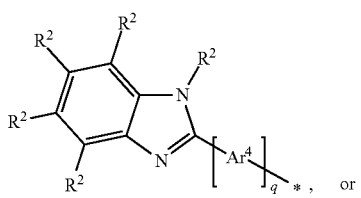

formula (14)

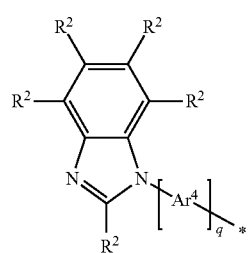

formula (15)

and/or wherein at least one group L stands for a group selected from formulae (16) to (18),

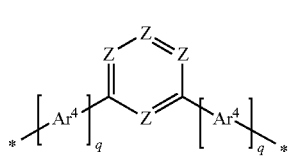

formula (16)

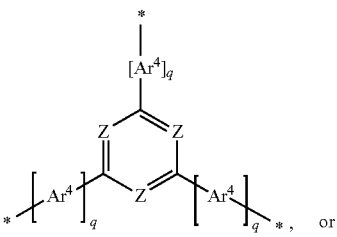

formula (17)

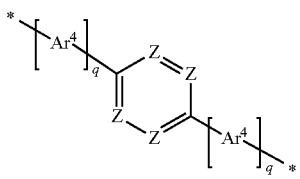

formula (18)

wherein

* indicates the position of the bond of the group of the formula (12) to (18);

Z is, identically or differently on each occurrence, $CR^2$ or N, with the proviso that one group Z, two groups Z, or three groups Z, stand for N;

$Ar^4$ is, identically or differently on each occurrence, a divalent aryl or heteroaryl group having 5 to 18 C atoms, optionally substituted by one or more radicals $R^2$;

q is on each occurrence, identically or differently, 0, 1, 2, or 3;

and/or wherein at least one substituent R is selected from the group consisting of —$NAr_2$, a triarylamine derivative, a carbazole derivative, an indenocarbazole derivative, an indolocarbazole derivative, an azacarbazole derivative, an indole derivative, a furan derivative, a benzofuran derivative, a dibenzofuran derivative, a thiophene derivative, a benzothiophene derivative, and a dibenzothiophene derivative, each of which is optionally substituted by one or more radicals $R^2$.

12. A process for the preparation of the compound of claim 1, said process comprising:
a) synthesizing a skeleton which carries a reactive leaving group instead of a group R; and
b) introducing the group R by a coupling reaction.

13. A formulation comprising at least one compound of claim 1 and one or more solvents.

14. An electronic device comprising at least one compound of claim 1.

15. An organic electroluminescent device comprising the compound of claim 1 as matrix material for fluorescent or phosphorescent emitters in an emitting layer and/or as hole-blocking material in a hole-blocking layer and/or as electron-transport material in an electron-transport layer and/or as electron-blocking or exciton-blocking material in an electron-blocking or exciton-blocking layer and/or as hole-transport material in a hole-transport layer or in a hole-injection layer.

16. The compound of claim 1, wherein $Ar^2$ and $Ar^3$ are, identically or differently on each occurrence, selected from benzene, thiophene, pyrrole, furan, pyridine, pyrimidine, triazine, benzothiophene, indole, benzofuran, or naphthalene.

17. A mixture comprising at least one compound of claim 1 and at least one further compound.

18. A formulation comprising the mixture of claim 17 and one or more solvents.

19. An electronic device comprising the mixture of claim 17.

20. An organic electroluminescent device comprising the mixture of claim 17 as matrix material for fluorescent or phosphorescent emitters in an emitting layer and/or as hole-blocking material in a hole-blocking layer and/or as electron-transport material in an electron-transport layer and/or as electron-blocking or exciton-blocking material in an electron-blocking or exciton-blocking layer and/or as hole-transport material in a hole-transport layer or in a hole-injection layer.

\* \* \* \* \*